(12) United States Patent
Clark et al.

(10) Patent No.: US 6,190,617 B1
(45) Date of Patent: *Feb. 20, 2001

(54) SAMPLE CONTAINER SEGMENT ASSEMBLY

(75) Inventors: Frederick L. Clark; Larry W. Moore, both of Plano; Donny Ray Walker, Coppell, all of TX (US); John M Clemens, Wadsworth, IL (US); William J. Kanewske, III, Dallas, TX (US); B. Jane Smith, Vernon Hills, IL (US)

(73) Assignee: Abbott Laboratories, Abbott Park, IL (US)

( * ) Notice: Under 35 U.S.C. 154(b), the term of this patent shall be extended for 0 days.

This patent is subject to a terminal disclaimer.

(21) Appl. No.: 08/956,939

(22) Filed: Oct. 23, 1997

Related U.S. Application Data

(60) Division of application No. 08/713,553, filed on Sep. 9, 1996, now Pat. No. 5,762,878, which is a continuation-in-part of application No. 08/126,411, filed on Sep. 24, 1993, now abandoned, which is a continuation-in-part of application No. 07/915,162, filed on Jul. 20, 1992, now Pat. No. 5,376,313, application No. 07/915,163, filed on Jul. 20, 1992, now abandoned, application No. 07/915,164, filed on Jul. 20, 1992, now abandoned, application No. 07/915,166, filed on Jul. 20, 1992, now abandoned, application No. 07/915,167, filed on Jul. 20, 1992, now abandoned, application No. 07/915,168, filed on Jul. 20, 1992, now abandoned, application No. 07/916,425, filed on Jul. 20, 1992, now abandoned, application No. 07/916,551, filed on Jul. 20, 1992, now abandoned, application No. 07/916,556, filed on Jul. 20, 1992, now abandoned, application No. 07/916,737, filed on Jul. 20, 1992, now Pat. No. 5,451,528, application No. 07/917,253, filed on Jul. 20, 1992, now abandoned, application No. 07/917,634, filed on Jul. 20, 1992, now abandoned, application No. 08/027,268, filed on Mar. 18, 1993, now abandoned, application No. 08/027,270, filed on Mar. 18, 1993, now abandoned, application No. 08/027,387, filed on Mar. 18, 1993, now abandoned, application No. 08/027,388, filed on Mar. 18, 1993, now abandoned, application No. 08/027,481, filed on Mar. 18, 1993, now abandoned, application No. 08/027,269, filed on Mar. 18, 1993, now abandoned, and application No. 08/027,482, filed on Mar. 18, 1993, now abandoned, which is a continuation-in-part of application No. 07/916,556, said application No. 08/027,269, is a continuation-in-part of application No. 07/917,634, said application No. 08/126,411, application No. 07/915,162, application No. 07/915,163, application No. 07/915,164, application No. 07/915,166, application No. 07/915,167, application No. 07/915,168, application No. 07/916,425, application No. 07/916,551, application No. 07/916,556, application No. 07/916,737, application No. 07/916,253, application No. 07/916,634, application No. 08/027,268, application No. 08/027,270, application No. 08/027,387, application No. 08/027,388, and application No. 08/027,481, each is a continuation-in-part of application No.07/859,218, filed on Mar. 27, 1992, now abandoned.

(51) Int. Cl.[7] .................................................. G01N 35/00
(52) U.S. Cl. .......................... 422/104; 422/63; 422/64; 422/102; 436/43; 436/47; 206/563
(58) Field of Search ................................ 422/63, 64, 102, 422/ 104; 436/43, 47; 206/443, 446, 563; 211/74, 77, 188, 194; 220/737

(56) References Cited

U.S. PATENT DOCUMENTS

| 2,958,439 | 11/1960 | Yochem . |
|---|---|---|
| 3,814,582 | 6/1974 | Rohrbaugh et al. . |

(List continued on next page.)

FOREIGN PATENT DOCUMENTS

| 03016294 | 10/1981 | (DE) . |
|---|---|---|
| 03029440 | 2/1982 | (DE) . |

(List continued on next page.)

*Primary Examiner*—Long V. Le
(74) *Attorney, Agent, or Firm*—David L. Weinstein

(57) ABSTRACT

A sample container segment assembly for use in an automated, continuous, and random access analytical system is disclosed. The assembly includes a sample container which is received by a sample container segment, and the sample container segment is received on a carousel of the automated analytical instrument. The test sample container includes an upper skirt and a body having a reservoir for receipt of the test sample. The segment includes a base, a frame, and a handle. The frame has a shelf for which the upper skirt of the test sample container rests on, and has openings for receipt of the body of the sample container. The carousel has a carousel trough for receipt of the base of the sample container segment, and has a plurality of alignment pins disposed in the carousel trough. The base of the sample container segment has a circular slot and an elongated slot for receiving the alignment pins and positioning the sample container segment relative to the carousel. The sample container segment can include a liquid level sensing sleeve which is made of a conductive material and surrounds the reservoir of the test sample container inserted therein. Alternatively, the test sample container can have a conductive core which surrounds the reservoir and extends therebelow. The container sample segment can also include various sleeves, or springs and arms, for securing and positioning the test sample container within the sample container segment.

2 Claims, 49 Drawing Sheets

U.S. PATENT DOCUMENTS

| | | | |
|---|---|---|---|
| 3,915,651 | 10/1975 | Nishiu . | |
| 3,917,455 | 11/1975 | Bak et al. | 23/253 R |
| 3,951,608 | 4/1976 | Trod . | |
| 4,000,974 | 1/1977 | Acord | 23/230 R |
| 4,038,555 | 7/1977 | Freeman . | |
| 4,070,156 | 1/1978 | Moran et al. | 23/253 R |
| 4,082,121 | 4/1978 | Sturm et al. | 141/27 |
| 4,111,754 | 9/1978 | Park . | |
| 4,113,436 | 9/1978 | Werder et al. . | |
| 4,130,796 | 12/1978 | Shum | 324/61 R |
| 4,141,687 | 2/1979 | Forrest et al. . | |
| 4,148,607 | 4/1979 | Bernoco et al. | 23/230 B |
| 4,169,543 | 10/1979 | Hall | 22/56 |
| 4,234,538 | 11/1980 | Ginsberg et al. . | |
| 4,234,539 | 11/1980 | Ginsberg et al. . | |
| 4,234,540 | 11/1980 | Ginsberg et al. . | |
| 4,256,725 | 3/1981 | Rutner et al. . | |
| 4,268,477 | 5/1981 | Herzstark . | |
| 4,276,051 | 6/1981 | Ginsberg et al. . | |
| 4,276,260 | 6/1981 | Drbal et al. . | |
| 4,278,437 | 7/1981 | Haggar . | |
| 4,298,571 | 11/1981 | Difulvio et al. . | |
| 4,302,421 | 11/1981 | Baker . | |
| 4,311,394 | 1/1982 | Manabe . | |
| 4,311,959 | 1/1982 | Riessland et al. | 324/61 P |
| 4,313,735 | 2/1982 | Yamashita et al. | 23/230 R |
| 4,314,968 | 2/1982 | Guigan | 422/64 |
| 4,315,891 | 2/1982 | Sakurada | 422/64 |
| 4,325,910 | 4/1982 | Jordan . | |
| 4,326,851 | 4/1982 | Bello et al. . | |
| 4,336,000 | 6/1982 | Jorgensen et al. | 417/53 |
| 4,338,279 | 7/1982 | Orimo et al. | 422/64 |
| 4,346,056 | 8/1982 | Sakurda . | |
| 4,346,742 | 8/1982 | Chase et al. | 141/1 |
| 4,406,547 | 9/1983 | Aihara | 356/414 |
| 4,412,973 | 11/1983 | Guigan | 422/72 |
| 4,429,583 | 2/1984 | Watanabe et al. | 73/864 |
| 4,430,299 | 2/1984 | Horne | 422/64 |
| 4,448,752 | 5/1984 | Banno et al. | 422/81 |
| 4,449,405 | 5/1984 | Franz et al. . | |
| 4,451,433 | 5/1984 | Yamashita et al. . | |
| 4,456,037 | 6/1984 | Gocho | 141/1 |
| 4,457,893 | 7/1984 | Takekawa | 422/64 |
| 4,459,265 | 7/1984 | Berglund | 422/64 |
| 4,470,008 | 9/1984 | Kato | 324/61 R |
| 4,471,295 | 9/1984 | Vermeiren | 324/61 R |
| 4,472,505 | 9/1984 | Manabe et al. . | |
| 4,483,927 | 11/1984 | Takekawa . | |
| 4,495,149 | 1/1985 | Iwata et al. . | |
| 4,499,766 | 2/1985 | Fathauer et al. . | |
| 4,502,126 | 2/1985 | Mizoguchi . | |
| 4,515,889 | 5/1985 | Klose et al. | 435/4 |
| 4,517,160 | 5/1985 | Galle et al. | 422/65 |
| 4,526,046 | 7/1985 | Oberli . | |
| 4,536,369 | 8/1985 | Sakurada et al. | 422/65 |
| 4,540,549 | 9/1985 | Manabe . | |
| 4,554,134 | 11/1985 | Tervamaki et al. . | |
| 4,555,941 | 12/1985 | Fathauer et al. | 73/304 |
| 4,558,946 | 12/1985 | Galle et al. | 356/73 |
| 4,568,873 | 2/1986 | Oyanagi et al. | 324/61 P |
| 4,571,160 | 2/1986 | Galle et al. . | |
| 4,575,492 | 3/1986 | David et al. | 436/164 |
| 4,584,885 | 4/1986 | Cadwell | 73/862.61 |
| 4,586,546 | 5/1986 | Mezei et al. | 141/2 |
| 4,595,562 | 6/1986 | Liston et al. . | |
| 4,612,289 | 9/1986 | Furuta et al. | 436/34 |
| 4,629,703 | 12/1986 | Uffenheimer . | |
| 4,634,576 | 1/1987 | Galle et al. | 422/102 |
| 4,644,807 | 2/1987 | Mar | 73/864.62 |
| 4,647,432 | 3/1987 | Wakatake . | |
| 4,676,100 | 6/1987 | Eichberger | 73/304 |
| 4,678,752 | 7/1987 | Thorne et al. . | |
| 4,679,446 | 7/1987 | Sheehan et al. . | |
| 4,687,638 | 8/1987 | Benajam | 422/73 |
| 4,695,430 | 9/1987 | Coville et al. . | |
| 4,699,766 | 10/1987 | Yamashita . | |
| 4,699,767 | 10/1987 | Aihara | 422/65 |
| 4,731,225 | 3/1988 | Wakatake | 422/65 |
| 4,736,638 | 4/1988 | Okawa et al. | 73/864.24 |
| 4,737,342 | 4/1988 | Herrmann et al. . | |
| 4,738,825 | 4/1988 | Kelln et al. . | |
| 4,764,342 | 8/1988 | Kelln et al. | 422/72 |
| 4,766,078 | 8/1988 | Gang . | |
| 4,774,055 | 9/1988 | Wakatake et al. . | |
| 4,781,891 | 11/1988 | Galle et al. . | |
| 4,788,150 | 11/1988 | Nelson et al. | 436/45 |
| 4,794,085 | 12/1988 | Jessop et al. | 436/54 |
| 4,799,599 * | 1/1989 | Herrmann | 215/307 |
| 4,805,469 | 2/1989 | Commarmot . | |
| 4,808,380 | 2/1989 | Minekane | 422/64 |
| 4,815,632 | 3/1989 | Ball et al. . | |
| 4,818,492 | 4/1989 | Shimizo . | |
| 4,821,080 | 4/1989 | Hayashi . | |
| 4,826,319 | 5/1989 | Namba et al. | 356/339 |
| 4,826,660 | 5/1989 | Smith et al. . | |
| 4,834,944 | 5/1989 | Wakatake | 422/64 |
| 4,836,037 | 6/1989 | Nohl et al. | 73/864.16 |
| 4,836,038 | 6/1989 | Baldwyn | 73/864.21 |
| 4,837,159 | 6/1989 | Yamada . | |
| 4,844,887 | 7/1989 | Galle et al. . | |
| 4,863,695 | 9/1989 | Fullemann | 422/100 |
| 4,864,169 | 9/1989 | Rioux et al. . | |
| 4,876,204 | 10/1989 | Inoue et al. . | |
| 4,900,513 | 2/1990 | Barker et al. . | |
| 4,906,433 | 3/1990 | Minekane . | |
| 4,908,186 | 3/1990 | Sakamaki . | |
| 4,908,320 | 3/1990 | Zakowski et al. . | |
| 4,914,377 | 4/1990 | Russell | 324/690 |
| 4,919,887 | 4/1990 | Wakatake | 422/67 |
| 4,924,702 | 5/1990 | Park | 73/304 C |
| 4,926,150 | 5/1990 | Buchschmid et al. | 335/196 |
| 4,926,701 | 5/1990 | Tompkins | 73/864.15 |
| 4,927,765 | 5/1990 | Saxon et al. | 436/43 |
| 4,961,906 | 10/1990 | Anderson et al. . | |
| 4,965,049 | 10/1990 | Lillig et al. . | |
| 4,970,053 | 11/1990 | Fechtner . | |
| 4,970,468 | 11/1990 | Ishizawa et al. . | |
| 4,971,913 | 11/1990 | Manabe et al. . | |
| 4,977,786 | 12/1990 | Davis . | |
| 4,984,475 | 1/1991 | Uffenheimer | 73/864.22 |
| 5,005,409 | 4/1991 | Hochstein | 73/304 |
| 5,012,683 | 5/1991 | Davis . | |
| 5,027,075 | 6/1991 | Harding, Jr. | 324/662 |
| 5,035,150 | 7/1991 | Tompkins | 73/864.15 |
| 5,043,143 | 8/1991 | Shaw et al. | 422/65 |
| 5,045,286 | 9/1991 | Kitajima et al. | 422/100 |
| 5,049,359 | 9/1991 | Azuma et al. | 422/67 |
| 5,049,824 | 9/1991 | Suzuki et al. | 324/660 |
| 5,049,826 | 9/1991 | Sasao | 324/662 |
| 5,051,238 | 9/1991 | Umetsu et al. . | |
| 5,053,715 | 10/1991 | Andermo | 324/662 |
| 5,057,823 | 10/1991 | Dyer et al. | 340/620 |
| 5,063,790 | 11/1991 | Freeman et al. | 73/864.14 |
| 5,083,283 | 1/1992 | Imai et al. . | |
| 5,084,242 | 1/1992 | Sakuma et al. | 422/100 |
| 5,087,423 | 2/1992 | Ishibashi | 422/67 |
| 5,096,670 | 3/1992 | Harris et al. | 422/65 |
| 5,101,673 | 4/1992 | Uffenheimer | 73/864.22 |
| 5,104,621 | 4/1992 | Pfost et al. | 422/67 |
| 5,104,624 | 4/1992 | Labriola | 422/100 |
| 5,104,808 | 4/1992 | Laska et al. | 436/48 |

| | | | | | | |
|---|---|---|---|---|---|---|
| 5,108,703 | 4/1992 | Pfost et al. .............................. 422/65 | | 00251086 | 11/1987 | (EP) . |
| 5,114,679 | 5/1992 | Reifler et al. ........................ 422/100 | | 00252631 | 1/1988 | (EP) . |
| 5,116,578 | 5/1992 | Baxter .................................... 422/63 | | 00271398 | 6/1988 | (EP) . |
| 5,128,105 | * 7/1992 | Berthhold et al. ................... 422/104 | | 00282601 | 9/1988 | (EP) . |
| 5,136,250 | 8/1992 | Abdelli ................................ 324/661 | | 00289789 | 11/1988 | (EP) . |
| 5,137,693 | 8/1992 | Mawhirt ............................... 422/104 | | 0301584 | 2/1989 | (EP) . |
| 5,141,871 | 8/1992 | Kureshy et al. ....................... 436/47 | | 00316766 | 5/1989 | (EP) . |
| 5,149,654 | 9/1992 | Gross et al. ......................... 435/287 | | 00336309 | 10/1989 | (EP) . |
| 5,158,748 | 10/1992 | Obi et al. ............................. 422/100 | | 0355738 | 2/1990 | (EP) . |
| 5,158,895 | 10/1992 | Ashihara et al. .................... 436/526 | | 0355849 | 2/1990 | (EP) . |
| 5,164,318 | 11/1992 | Sato et al. ........................... 435/288 | | 0359049 | 3/1990 | (EP) . |
| 5,167,922 | 12/1992 | Long ..................................... 422/58 | | 00388012 | 9/1990 | (EP) . |
| 5,167,926 | 12/1992 | Kimura et al. ........................ 422/67 | | 00388013 | 9/1990 | (EP) . |
| 5,175,086 | 12/1992 | Takekawa et al. .................. 435/7.92 | | 0387787 | 9/1990 | (EP) . |
| 5,178,834 | 1/1993 | Kagayama et al. .................... 422/65 | | 0409126 | 1/1991 | (EP) . |
| 5,187,990 | 2/1993 | Magnussen et al. .............. 73/864.18 | | 0410645 | 1/1991 | (EP) . |
| 5,192,505 | 3/1993 | Sakagami .............................. 422/64 | | 0411620 | 2/1991 | (EP) . |
| 5,204,264 | 4/1993 | Kaminer ................................. 436/8 | | 02239093 | 6/1991 | (EP) . |
| 5,204,269 | 4/1993 | Barker et al. .......................... 436/47 | | 00500506 | 8/1992 | (EP) . |
| 5,213,761 | 5/1993 | Sakagami .............................. 422/63 | | 00510686 | 10/1992 | (EP) . |
| | | | | 00513618 | 11/1992 | (EP) . |
| | FOREIGN PATENT DOCUMENTS | | | 00109922 | 5/1994 | (EP) . |
| 03134005 | 4/1982 | (DE) . | | 00559660 | 3/1980 | (JP) . |
| 03242459 | 5/1984 | (DE) . | | 05513552 | 4/1980 | (JP) . |
| 03242460 | 5/1984 | (DE) . | | 05524591 | 6/1980 | (JP) . |
| 03448121 | 7/1984 | (DE) . | | 00562560 | 1/1981 | (JP) . |
| 03500639 | 7/1985 | (DE) . | | 56-168553 | 12/1981 | (JP) . |
| 03605695 | 9/1986 | (DE) . | | 05782753 | 5/1982 | (JP) . |
| 03733098 | 4/1988 | (DE) . | | 57-156542 | 9/1982 | (JP) . |
| 04011584 | 10/1990 | (DE) . | | 00606635 | 2/1983 | (JP) . |
| 02468909 | 10/1979 | (EP) . | | 05838744 | 8/1983 | (JP) . |
| 02473723 | 1/1980 | (EP) . | | 58-161866 | 9/1983 | (JP) . |
| 00013452 | 7/1980 | (EP) . | | 05931455 | 2/1984 | (JP) . |
| 02446480 | 8/1980 | (EP) . | | 06057892 | 12/1985 | (JP) . |
| 02049179 | 12/1980 | (EP) | | 00616342 | 2/1986 | (JP) . |
| 02065298 | 6/1981 | (EP) . | | 00616343 | 2/1986 | (JP) . |
| 02068542 | 8/1981 | (EP) . | | 06180055 | 4/1986 | (JP) . |
| 00035320 | 9/1981 | (EP) . | | 06196468 | 5/1986 | (JP) . |
| 00041378 | 12/1981 | (EP) . | | 61-118662 | 6/1986 | (JP) . |
| 00043079 | 1/1982 | (EP) . | | 61-124869 | 6/1986 | (JP) . |
| 00051541 | 5/1982 | (EP) . | | 06135972 | 10/1986 | (JP) . |
| 00052006 | 5/1982 | (EP) . | | 06151938 | 11/1986 | (JP) . |
| 00054262 | 6/1982 | (EP) . | | 61-258171 | 11/1986 | (JP) . |
| 00061317 | 9/1982 | (EP) . | | 06145875 | 12/1986 | (JP) . |
| 02095403 | 9/1982 | (EP) . | | 06244663 | 2/1987 | (JP) . |
| 00062251 | 10/1982 | (EP) . | | 62-050645 | 3/1987 | (JP) . |
| 00074102 | 3/1983 | (EP) . | | 06218870 | 4/1987 | (JP) . |
| 00078948 | 5/1983 | (EP) . | | 62-133355 | 6/1987 | (JP) . |
| 00083474 | 7/1983 | (EP) . | | 62-133356 | 6/1987 | (JP) . |
| 00083651 | 7/1983 | (EP) . | | 06227221 | 7/1987 | (JP) . |
| 00089346 | 9/1983 | (EP) . | | 62-184358 | 8/1987 | (JP) . |
| 00101192 | 2/1984 | (EP) . | | 06243502 | 9/1987 | (JP) . |
| 0100663 | 2/1984 | (EP) . | | 62-211562 | 9/1987 | (JP) . |
| 00103622 | 3/1984 | (EP) . | | 62-217163 | 9/1987 | (JP) . |
| 02125962 | 3/1984 | (EP) . | | 06242143 | 10/1987 | (JP) . |
| 00107580 | 5/1984 | (EP) . | | 62-298765 | 12/1987 | (JP) . |
| 0109613 | 5/1984 | (EP) . | | 06315163 | 1/1988 | (JP) . |
| 02131168 | 6/1984 | (EP) . | | 06317175 | 4/1988 | (JP) . |
| 02131946 | 6/1984 | (EP) . | | 06371656 | 4/1988 | (JP) . |
| 02136953 | 9/1984 | (EP) . | | 06385458 | 4/1988 | (JP) . |
| 00129450 | 12/1984 | (EP) . | | 06388463 | 4/1988 | (JP) . |
| 00185330 | 6/1986 | (EP) . | | 06322514 | 6/1988 | (JP) . |
| 00192968 | 9/1986 | (EP) . | | 06322531 | 6/1988 | (JP) . |
| 00193016 | 9/1986 | (EP) . | | 63-158464 | 7/1988 | (JP) . |
| 0212455 | 3/1987 | (EP) . | | 06345069 | 9/1988 | (JP) . |
| 0216026 | 4/1987 | (EP) . | | 88045069 | 9/1988 | (JP) . |
| 0216177 | 4/1987 | (EP) . | | 06339650 | 10/1988 | (JP) . |
| 00222466 | 5/1987 | (EP) . | | 06339651 | 10/1988 | (JP) . |
| 02591344 | 6/1987 | (EP) . | | 63-238561 | 10/1988 | (JP) . |
| 00231430 | 8/1987 | (EP) . | | 63-275957 | 11/1988 | (JP) . |
| 00236928 | 9/1987 | (EP) . | | 63-293444 | 11/1988 | (JP) . |

| | | | | | | |
|---|---|---|---|---|---|---|
| 00649573 | 2/1989 | (JP) . | | 00255957 | 2/1990 | (JP) . |
| 06411909 | 2/1989 | (JP) . | | 00213746 | 4/1990 | (JP) . |
| 89009571 | 2/1989 | (JP) . | | 00217341 | 5/1990 | (JP) . |
| 00110607 | 3/1989 | (JP) . | | 00229989 | 7/1990 | (JP) . |
| 00110608 | 3/1989 | (JP) . | | 00242195 | 9/1990 | (JP) . |
| 00114542 | 3/1989 | (JP) . | | 00243146 | 9/1990 | (JP) . |
| 06463860 | 3/1989 | (JP) . | | 00247705 | 10/1990 | (JP) . |
| 00121910 | 4/1989 | (JP) . | | 00245818 | 12/1990 | (JP) . |
| 00121911 | 4/1989 | (JP) . | | 00318150 | 3/1991 | (JP) . |
| 06488234 | 4/1989 | (JP) . | | 00330819 | 5/1991 | (JP) . |
| 01138462 | 5/1989 | (JP) . | | 00346786 | 7/1991 | (JP) . |
| 00119071 | 6/1989 | (JP) . | | 03170851 | 7/1991 | (JP) . |
| 00120695 | 6/1989 | (JP) . | | 03172742 | 7/1991 | (JP) . |
| 00122139 | 6/1989 | (JP) . | | 00365502 | 10/1991 | (JP) . |
| 00139067 | 8/1989 | (JP) . | | 00004279 | 1/1992 | (JP) . |
| 01196574 | 8/1989 | (JP) . | | 00044533 | 1/1992 | (JP) . |
| 00142383 | 9/1989 | (JP) . | | 00439036 | 6/1992 | (JP) . |
| 00142384 | 9/1989 | (JP) . | | 00445774 | 7/1992 | (JP) . |
| 01219564 | 9/1989 | (JP) . | | 00059730 | 2/1993 | (JP) . |
| 01219668 | 9/1989 | (JP) . | | 00513272 | 2/1993 | (JP) . |
| 01221673 | 9/1989 | (JP) . | | 00534626 | 5/1993 | (JP) . |
| 01227950 | 9/1989 | (JP) . | | 08300393 | 2/1983 | (WO) . |
| 00131964 | 10/1989 | (JP) . | | 8301119 | 3/1983 | (WO) . |
| 00145870 | 10/1989 | (JP) . | | 08700086 | 1/1987 | (WO) . |
| 00147744 | 10/1989 | (JP) . | | 08703966 | 7/1987 | (WO) . |
| 00147746 | 10/1989 | (JP) . | | 08800704 | 1/1988 | (WO) . |
| 00138527 | 11/1989 | (JP) . | | 09107662 | 5/1991 | (WO) . |
| 01301170 | 12/1989 | (JP) . | | 09203714 | 3/1992 | (WO) . |
| 00025416 | 2/1990 | (JP) . | | | | |
| 00028217 | 2/1990 | (JP) . | | | | |

\* cited by examiner

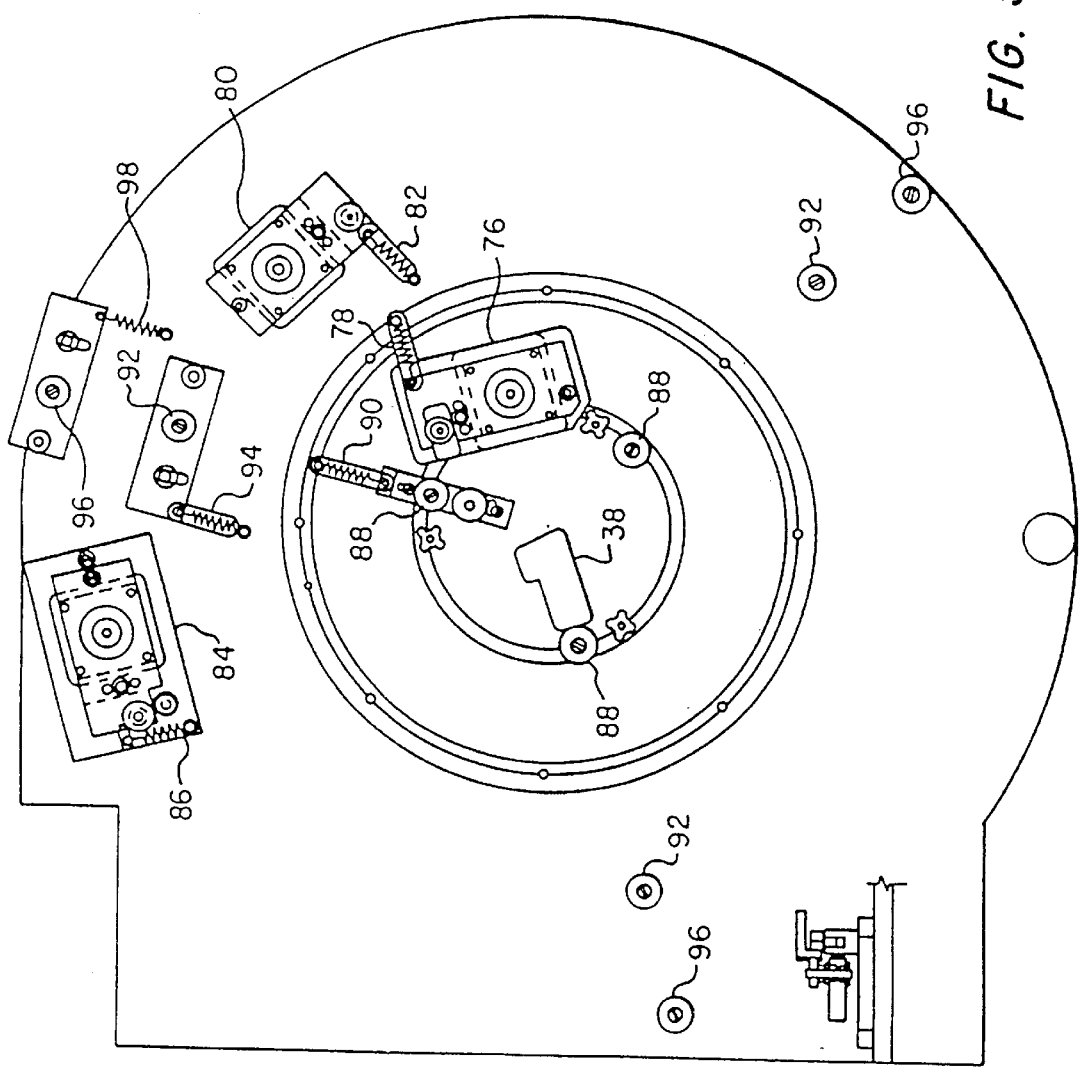

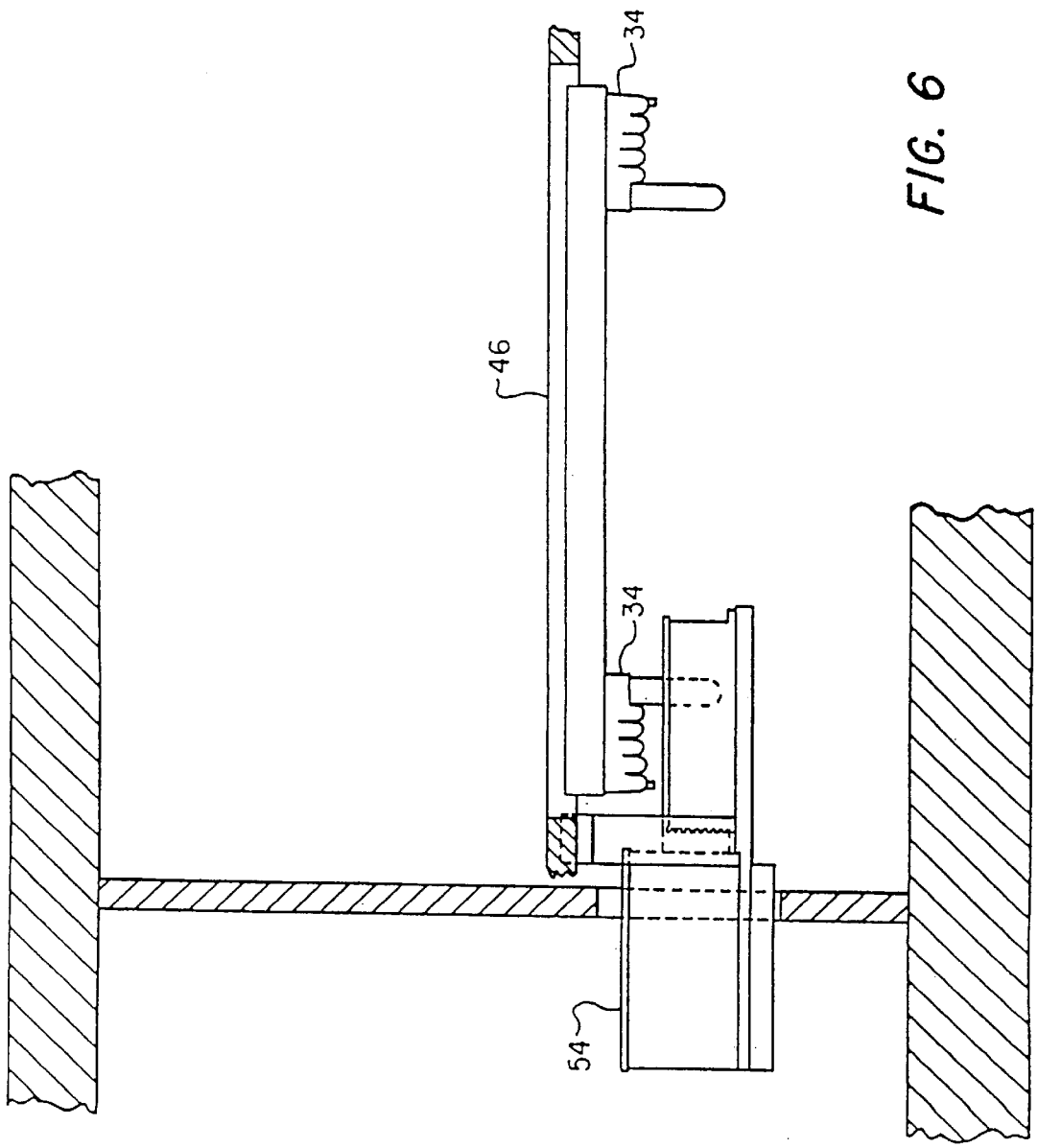

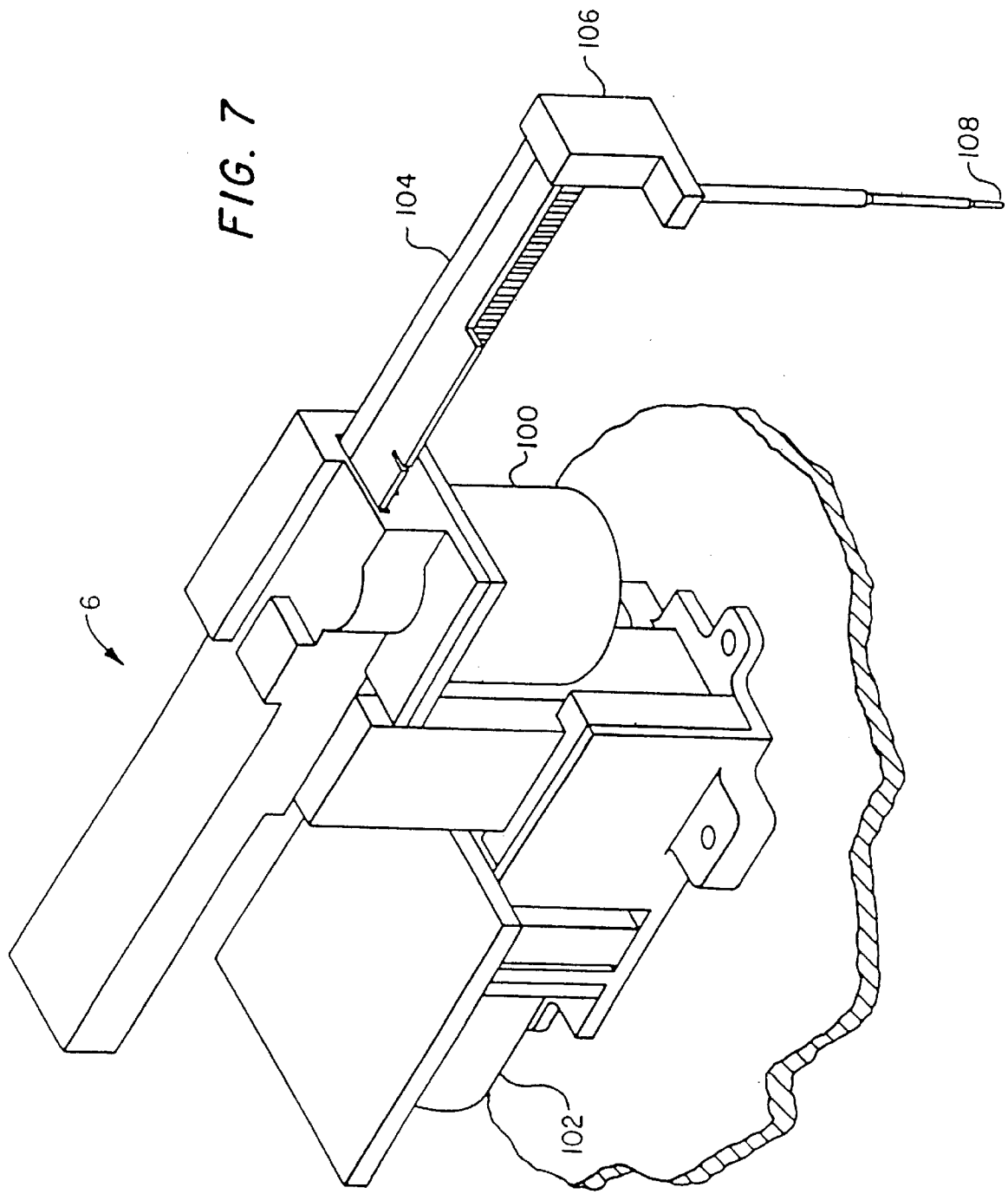

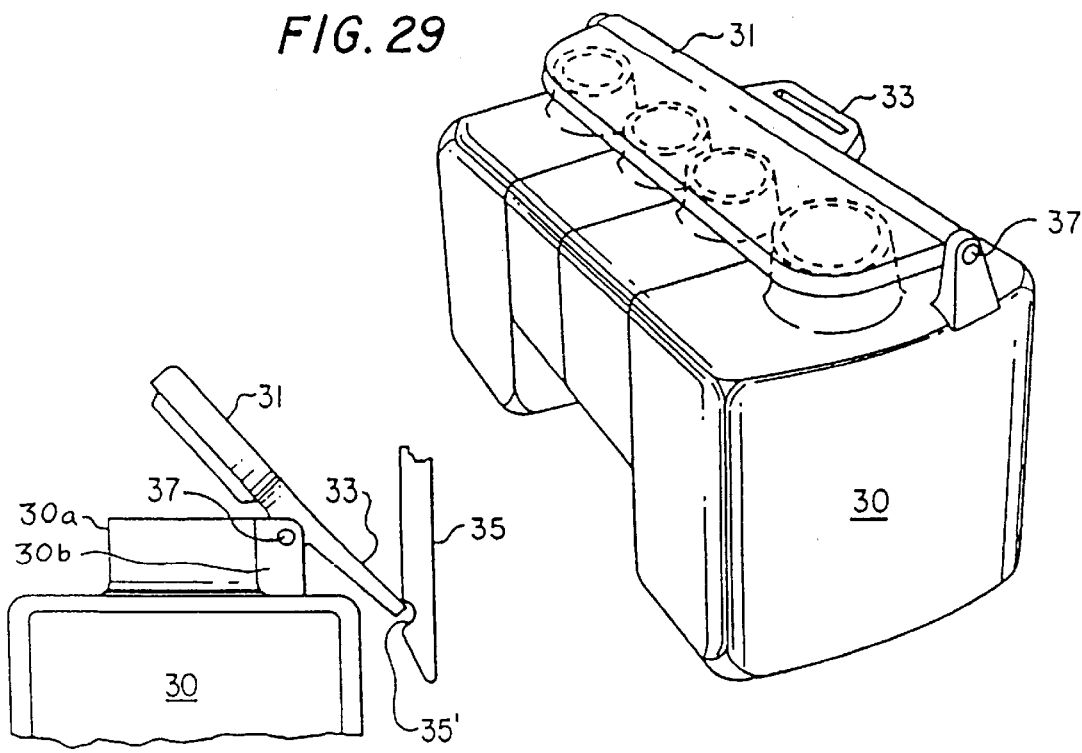
FIG. 29
FIG. 30
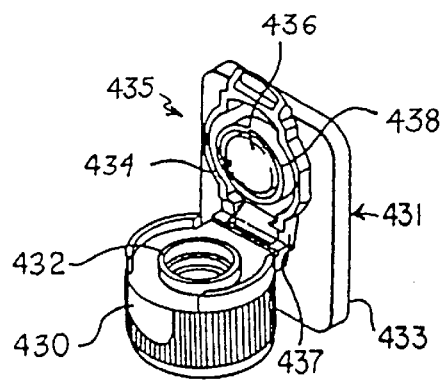
FIG. 33

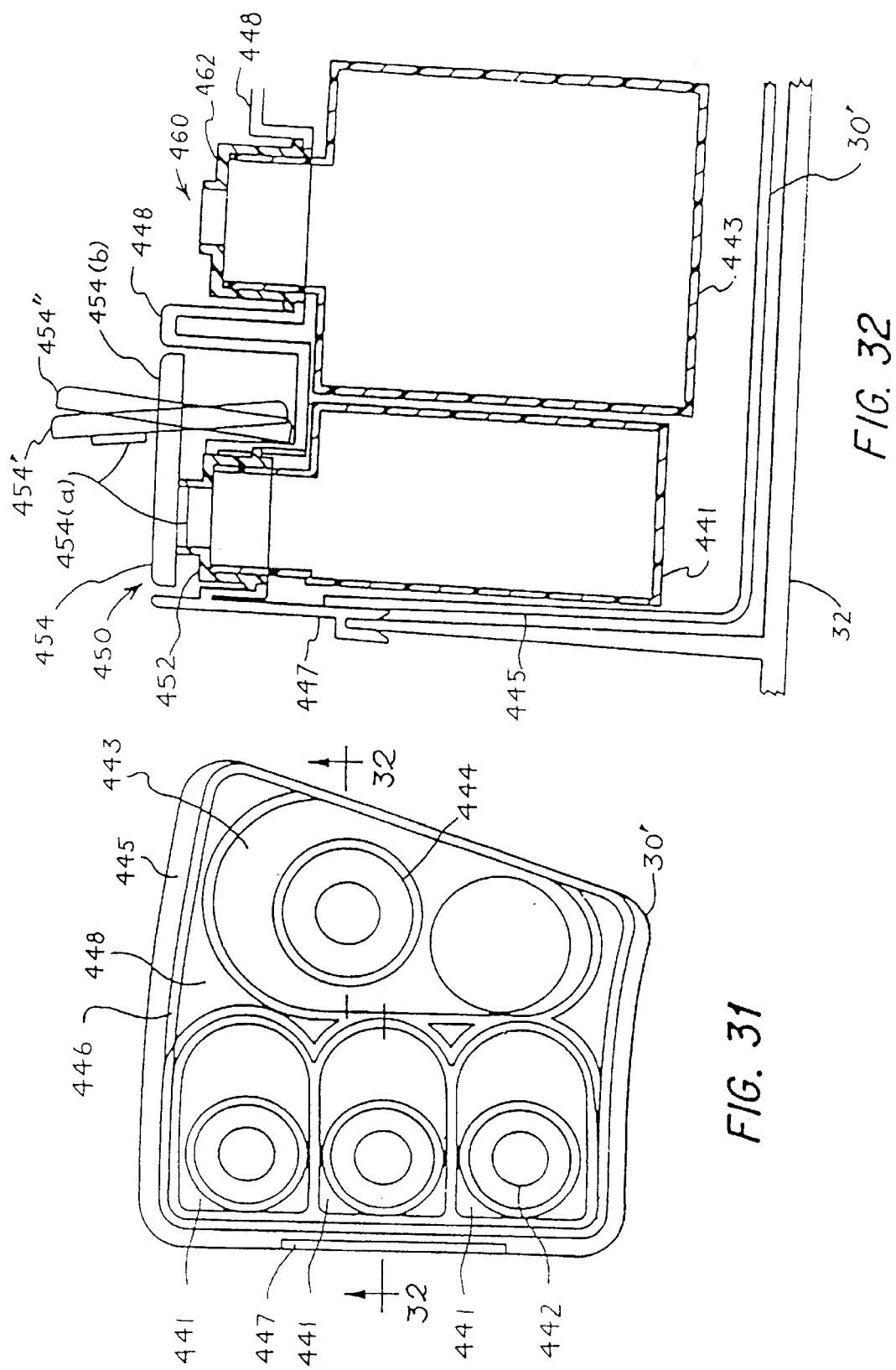

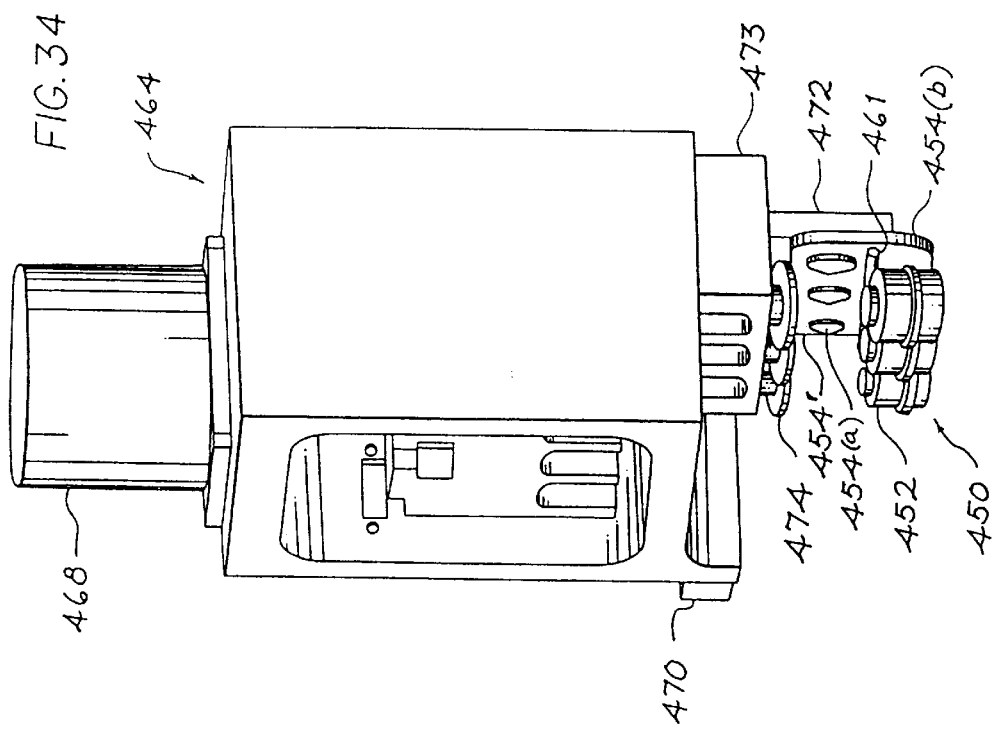
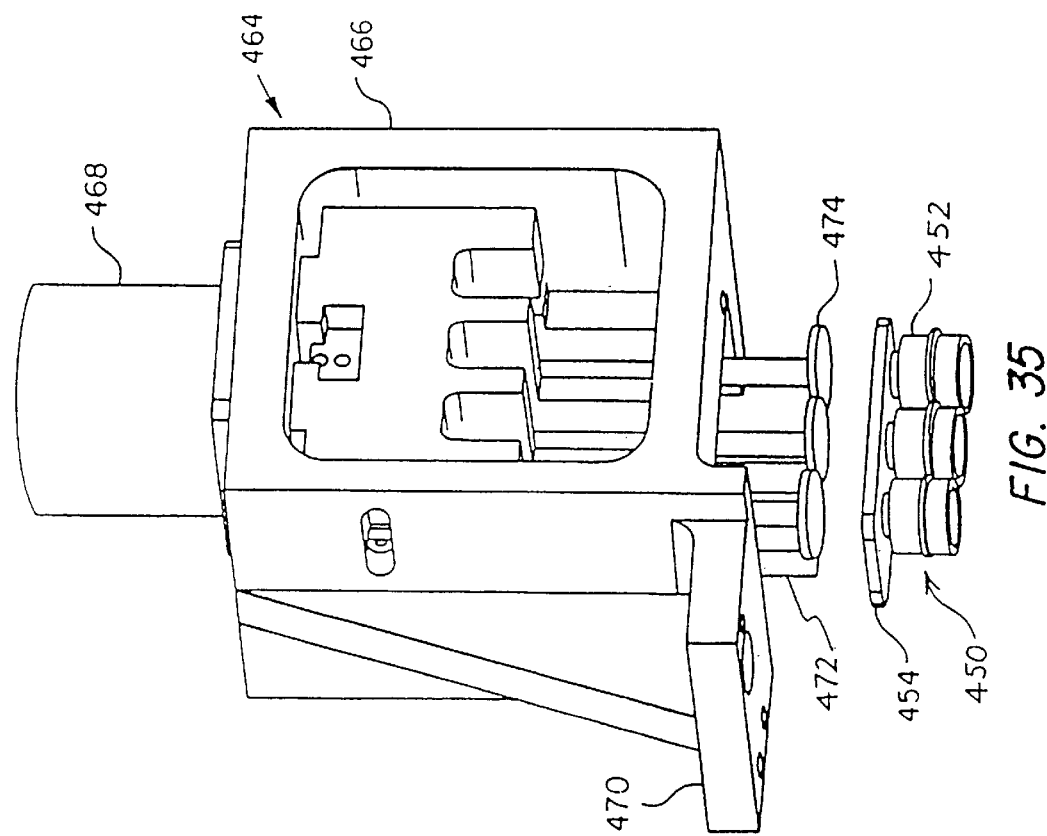

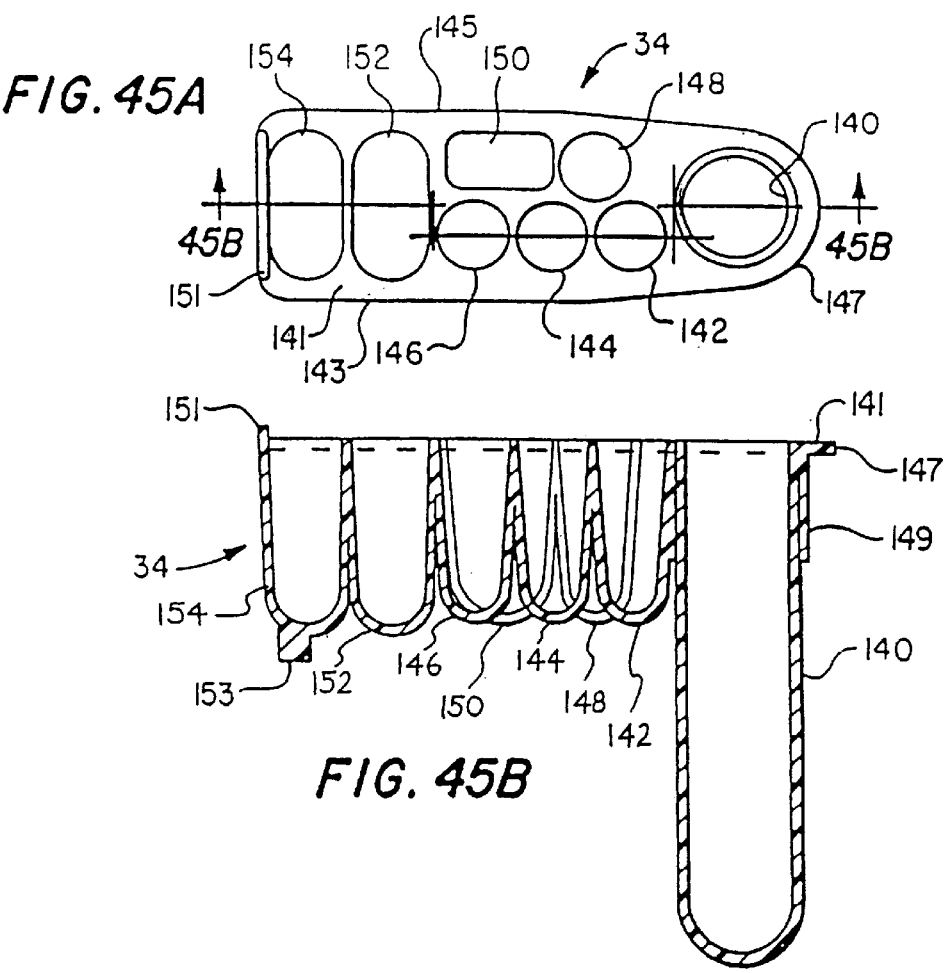
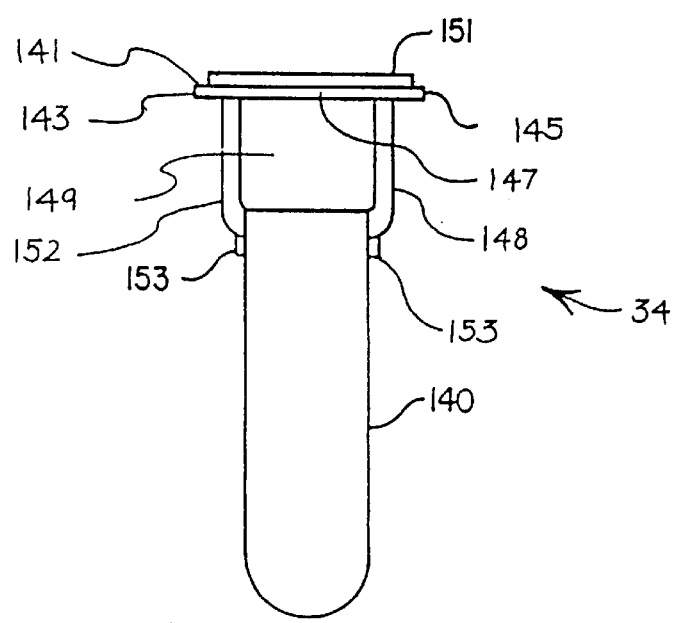
FIG. 45A
FIG. 45B
FIG. 45C

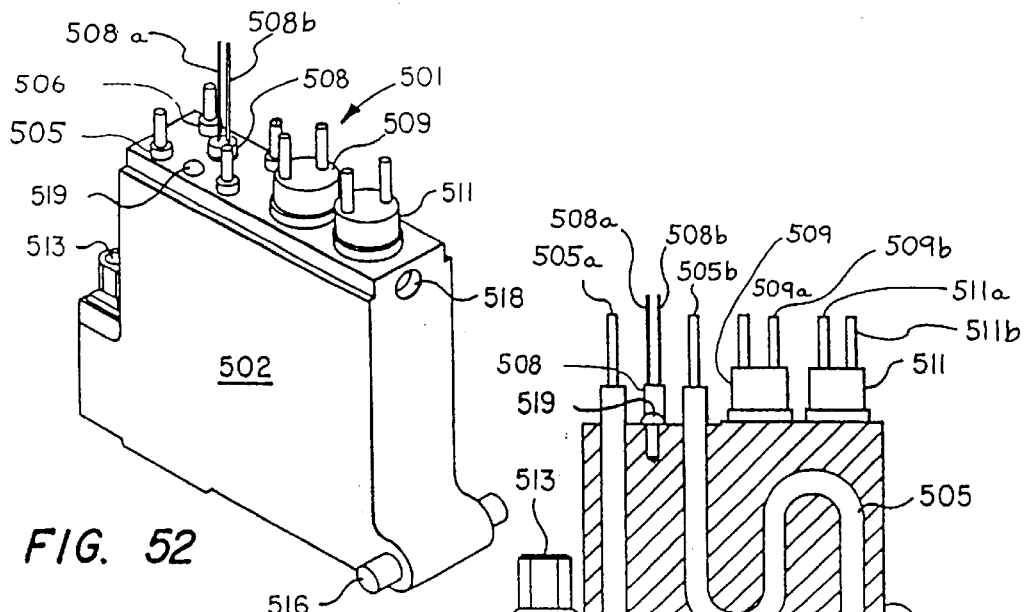
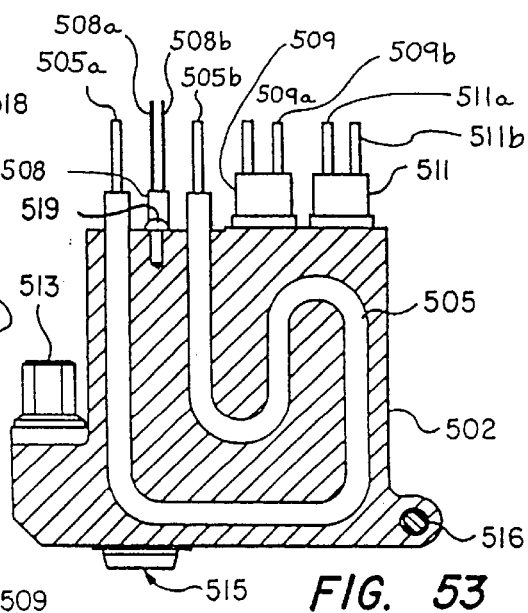
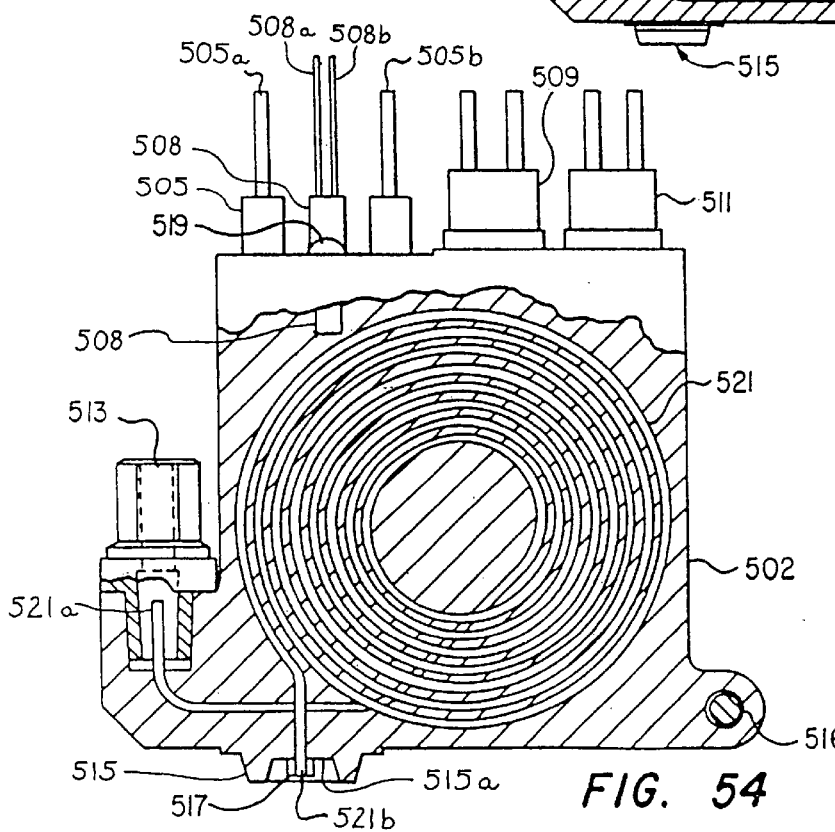
FIG. 52
FIG. 53
FIG. 54

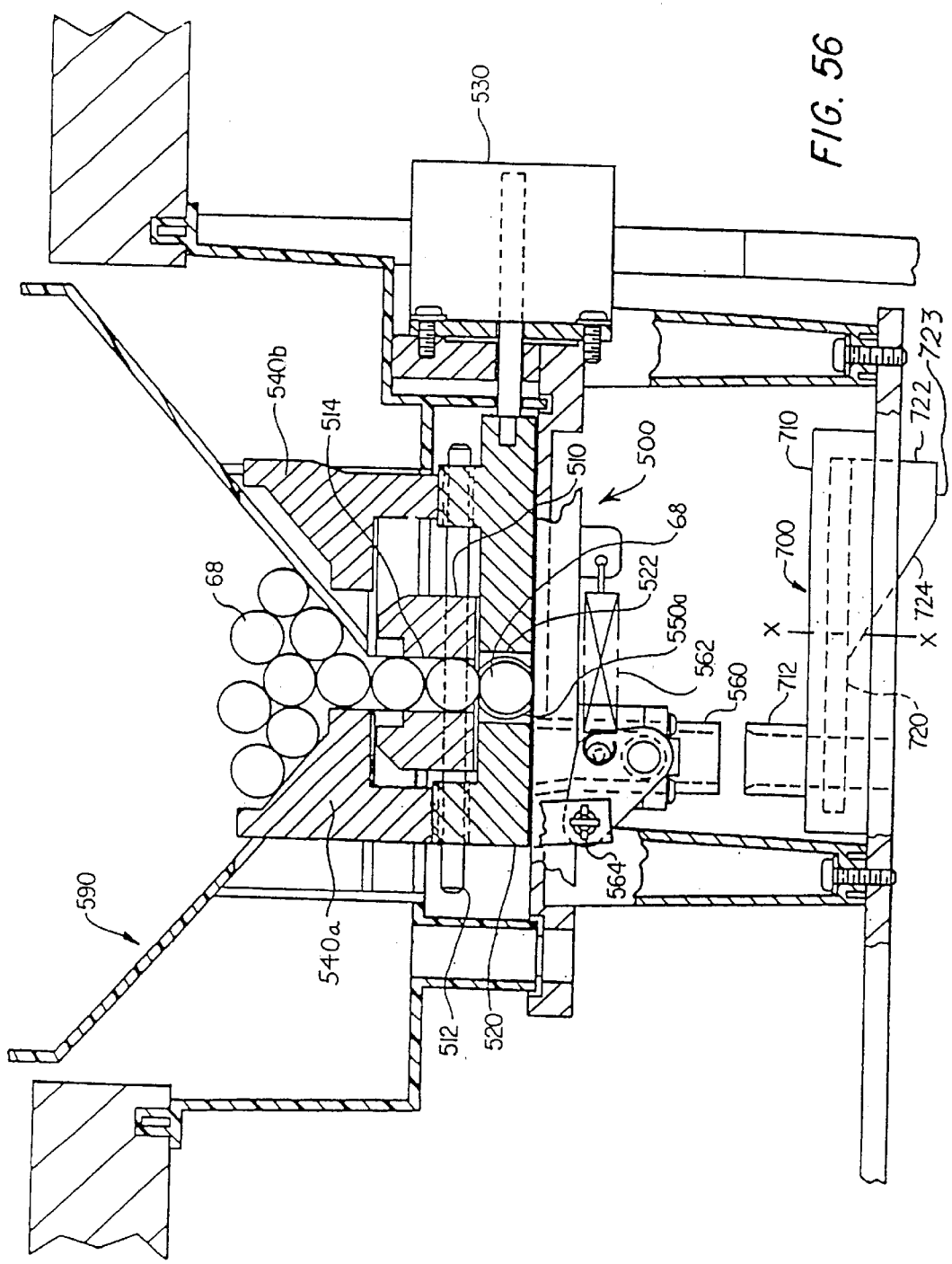

SAMPLE CONTAINER SEGMENT ASSEMBLY

This application is a division of U.S. patent application Ser. No. 08/713,553, filed Sep. 9, 1996, now U.S. Pat. No. 5,762,878, which is a continuation-in-part application of U.S. Ser. No. 08/126,411 filed Sep. 24, 1993, now abandoned, hereinafter the "Parent Application". The Parent Application is a continuation-in-part of U.S. Ser. No. 07/859,218, filed Mar. 27, 1992, now abandoned, hereinafter the "Original Application". The Parent Application is also a continuation-in-part application of the following U.S. Ser. Nos.: 07/195,162, now U.S. Pat. No. 5,376,313; 07/915,163; 07/915,164; 07/915,166; 07/915,167; 07/915,168; 07/196,425; 07/916,551; 07/916,556; 07/916,737, now U.S. Pat. No. 5,451,528; 07/917,253; and 07/917,634; all being filed on Jul. 20, 1992, and all being continuation-in-part applications of the Original Application and all abandoned except as noted. The Parent Application is also a continuation-in-part application of the following U.S. Ser. Nos.: 08/027,268; 08/027,270; 08/027,387; 08/027,388; and 08/027,481; all being filed on Mar. 18, 1993, and all being continuation-in-part applications of the Original Application and abandoned except as noted. The Parent Application is also a continuation-in-part application of U.S. Ser. No. 08/027,269, filed on Mar. 18, 1993, now abandoned, which is a continuation-in-part application of U.S. Ser. No. 07/917,634, filed on Jul. 20, 1992, now abandoned, which is a continuation-in-part of the Original Application. The Parent Application is also a continuation-in-part of U.S. Ser. No. 08/027,482, filed on Mar. 18, 1993, now abandoned, which is a continuation-in-part of U.S. Ser. No. 07/916,556, filed on Jul. 20, 1992, now abandoned, which is a continuation-in-part of the Original Application.

FIELD OF THE INVENTION

The present invention relates to a sample container segment, and more particularly, to a sample container segment which can hold multiple sample containers for an automated analytical instrument.

BACKGROUND OF THE INVENTION

Although various known clinical analyzers for chemical, immunochemical and biological testing of samples are available, clinical technology is rapidly changing due to increasing demands in the clinical laboratory to provide new levels of service. These new levels of service must be more cost effective to decrease the operating expenditures such as labor cost and the like, and must provide shorter turnaround time of test results to reduce the patient's length of stay in the hospital as well as improve efficiency of outpatient treatment. Modernization of analytical apparatus and procedure demands consolidation of work stations to meet the growing challenge placed on clinical laboratories.

Generally, analysis of a test sample involves the reaction of test samples with one or more reagents with respect to one or more analytes wherein it is frequently desired that the analysis be performed on a selective basis with respect to each test sample. However, due to the high demands placed on clinical laboratories regarding not only volume throughput but also the number and frequency of various analyses, there is a need to provide an automated analysis system which is capable of combining accurate analytical results, multiple test menu versatility, low reagent and fluids loss and consumption, and of great benefit and importance, continuous and high throughput.

The present automated clinical analysis systems provide much improved accuracy of analytical results in comparison with accuracies of earlier systems. In the present systems, analysis of a test sample typically involves forming a reaction mixture comprising the test sample and one or more reagents, and the reaction mixture is then analyzed by an apparatus for one or more characteristics of the test sample. Reliance on automated clinical analyzers has improved the efficiency of the laboratory procedures, inasmuch as the technician has fewer tasks to perform. Automated clinical analyzers provide results much more rapidly while frequently avoiding operator or technician error, thus placing emphasis on accuracy and repeatability of a variety of tests. Automated clinical analyzers presently available for routine laboratory tests include a transport or conveyor system designed to transport containers of sample liquids between various operating stations. For example, a reaction tube or cuvette containing a test sample may pass through a reagent filling station, mixing station, reaction forming station, detection stations, analysis stations, and the like. Such present transport systems are, however, not flexible in that transport is in one direction and the reaction tubes or cuvettes, once inserted into the apparatus, must pass through without access before analysis occurs. Even further, the present transport systems allow only batch-like operation in that once the system is initially loaded, testing may only be performed on the initially loaded samples during a single operation cycle; alternative or additional samples cannot be loaded during the operation cycle to allow continuing operations for extended periods.

As for multiple test menu versatility, some of the presently available automated clinical analyzers, such as automated immunoassay analyzers like the Abbott IMx® analyzer and the Abbott TDx® analyzer (Abbott Laboratories, Abbott Park, Ill., USA), utilize procedures involving a variety of different assay steps. These present systems have typically relied on detection and measurement of optical changes in a reaction mixture during the assay process. For example, a number of well-known techniques using techniques using single or multi-wavelength fluorescence include fluorescent polarization immunoassays (FPIA) employing homogeneous immunoassay techniques, microparticle enzyme immunoassays (MEIA) employing heterogeneous immunoassay techniques, and the like. the MEIA technology, such as that used on the Abbott IMx® analyzer, is used for high and low molecular weight analytes requiring greater sensitivity, and FPIA technology, such as that used on the Abbott TDx® analyzer, is used primarily for lower molecular weight analytes. A front surface fluorometer is used in these systems to quantify a fluorescent product generated in the MEIA assays, while a fluorescence polarization optical system is used to quantify the degree of tracer binding to antibody in the FPIA assays. The test samples are automatically processed in certain of these systems, such as the Abbott IMx® analyzer and Abbott TDx® analyzer, by a robotic arm with a pipetting probe and a rotating carousel which positions the samples for processing. These systems are typically compact table-top analyzers which offer fully automated, walk-away immunoassay testing capabilities for both routine and specialized immunoassays. These nonisotopic methods eliminate radioactivity disposal problems and increase reagent shelf life while meeting the diverse requirements of a multitude of different assays. Though these presently available automated clinical analyzers provide a degree of improved multiple test menu versatility in comparison to earlier systems and practices, the present analyzers remain limited in that these systems are one direction only systems, or batch analyzers, which permit the analysis of multiple samples and provide for access to the test samples for the formation of subsequent reaction mixtures, but permit only one type of anaylsis at a time. It would, thus, be an improvement to provide a random access analyzer which allows for analysis of multiple test samples for multiple analytes. It would be an even further improvement if such a random access analyzer allowed for continuous operations; that is, if additional or alternative samples could be loaded for analysis during analysis operations by the system, without interruption of the analysis operations.

With respect to reagent and fluids consumption and loss in present automated clinical analyzers, a common feature of those analyzers is the inclusion of various reagents within the apparatus itself or placed near the apparatus for pipetting purposes. In these systems, liquid reagents, in bulk form, are selected for the various types of tests which are to be performed on the test sample, and are stored in or near the apparatus. Reagent delivery units, such as pumps and the like, along with valves, control and pipette mechanisms, are included in the present automated analyzers so that different reagents can be mixed according to the type of test to be performed. In certain of these present analyzers, for example, the Abbott IMx® analyzer previously mentioned, all the steps required for analysis of test samples are automatically performed and those steps include numerous checks of the subsystems to insure that assays are run to completion with valid results. In the Abbott IMx® in particular, quantification of the fluorescence intensity in the MEIA method and polarization in the FPIA method, as well as the final data reduction, are fully automated on the analyzer and results are printed by the analyzer and may be accessed through suitable means for automatic data collection by a laboratory computer. These various aspects of the present automated clinical analyzers, like the Abbott IMx®, help limit reagent and fluid consumption and loss, as well as provide other advantages. Even with those advantages, however, improvement in reagent and fluids consumption and loss in an analysis system would be desirable. Even further, such improvement in consumption and loss by these, combined with benefits of continuous operations, accuracy of results, and test menu versatility would be a significant improvement in the art.

With respect to continuous and high throughput in automated analytical systems, the prior systems have been unable to provide these desirable characteristics. In the prior automated analytical systems, the systems are initially loaded with a plurality of test samples. The samples are then each tested during a full cycle of testing by the systems. Though the number of samples which may be initially loaded in these systems is fairly large, it is not possible to load additional test samples in these systems at the same time the systems are testing the initial load. Additional samples may only be loaded after testing of the prior sample load is complete. In order to increase throughput in these systems then, it would be advantageous to provide an automated analytical system which allow for loading of additional samples at any time, even while the system is testing other samples. It would be an even further advantage if such a system could provide accurate results, multiple test menu versatility, and low reagent and fluids loss and consumption while at the same time allowing continuous access to and testing of samples. The prior systems have been unable to provide these advantages. The present automated continuous and random access system provides all these advantages. In addition to those advantages, the present invention also provides additional improvements directed to specific aspects, parts, and operations of these systems.

Other benefits and advantages, in addition to those previously described (i.e., accurate analytical results, multiple test menu versatility, low reagent and fluids consumption and loss, and continuous and high throughput), directed to specific aspects, parts, and operations of automated clinical analyzers would also be improvements in the art. For example, the invention further provides advantageous mechanisms for loading particular containers. These mechanisms are of great importance because small, non-uniform containers are necessary in certain instances. Where many of these containers must be employed, it becomes hard, if not impossible, for an operator to maintain adequate supply to the instrument if loading and positioning of the containers is largely manual. The present invention provides improved containers and loading mechanisms to allow easy and continuous loading and processing capability.

SUMMARY OF THE INVENTION

The automated analytical system of the present invention is capable of simultaneously performing two or more assays on a plurality of test samples in a continuous and random access fashion. In particular, the automated immunoassay analytical system apparatus of the invention can be viewed as a microprocessor based system of integrated subassemblies with different groups of assays being continuously run through separate and changeable software modules. The microprocessor based system uses robotic arm pipettors with two degrees of freedom and bi-directional rotating carousels to process samples. Critical assay steps such as incubations, washes and specimen dilution are performed automatically by the instrument as scheduled. The scheduling provided by the system allows for continued operation as desired, since kitting operations and processing operations are independent. Even where continued operation requires addition or alteration of samples placed in the kitting area, the scheduling functions to cause the system to process an optimum throughput in the least amount of time.

According to the invention, an automated continuous and random access analytical system, capable of simultaneously effecting multiple assays of a plurality of liquid samples, is provided. The invention enables performing a method wherein various assays are scheduled for a plurality of liquid samples. Through kitting means, the present system is capable of creating a unit dose disposable by separately transferring liquid sample and reagents to a reaction vessel without initiation of an assay reaction sequence. From the kitting means, multiple, kitted unit dose disposables are transferred to a process area, wherein an aliquot is mixed for each independent sample with one or more liquid reagents at different times in a reaction vessel to form independent reaction mixtures. Independent scheduling of such kitting and mixing is achieved during incubation of the multiple reaction mixtures, simultaneously and independently. The system of the present invention is capable of performing more than one scheduled assay in any order in which a plurality of scheduled assays is presented. The incubated reaction mixtures are analyzed independently and individually by at least two assay procedures which are previously scheduled.

The automated continuous and random access analytical system apparatus of this invention is comprised of a front end carousel assembly inclusive of a sample cup carousel, a reagent pack carousel and a reaction vessel carousel mounted concentrically and serviced by a transfer pipetting means suitable for kitting and/or mixing reagents with a sample. The kitted and pipetted reaction vessels are transferred through a transfer station which provides means for transferring the kitted and pipetted reaction vessels to a processing work station which includes a controlled environment for maintaining temperature and provides timing for mixing of reagents and incubation. At least two assay procedural apparatus are provided which are scheduled for the various samples and kitted reagents in a unit dose disposable means for analyzing the incubated reaction mixtures. The unit dose disposable reaction vessels are removed from the process carousel by operation of the transfer station, which includes means for removing the disposable reaction vessel from the system.

In another aspect, the present invention is a device for loading a sample container onto a carousel of an automatic analytical instrument, the device including a base and a frame. The base is formed by opposing inner and outer sidewalls and closed by endwalls extending radially from the inner to the outer sidewalls. A bottom of the base is adapted for mounting the device to the carousel. The frame is connected to a top of the base by at least two legs and has a plurality of openings for receipt of the sample containers. In this manner, a sample disposed within the sample container is positioned on the carousel of the automated analytical instrument for use by the automated analytical instrument.

In a further aspect of the present invention, the device includes a means mounted within same device for supporting a bottom portion of the sample containers therein. In yet a further aspect, the means for supporting is mounted to the base of the device.

In yet a further aspect of the present invention, the segment includes a conductive sleeve which surrounds the reservoir of the sample container. The conductive sleeve facilitates signal transmission and reception for detecting the level of liquid in the reservoir by the use of RF signals.

In yet a further aspect of the present invention, the device includes a pair of slots for receiving alignment pins of the carousel. In this manner, the device holding the sample container and sample therein can be positioned at a select location on the carousel for use by the automated analytical instrument. In yet a further aspect of the present invention, one of the receiving slots is adapted to adjust for distance variations between the alignment pins.

In yet a further aspect of the present invention, a machine readable identifying code is placed on the segment. In this manner, the automated analytical system can distinguish between the various segments by the identifying code thereon.

In yet a further aspect of the present invention, the segment includes a handle. The handle facilitates handling of the segment by a user.

In another aspect, the present invention is a sample container for use with a sample container segment having a body with a reservoir and having an upper skirt surrounding an upper portion of the body for resting on a shelf of a sample container segment.

In yet a further aspect of the present invention, an identifying code is placed on the sample container. In this manner, the automated analytical system can identify the samples by distinguishing between the codes on the sample containers holding the various samples.

In yet a further aspect of the present invention, the sample container contains a conductive core which surrounds the reservoir and extends below the containment section. The conductive core facilitates sensing of the liquids in the reservoir by the use of RF signals.

Further objects and advantages of the invention will become apparent from a consideration of the following detailed descriptions and drawings.

BRIEF DESCRIPTION OF THE DRAWINGS

FIG. 5 is a top view in isolation and partial section of drive and guide elements of the front end carousel of the automated analytical system being removed.

FIG. 6 is a cross-sectional side view of a process carousel of the automated analytical system in isolation with two reaction vessels in place, one of which is in position for an FPIA read.

FIG. 7 is an isometric view of the probe, probe arm and pipettor of the automated analytical system in isolation.

FIGS. 29 and 30 represent a perspective side elevational view and partial end view of a reagent pack and reagent pack cover means for use with the automated analytical system.

FIG. 31 is a top view of a reagent pack having the reagent containers covered.

FIG. 32 taken along section A—A of FIG. 31 presents a side view in section taken along the line A—A of FIG. 31 illustrating a cover means in various open and closed positions.

FIG. 33 is an isometric view of an open reagent vessel capping means.

FIG. 34 is a perspective side elevational view of a reagent container lid opening and closing station with the reagent containers in the reagent pack having the lids opened.

FIG. 35 presents a different perspective side elevational view from that of FIG. 34 wherein the reagent containers of the reagent pack are below elements of the opening and closing station with the reagent pack lids being closed.

FIGS. 45A and 45B represent a top plan view of a reaction vessel and a side view of the reaction vessel for use with the automated analytical system, respectively, with reaction vessel compartments labeled where appropriate for FPIA processing.

FIG. 45C present an end view of the reaction vessel of FIG. 45B.

FIG. 52 is a perspective view of a heater assembly for liquid temperature control.

FIG. 53 is a cross-sectional view through the heater assembly of FIG. 52 showing the heater element within the block.

FIG. 54 is a partial cross-sectional view of the heater assembly of FIG. 52 showing liquid tubing, for example, a tubing coil within the heater assembly.

FIG. 56 is a side elevational view in section of a MEIA cartridge feeder of the automated analytical system.

DETAILED DESCRIPTION OF THE INVENTION

Figure 1:
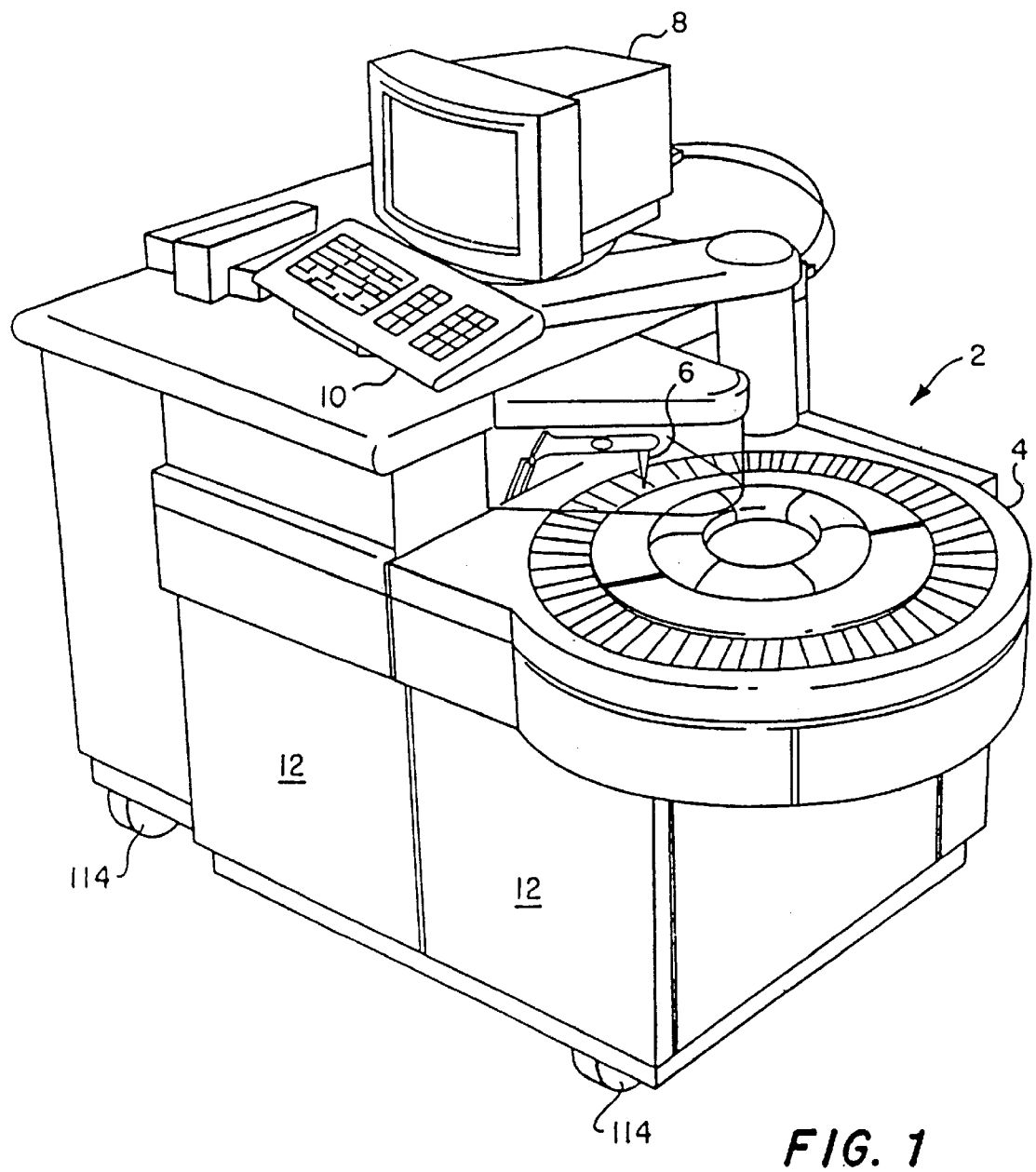
FIG. 1 is an isometric view of the automated analytical system illustrating the system cabinetry, exposed front end carousel, computer screen and keyboard.

The following description is divided into separate sections with headings to more clearly describe the invention, but should not be considered as limiting the scope of the invention.

Definitions

The following definitions are applicable to the present invention:

The term "test sample", as used herein, refers to a material suspected of containing the analyte. The test sample can be used directly as obtained from the source or following a pretreatment to modify the character of the sample. The test sample can be derived from any biological source, such as physiological fluid, including, blood, saliva, ocular lens fluid, cerebral spinal fluid, sweat, urine, milk, ascites fluid, raucous, synovial fluid, peritoneal fluid, amniotic fluid or the like. The test sample can be pretreated prior to use, such as preparing plasma from blood, diluting viscous fluids, or the like; methods of treatment can involve filtration, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte.

The term "analyte" or "analyte of interest", as used herein, refers to the compound or composition to be detected or measured and which has at least one epitope or binding site. The analyte can be any substance for which there exists a naturally occurring binding member or for which a binding member can be prepared. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), virus particles and metabolites of or antibodies to any of the above substances. The term "analyte" also includes any antigenic substances, haptens, antibodies, macromolecules and combinations thereof.

The term "analyte-analog", as used herein, refers to a substance which cross-reacts with an analyte-specific binding member, although it may do so to a greater or lesser extent than does the analyte itself. The analyte-analog can include a modified analyte as well as a fragmented or synthetic portion of the analyte molecule, so long as the analyte-analog has at least one epitopic site in common with the analyte of interest. An example of an analyte-analog is a synthetic peptide sequence which duplicates at least one epitope of the whole-molecule analyte so that the analyte-analog can bind to an analyte-specific binding member.

The term "binding member", as used herein, refers to a member of a binding pair, i.e., two different molecules wherein one of the molecules specifically binds to the second molecule through chemical or physical means. In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and basis, dyes and protein binders, peptides and specific protein binders (e.g., ribonuclease, S-peptide and ribonuclease S-protein), and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment (s) of the foregoing, as well as a preparation of such antibodies, peptides and nucleotides for which suitability for use as binding members is well known to those skilled in the art.

The term "detectable moiety", as used herein, refers to any compound or conventional detectable chemical group having a detectable physical or chemical property and which can be used to label a binding member to form a conjugate therewith. Such detectable chemical group can be, but is not intended to be limited to, enzymatically active groups such as enzymes, enzyme substrates, prosthetic groups or coenzymes; spin labels; fluorescers and fluorogens; chromophores and chromogens; luminescers such as chemiluminescers and bioluminescers; specifically bindable ligands such as biotin and avidin; electroactive species; radioisotopes; toxins, drugs, haptens; DNA; RNA; polysaccharides; polypeptides; liposomes; colored particles and colored microparticles; and the like.

The term "continuous access", as used herein, refers to the ability to add additional test samples or reagents to the automated analytical system of the present invention without the interruption of assays which are being performed by the automated analytical system of the present invention at the time of such addition.

The term "random access", as used herein, refers to the ability of the automated analytical system of the present invention to simultaneously perform more than one scheduled assay in any order in which such plurality of scheduled assays are presented into the automated analytical system of the present invention.

The term "simultaneous", as used herein, refers to the ability of the automated analytical system of the present invention to independently perform two or more scheduled assays at the same time.

The term "kitting", as used herein, refers to the ability of the automated analytical system of the present invention to create a unit dose disposable by separately transferring test samples and reagents to the reaction vessel of the present invention without initiation of an assay reaction sequence.

The term "quat" refers to a polycationic material solution for assays which use these materials which are not an antibody or antigen to capture the analyte from the sample on the matrix of, for example, MEIA cartridge. In the present inventive system, quat is dispensed to the matrix during test processing, prior to the transfer of the reaction mixture from the reaction vessel.

Detection Systems

The automated analytical system of the present invention is capable of performing various assays employing various detection systems known in the art and include, but are not intended to be limited to, spectrophotometric absorbance assay such as end-point reaction analysis and rate of reaction analysis, turbidimetric assays, nephelometric assays, radiative energy attenuation assays (such as those described in U.S. Pat. No. 4,496,293 and U.S. Pat. No. 4,743,561 and incorporated herein by reference), ion capture assays, calorimetric assays, fluorometric assays, electrochemical detection systems, potentiometric detection systems, anperometric detection systems, and immunoassays. Immunoassays include, but are not intended to be limited to, heterogeneous immunoassays such as competitive immunoassays, sandwich immunoassays, immunometric immunoassays, and the like, where the amount of a detectable moiety employed therein can be measured and correlated to the amount of analyte present in a test sample.

Generally, in a spectrophotometric assay, such as those performed on the Abbott Spectrum clinical analyzer and the Abbott Spectrum Series II clinical analyzer (Abbott Laboratories, Abbott Park, Ill., USA) the interaction in an assay solution between the analyte to be determined and a reagent system specific for the analyte produces a detectable change in the transmittive properties of the assay solution. The change in the transmittive properties refers to the amount of light absorbed or scattered by an assay solution within a particular wavelength band when a beam of light of known intensity is passed through the assay solution. The change in the transmittive properties of an assay solution is measured by passing monochromic light having a known intensity though the assay solution and determining the ratio of the intensity of the transmitted or scattered light to the intensity of the incident light. Nearly all analytes either absorb energy of a specific wavelength or interact in an assay solution with a particular reagent system to produce a detectable change in the transmittive properties of the assay solution, characteristics which have resulted in the development of numerous specific spectrophotometric assays.

Spectrophotometric assays which rely upon the measurement of the change in the transmittive properties of an assay solution as a measure of an analyte in the assay solution include, for example, assays wherein there is a change in the color of the assay when there is a change in the turbidity of the assay solution, that is, turbidimetric or nephelometric assays.

In a calorimetric assay, the change in the transmittive properties of an assay solution is generally referred to as the absorbance of the assay solution and is dependent upon the change in the color of the assay solution due to the interaction of the analyte to be determined and reagent system specific for the analyte. The absorbance of the assay solution is related to the concentration of the analyte in the assay solution. A calorimetric assay utilizes a chromogenic reagent system capable of interacting in an assay solution with the particular analyte of interest, to produce a detectable change in the transmittive properties, specifically the color, of the assay solution. Numerous chromogenic reagent systems useful in the determination of specific analytes have been developed and are commercially available.

The principle of turbidimetric assays is to determine the amount of light scattered or blocked by particulate matter as light passes through an assay solution. In a turbidimetric assay, the analyte of interest interacts with a reagent system specific for the analyte to form a suspension of particles in the assay solution. As a beam of light have a known intensity is passed through an assay solution, the suspension of particles formed by the interaction of the analyte reagent system blocks or scatters the incident light, thereby reducing the intensity of the light transmitted through the assay solution. The change of the transmittive properties in a turbidimetric assay refers to the decrease in the intensity of the light transmitted through an assay solution is related to the amount of incident light that is scattered or blocked by the suspension of particles, and depends upon the number of particles present and the cross-sectional area of such particles.

A nephelometric assay is similar to a turbidimetric assay in that the analyte of interest interacts with a reagent system specific for the ligand to form a suspension of particles in the assay solution. In a nephelometric assay, the change in the transmittive properties of the assay solution is also related to the amount of incident light scattered or blocked by the suspension of particles, but unlike turbidimetric assay wherein the intensity of the light transmitted through the assay solution is measured, the scattered or blocked light is measured at an angle to the light incident to the assay solution. Therefore, in a nephelometric assay the change in the transmittive properties refers to the difference in intensities of light incident to the assay solution and light scattered at an angle to the incident light. Turbidimetric and nephelometric assays are utilized in the analysis of blood, urine, spinal fluid, and the like, for the determination of analytes such as proteins wherein there is no comparable calorimetric assay due to the lack of an effective chromogenic reagent system. Yoe and Klimman, *Photoelectric Chemical Analysis*, Vol. II; Nephelometry, Wiley & Sons, Inc., New York, 1929, describe various nephelometric assays. various reagents and reagent systems which can be employed for performing spectrophotometric assays on the automated analytical systems of the present invention include, but are not intended to be limited to, those for the simultaneous determination of glucose and urea, such as described in U.S. Pat. No. 5,037,738 and incorporated herein by reference. The simultaneous determination of calcium and phosphorous; the simultaneous determination of cholesterol and triglycerides; determining isoenzymes; determining blood ammonia levels, and the like, can be performed on the apparatus and by the methods of the present invention.

Typically in a fluorometric assay, an analyte in an assay solution is chemically or immunologically transformed into a fluorescent complex or conjugate thereby producing a detectable change in the fluorescent properties of the assay solution. The change in the fluorescent properties of the assay solution is measured by exciting the fluorescent complex or conjugate properties produced with monochromatic light of a wavelength within the excitation wavelength band of the fluorescer, and measuring the intensity of the emitted light at a wavelength within the emission wavelength band of the fluorescer. The fluorescent intensity of the emitted light is related to the concentration of the analyte. However, the intensity of the fluorescence emitted by the assay solution may be inhibited when the ligand to be determined complexes with nonfluorescent interferences such as protein or phosphates present in the sample, or when the sample containing the ligand to be determined has sufficient color so as to act as a filter and thereby reduce the intensity of the emitted fluorescence. It is well recognized that in order to maximize the sensitivity and specificity of a fluorometric assay, these inhibiting factors, if present, must be overcome either by removal of the nonfluorescent interferences or color producing material prior to the analysis, or by compensating for the presence of such factors using an internal standard added to a second aliquot of sample and carrying out the entire assay procedure using the aliquot containing the internal standard.

Assay Formats

Generally, homogeneous and heterogeneous immunoassays depend upon the ability of a first binding member of a binding member pair to specifically bind to a second binding member of a binding member pair wherein a conjugate, comprising one of such binding members labeled with a detectable moiety, is employed to determine the extent of such binding. For example, where such binding pair members are an analyte and an antibody to such analyte, the extent of binding is determined by the amount of the detectable moiety present in the conjugate, which either has or has not participated in a binding reaction with the analyte, wherein the amount of the detectable moiety detected and measured can be correlated to the amount of analyte present in the test sample.

Homogeneous immunoassays typically are performed in a competitive immunoassay format involving a competition between an analyte from a test sample and a tracer for a limited number of receptor binding sites on an antibody to the analyte. The tracer comprises the analyte or analog thereof labeled with a detectable moiety wherein the concentration of analyte in the test sample determines the amount of the tracer that will specifically bind to the antibody. The amount of the tracer-antibody conjugate produced by such binding may be quantitatively measured and is inversely proportional to the amount of analyte present in the test sample. For example, fluorescent polarization techniques for making such determination, such as in fluorescent polarization immunoassays as described herein, are based on the principle that a fluorescently labeled compound when excited by linearly polarized light will emit fluorescence having a degree of polarization inversely related to its rate of rotation. When a molecule such as a tracer-antibody conjugate having a fluorescent label is excited with a linearly polarized fluorescent molecule it is constrained from rotating between the time light is absorbed and emitted. When a "free" tracer molecule (i.e., unbound to an antibody) is excited by linearly polarized light, its rotation is much faster than the corresponding tracer-antibody conjugate and the molecules are more randomly orientated, therefore, the emitted light is polarized. Accordingly, when plane polarized light is passed through a solution containing the aforementioned reagents, a fluorescent polarization response is detected and correlated to the amount of analyte present in the test sample.

Various fluorescent compounds which can be employed for performing fluorescent polarization assays on the automated analytical system of the present invention include, but are not intended to be limited to, aminofluoresceins, such as described in U.S. Pat. No. 4,510,251 and U.S. Pat. No. 4,614,823, incorporated herein by reference; triazinylaminofluoresceins, such as described in U.S. Pat. No. 4,420,568, and U.S. Pat. No. 4,593,089, incorporated herein by reference; carboxyfluoresceins, such as described in U.S. Pat. No. 4,668,640, incorporated herein by reference; and the like.

Heterogenous immunoassays typically involve a labeled reagent or tracer comprising an analyte, an analog of the analyte, or an antibody thereto, labeled with a detectable moiety, to form a free species and a bound species. In order to correlate the amount of tracer in one of such species to the amount of analyte present in the test sample, the free species must first be separated from the bound species, which can be accomplished according to methods known in the art employing solid phase materials for the direct immobilization of one of the binding participants in the biding reaction, such as the antibody, analyte or analog of the analyte, wherein one of the binding participants is immobilized on a solid phase material, such as a test tube, beads, particles, microparticles or the matrix of a fibrous material, and the like, according to methods known in the art.

Heterogenous immunoassays can be performed in a competitive immunoassay format as described above wherein, for example, the antibody can be immobilized to a solid phase material whereby upon separation, the amount of the tracer which is bound to such solid phase material can be detected and correlated to the amount of analyte present in the test sample. Another form of a heterogeneous immunoassay employing a solid phase material is referred to as a sandwich immunoassay, which involves contacting a test sample containing, for example, an antigen with a protein such as an antibody or another substance capable of binding the antigen, and which is immobilized on a solid phase material. The solid phase material typically is treated with a second antigen or antibody which has been labeled with a detectable moiety. The second antigen or antibody then becomes bound to the corresponding antigen or antibody on the solid phase material and, following one or more washing steps to remove any unbound material, an indicator material such as a chromogenic substance which reacts with the detectable moiety (e.g., where the detectable moiety is an enzyme, a substrate for such enzyme is added) to produce a color change. The color change is then detected and correlated to the amount of antigen or antibody present in the test sample.

For example, a heterogeneous immunoassay which can be performed by the automated analytical system of the present invention, in either a competitive or sandwich immunoassay format, is a microparticle capture enzyme immunoassay, such as that described in *Clinical Chemistry*, Volume 34, No. 9, pages 1726–1732 (1988), employing microparticles as the solid phase material.

In addition, the use of sucrose in microparticle diluent has been found to achieve neutral density of the microparticles. The methodology entails the determination of the optimum sucrose concentration which will eliminate the settling of microparticles. The sucrose concentration required to achieve neutral density is assay specific and microparticle lot specific. The principal involves dissolving sucrose in solution to increase the density of the diluent. When the density of the diluent and microparticles are equivalent, the microparticles will be in a suspended state. Density neutralization can also be achieved by using other materials such as metrizamide and/or metrizoic acid.

Separation of the bound and free species is accomplished by capture of the microparticles on a glass fiber matrix of a simple cartridge (herein, the "MEIA cartridge"), a process that relies on the high affinity of glass fibers for the microparticles, wherein the microparticles adhere to the surface of the fibers irreversibly, and nonspecifically bound material can be effectively removed by washing the matrix. The matrix also provides a precisely located mechanical support for the microparticles during the optical quantification phase of the assay protocol as described herein.

When performing a sandwich immunoassay, microparticles coated with antibody to the analyte in the test sample are incubated with the test sample containing the analyte of interest to form a capture complex with the analyte from the test sample. A conjugate comprising antibody to the analyte labeled with a detectable moiety, preferably an enzyme, is then incubated with the capture complex to form the second of a sandwich complex. When performing a competitive immunoassay, microparticles coated with antibody to the analyte in the test sample are incubated with the test sample containing the analyte of interest and a conjugate comprising the analyte or analog thereof labeled with a detectable moiety, preferably an enzyme. Removal of unbound conjugate is accomplished with the glass fiber matrix of the MEIA cartridge and, where the detectable moiety is an enzyme, a substrate for the enzyme capable of providing a detectable signal is added and the signal provided thereby is measured and correlated to the amount of analyte present in the test sample. Preferably, the enzyme-substrate system employed by the competitive and sandwich MEIA formats is alkaline phosphatase and 4-methylumbelliferyl phosphate (MUP), although other enzyme-substrate systems known in the art can be employed as well.

The MEIA cartridge which is employed by the automated analytical system of the present invention comprises a reaction well for retaining and immobilizing microparticle-analyte complexes. The reaction well has an entrance port and means for holding a quantity of sample and assay reaction mixtures positioned over a fibrous matrix which retains and immobilizes microparticle-analyte complexes as described above. The fibrous matrix is composed of fibers having an average spatial separation greater than the average diameter of the microparticles. Preferably, the average fiber spatial separation is greater than 10 microns.

The reaction well further comprises an absorbent material positioned below the fibrous matrix to enhance the flow of sample and assay reaction mixtures through the fibrous matrix. Preferably, the absorbent material is a fibrous material whose fibers predominantly lie in a plane perpendicular to the lower surface of the fibrous matrix. The absorbent matrix is in fluid communication with the fibrous matrix. Generally, the absorbent material is in physical contact with the lower surface of the fibrous matrix. The interior of the reaction well, therefore, is generally sized or contains positioning means to maintain the fluid communication between the absorbent material and the fibrous matrix. Preferably, a spike located at the bottom of the reaction well can be used to force the absorbent material into contact with the lower surface of the fibrous matrix. Additionally, it is preferable to vent to the atmosphere the gases displaced in the absorbent material by the liquids absorbed therein during the performance of an immunoassay.

According to the immunoassay methodologies described above, standard solutions of the analyte of known concentrations covering the clinical concentration range are typically prepared and assayed as is the test sample to be assayed. This blank assay provides a series of signal measurements corresponding to the known concentrations from which a standard curve is drawn. The optical signal corresponding to the unknown sample is correlated in a concentration value through interpretation from the blank or standard curve.

Analytical System Method

Automated analytical methodology for effecting analysis of a plurality of test samples according to the present invention is achieved by introducing reagent packs, test sample container and reaction vessels onto concentric carousels of a main carousel. The test sample container can be a test tube, cuvette, vacutainer tube, and the like, for holding a test sample. The reagent packs and test sample containers are identified and aligned respectively with a reaction vessel for transfer and kitting of the reaction vessel by transfer of test sample and specific reagents from the reagent pack for preparation of a predetermined test. The reaction vessel containing the test sample and one or more reagents is transferred to a process carousel wherein controlled environment conditions exist for incubation once the sample has been appropriately mixed with various-reagents to form a reaction mixture. When all assay processing steps have been completed, the reaction mixture is identified and transferred to at least, for example, one of a fluorescent polarization immunoassay reader or a microparticle enzyme immunoassay cartridge positioned on a separate cartridge wheel or carousel for further preparation before reading. The processed test samples are read and the readings are calculated with the resulting data being recorded and/or printed.

The methodology of the automated immunoassay analytical system is achieved through the use of a self-contained, fully automated, continuous and random access instrument comprising a main carousel assembly consisting of the reagent pack carousel, a reaction vessel carousel and a test sample container carousel concentrically and independently rotatable. The main carousel assembly is provided with a transfer pipette operated by a boom arm for transferring and kitting test sample and reagents into the reaction vessel automatically following a predetermined test schedule. The main carousel assembly is provided with bar code readers for reagent packs and test sample containers and has the capability of aligning the reagent pack carousel and test sample container carousel and a reaction vessel for pipette transfer operations. Once the assay to be performed is scheduled, the reaction vessel carousel, the reagent pack carousel and the test sample container carousel are rotated until the reaction vessel, a reagent pack and a test sample container, respectively, are determined to be in the transfer pipette access position. The transfer pipette then transfers the test sample from the test sample container and, depending upon the assay to be performed, the reagents from the reagent pack are transferred to the reaction vessel. The reaction vessel carousel is then rotated to a transfer station position which contacts the reaction vessel with a transfer mechanism and pulls the reaction vessel into the transfer station. The reaction vessel is then loaded onto the process carousel by the transfer mechanism.

When performing a fluorescent polarization immunoassay (FPIA) with the automated analytical system of the present invention as described in more detail below, various pipetting activities are performed by a second transfer pipette apparatus which is in service for the process carousel, and the process carousel is rotated so that the reaction vessel, when properly pipetted with, for example, FPIA reagents, is at the read station of the FPIA processing stations and the FPIA determination on reading, is made on the reaction vessel. The process carousel is then rotated so that the read reaction vessel is at the transfer station. The reaction vessel is again contacted and transferred by the transfer station. The transfer station is rotated and pushes the reaction vessel into a release container opening.

For a microparticle enzyme immunoassay (MEIA) performed with the automated analytical system of the present invention as describe din more detail below, after the various pipetting activities for the MEIA, which can be completed at the main carousel assembly, the reaction vessel is transferred to the process carousel as described in the FPIA process. Pipetting can also be accomplished in the process carousel or jointly between the two carousels. To complete the MEIA, the reaction mixture is transferred from the reaction vessel to a matrix of an MEIA cartridge on a cartridge carousel with the second transfer pipette. The matrix is washed with a buffer and a substrate, such as MUP (defined earlier), or other suitable substrate known in the art. The cartridge carousel is then rotated so that the MEIA cartridge is positioned at an MEIA processing assembly and the MEIA determination is made. The MEIA reaction vessel is ejected into the waste container as described for the FPIA reaction vessel. The MEIA cartridge is independently ejected from the cartridge wheel by an ejector at an appropriate ejector station into a waste container.

Preferably, two distinct analytical technologies as described above, FPIA and MEIA, are incorporated into the automated analytical system of the present invention; however, more than two distinct analytical technologies can be incorporated into the inventive system. These methods are complimentary and share a commonality of apparatus and procedural steps, with the FPIA generally being the method of choice for analytes of low molecular weight and MEIA for molecules such as protein hormones, antibodies or analytes of low molecular weight requiring higher sensitivity. The two technologies share system components including the operator control panel, pipetting boom assemblies, fluidics systems, air and liquid reagent heaters, printers, bar code reader and stepper motors. Such commonality of use of system components allows for a compact instrument despite the dual FPIA and MEIA capability.

The FPIA optic systems (such as described in U.S. Pat. No. 4,269,511 and incorporated herein by reference) can utilize a polarizing filter which is an electrically switched liquid crystal, maintaining a compact size and avoiding complex and potentially unreliable moving parts. When performing FPIA assays utilizing the automated analytical system of the present invention, the FPIA reagent packs will typically include a tracer comprising the analyte or analog thereof, coupled to a detectable moiety, an antibody specific to that analyte, and a specimen pretreatment reagent. In a preferred FPIA format, the analyte being determined competes with the tracer for a limited number of binding sites on the antibodies specific to the portion or portions of the analyte and tracer. The detectable moiety component of the tracer is preferably a fluorescent moiety selected from the group consisting of fluoresceins, aminofluoresceins, carboxyfluoresceins, fluoresceinamines, and the like, more preferably carboxymethyl-aminomethyl-fluorescein, carboxyethylaminomethyl-carboxyfluorescein, 6-carboxyfluorescein, 5-carboxyfluorescein, succinylanimomethyl-fluorescein, thiourea-aminofluorescein, methoxytrianolylaminofluorescein, aminofluorescein, and the like.

In another embodiment, the FPIA format utilizes a unique, round, plastic, reaction cuvette suitable for fluorescence polarization and absorbance assay technologies which require no orientation other than top-to-bottom. This plastic reaction cuvette has physical characteristics of low birefringence throughout the optical read region as well as stringent dimensional tolerances which allow reproducible absorbance readings. Bifringence is defined as the degree of retardation of the extraordinary ray as it passes through a material. The greater the degree of retardation, the greater will be the level of birefringence. Retardation of the extraordinary ray is dependent on the magnitude and direction of the induced stress. Therefore, passing a ray of linearly polarized light through a material with induced stress will result in depolarization of the ray. In order for a cuvette to be utilized for fluorescence polarization measurements, it is important that the cuvette be prepared under conditions which yield minimum stress. The geometry of the cuvette has been designed to utilize the inherent fluidics of automated medical diagnostic instrumentation to minimize the hydrophobic effect of plastic.

MEIA results can be determined by quantifying the rate of fluorescence developed when fluorogenic substrate is converted by the action of an enzyme labeled conjugate. For example, when performing either a competitive MEIA or sandwich MEIA, the specifically bound alkaline phosphatase on the microparticles is detected by addition of the fluorogenic substrate MUP to the matrix. The alkaline phosphatase catalyzes hydrolysis of the MUP to inorganic phosphate and fluorescent 4-methylumbelliferone (4-MU). The liberated 4-mu is detected by the MEIA optics assembly front surface fluorometer which is designed to detect fluorescence of low concentrations of 4-MU without interference by fluorescence of 4-MUP at a wavelength of 367. A system of lenses and optical filters focus filtered light (wavelength=365) from a mercury arc lamp on to the surface of the matrix and focus emitted fluorescence from 4-MU (wavelength=448) on to a photo multiplier tube. Like the FPIA optics assembly, the MEIA optics system is compact and has no moving parts. About five percent of the excitation light is detected by a photodiode, allowing normalization of the fluorescence data and generation of a control signal used by the lamp power supply to maintain the intensity of the excitation light within five percent over the useful life of the lamp. The MEIA post-processor uses linear regression analysis to convert the data from multiple successive determinations of 4-MU fluorescence to a rate which is proportional to the concentration of alkaline phosphatase conjugate specifically bound to the microparticles.

MEIA formats can be run with a multi-position MEIA auxiliary carousel and process carousel as well as a MEIA reagent pack containing microparticle reagent, an alkaline phosphatase conjugate and, in some cases, a dilute buffer specific for the assay being performed. Because the microparticles tend not to settle out of suspension during the course of the assay, they can readily be pipetted. The effective surface area of polystyrene latex microparticles is several fold greater than that of a large diameter polystyrene bead (e.g., one quarter inch beads) commonly used in commercial immunoassays. Because of this large surface area and the very small diffusion distance between analyte and the capture molecules on the surface of the microparticles, the capture phase employed in many of the MEIA methods being performed reaches equilibrium within several minutes, allowing for a full carousel of test samples to be completed in a very short time frame.

Unlike an FPIA, the heterogeneous immunoassays, such as a MEIA, require a separation step as described above. In particular, after incubation of the microparticles with a test sample, the microparticles are separated from the reaction mixture by transfer to the matrix contained in the MEIA cartridge as described above. The matrix provides a precisely located mechanical support for the microparticles during the subsequent optical read phase- of the assay. This precisely located mechanical support, i.e. the cartridge, is fit into the auxiliary carousel at a predetermined spacing from the reader apparatus by camming means.

ANALYTICAL SYSTEM APPARATUS

The automated immunoassay analytical system according to the present invention (hereinafter the "analytical system"

or "system") is both continuous and random access. The following description of the analytical system includes a general description of sufficient scope for those skilled in the relevant arts, followed by more detailed descriptions of critical components and subsystems unique to the system. The drawings do not illustrate all of the mechanical and electrical elements for driving and controlling the various components of the system, because the structure and operation of such omitted elements are know to those of ordinary skill in the art who having knowledge of the information provided herein would understand the operation of the system and the various components and related processes utilized for treating samples and determining analytical results.

Figure 2:
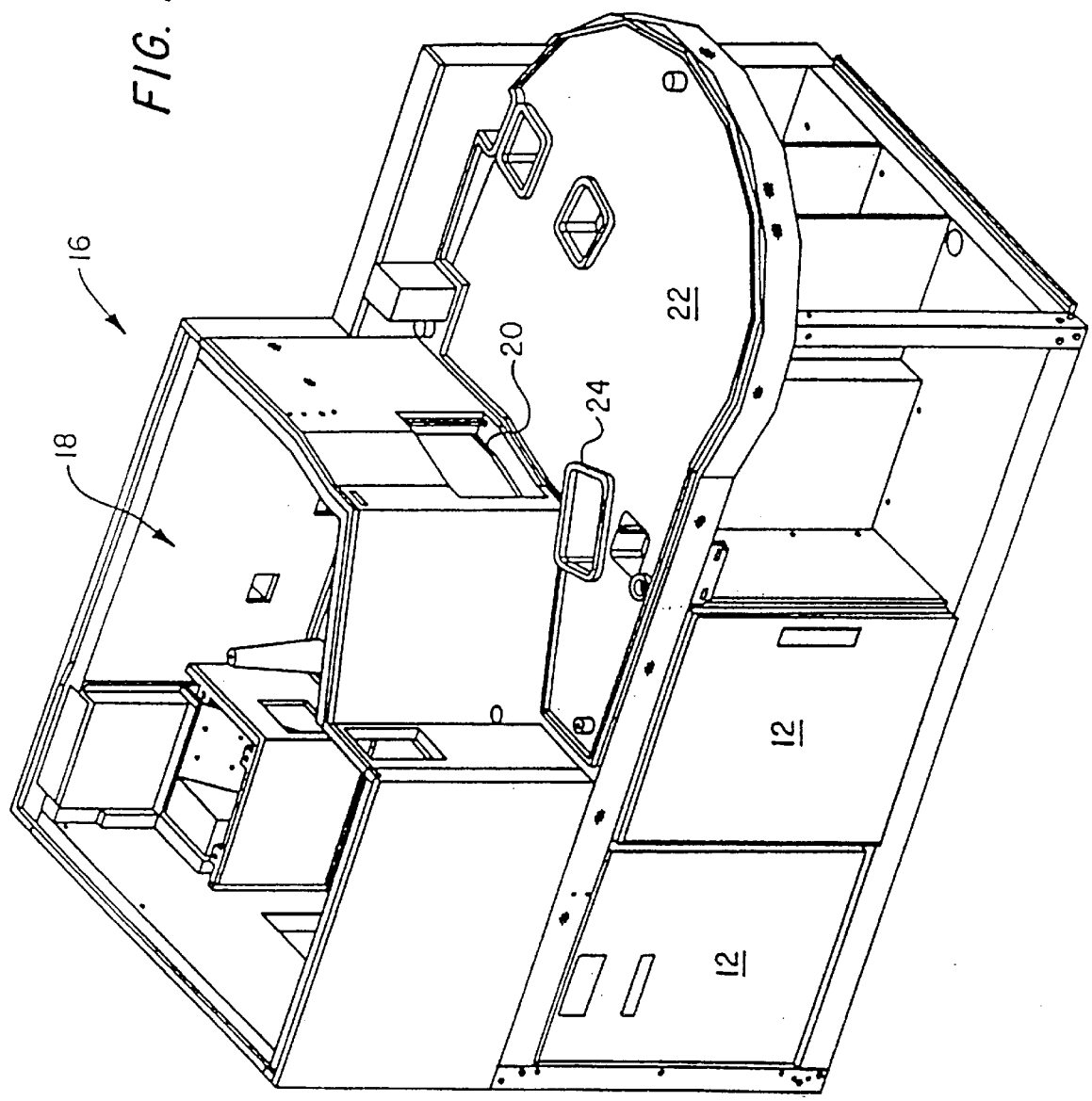
FIG. 2 is an isometric view of the automated analytical system apparatus frame and cabinet.

Referring to the drawings, FIGS. 1 and 2 present isometric views of the apparatus for the automatic immunoassay analytical system of the present invention. The system apparatus as it appears in FIG. 1 presents the system apparatus as used by the technician, with FIG. 2 illustrating an isometric view of the frame and cabinetry with component parts removed. The system apparatus of the present invention is identified generally as 2 in FIG. 1. The system apparatus 2 has an exposed front end carousel 4 which is serviced by a first transfer pipette mechanism 6 for kitting scheduled tests along with samples into a reaction vessel. The system provides a computer screen 8 and computer keyboard 10 along with access panels 12 for accessing storage and waste compartments. The system apparatus 2 is provided with rollers 14 for movement of the system apparatus within a laboratory complex as required. The freedom of movement of the system apparatus through rollers 14 is allowed since the system is fully self-contained but for power requirements.

Referring to FIG. 2, the system apparatus 2 cabinet frame 16 is illustrated with substantially all functioning components of the system apparatus removed. A controlled environment zone 18 is a closed unit during operation with light shielding and rigid control of airflow as well as temperature as opposed to the open front end carousel 4. The front end carousel 4 communicates with the controlled environment zone 18 through a transfer port 20. The front end carousel 4 is mounted to an aluminum base plate which rests on a support platform 22 and the first transfer pipette mechanism is mounted on means 24.

Figure 3:
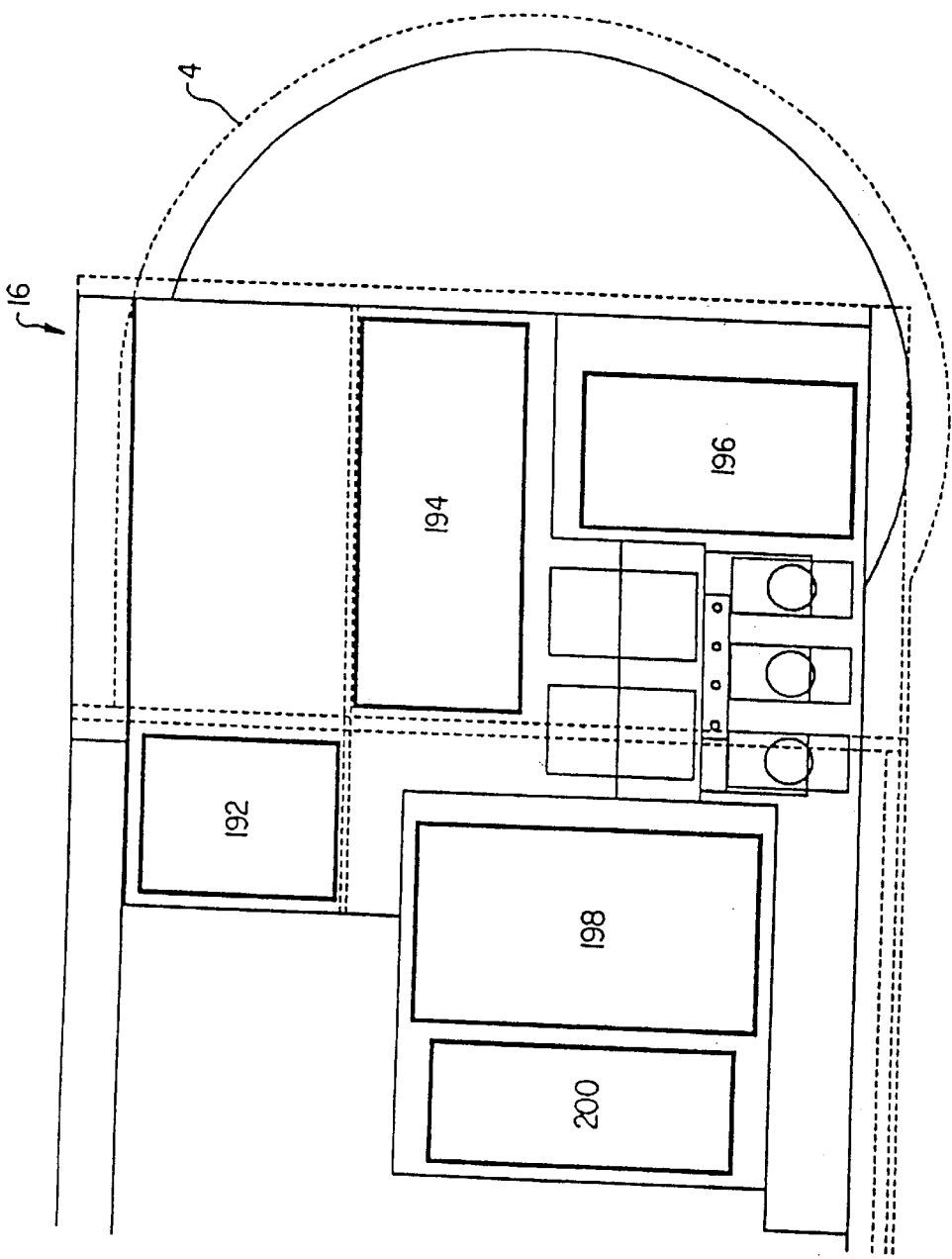
FIG. 3 is a top plan view in section of the lower cabinet of FIGS. 1 and 2 illustrating water and/or buffer supply station as well as liquid and solid waster containers of the automated analytical system.

Referring to FIG. 3, the top plan view of the system apparatus 2 shows a portion of the cabinet frame 16 and the front end carousel 4 in partial phantom. This portion of the cabinet 16 also supports a power supply 192, a supply bottle 196, a solid waste container 198, and a liquid waste container 200. The supply bottle 196 provides buffers for the tests being performed, while the containers 198 and 200 provide storage for the processed waste material.

Figure 4A:
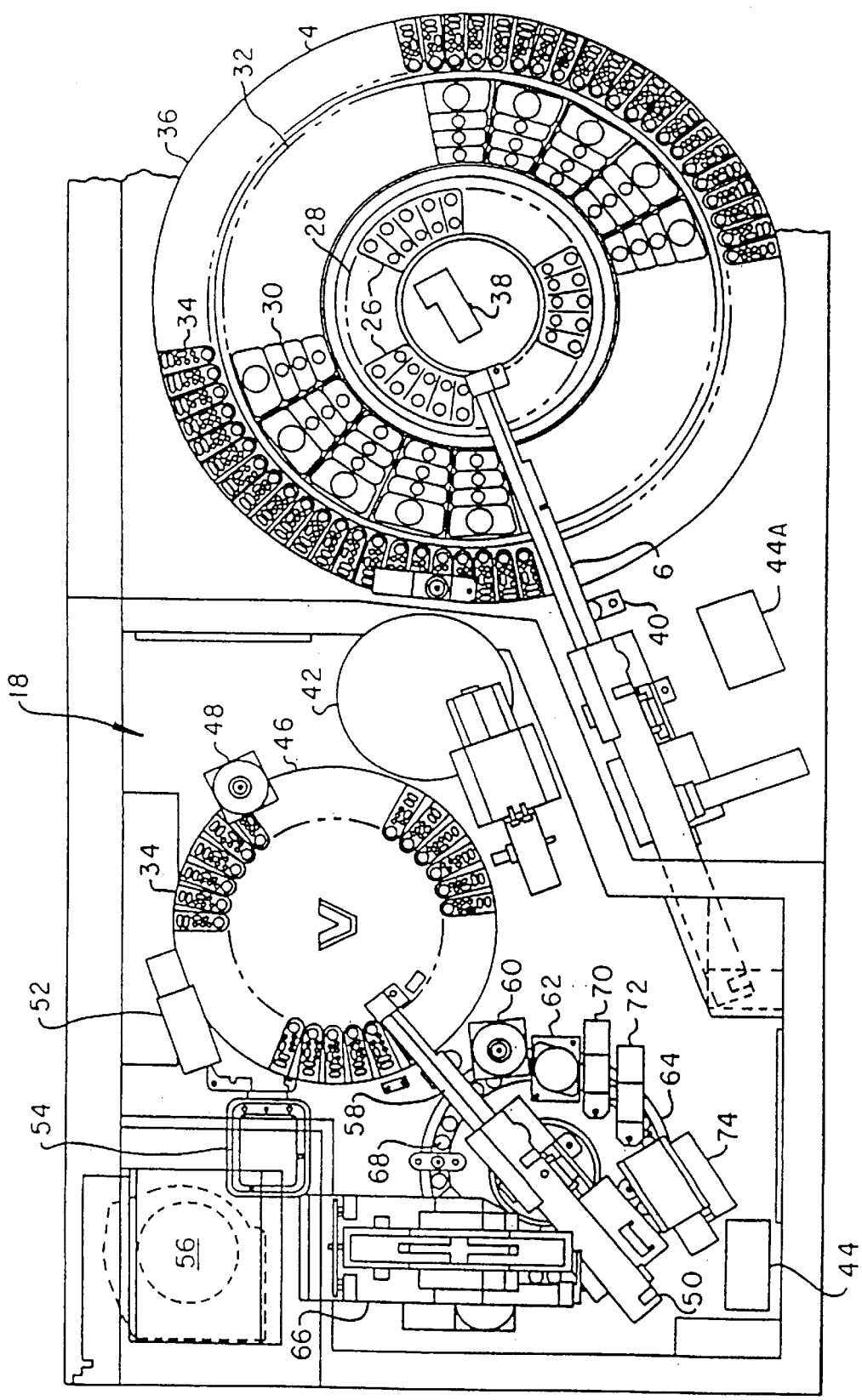
FIG. 4A is a top plan view of the automated analytical system in section with component covers removed to show the automated analytical system apparatus in detail and relative position.
Figure 4B:
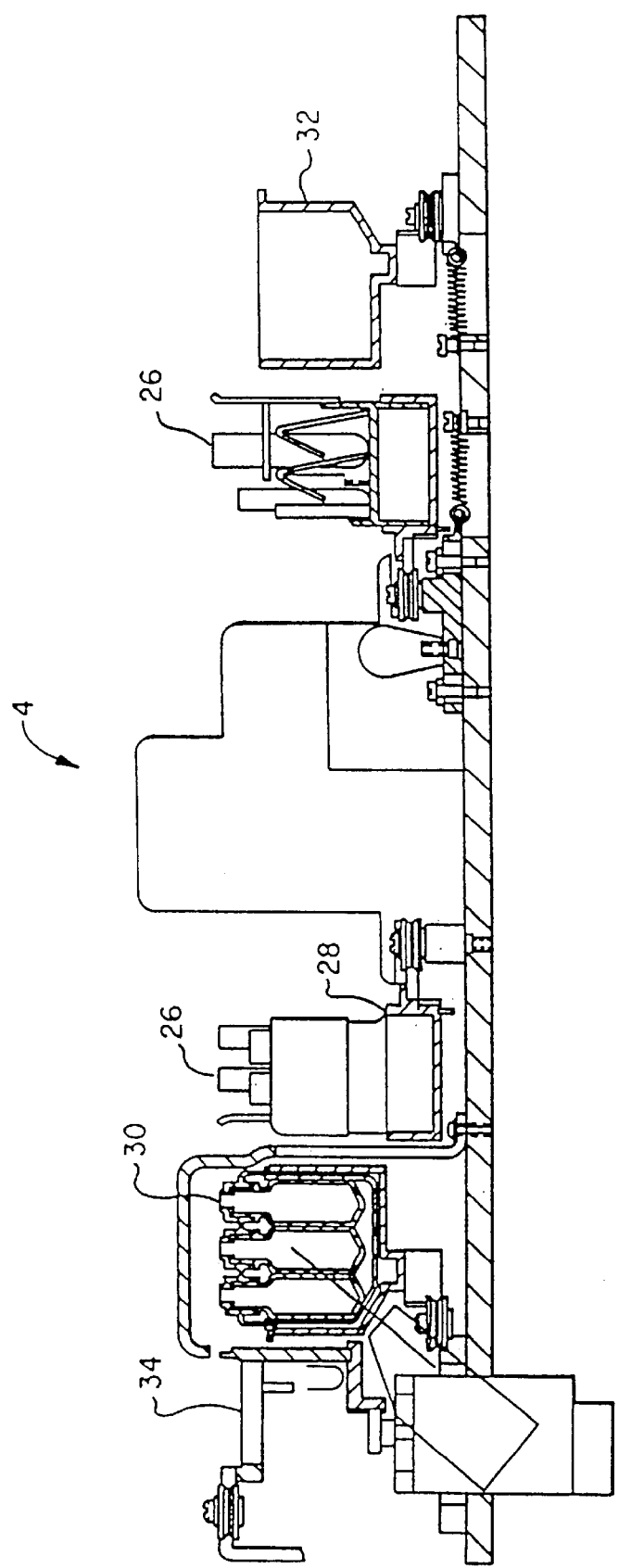
FIG. 4B is a front elevational view of the automated analytical system in isolation and partial section of elements of the front end carousel.

Referring to FIGS. 4A and 4B, components of the system apparatus are shown in more detail with relative positioning to further illustrate the process flow of the system apparatus. For example, sample cups 26 are mounted on a sample cup carousel 28 which is concentrically fitted within the front end carousel 4 along with reagent pack carousel 32 and reaction vessel carousel 36. The reagent pack carousel 32 is concentrically fitted between the sample cup carousel 28 and the reaction vessel carouse 36. The reagent pack carousel carries reagent packs 30 and the reaction vessel carousel 36 carries reaction vessels 34. The front end carousel 4 inclusive of the three front end carousels, the sample cup carousel 28, reagent pack carousel 32 and reaction vessel carousel 36 can be example contain the following capacities. The sample cup carousel 28 can hold 60 blood collection tubes, such as Vacutainer® blood collection tubes, or 90 sample cups which are injection molded as one piece and can be provided with standalone base mounts. Standalone base mounts are suitable for technician handling and pipetting of samples into the sample cups. The reagent pack carousel 32 provides for 20 different reagent packs 30. The reaction vessel carousel 36 provides 90 reaction vessels 34.

The front end carousel 4 has an operable bar code reader 38 for automatically identifying reagent pack carousel 32 and sample carousel 28. A wash cup 40 is provided for the first transfer pipette mechanism 6 for washing as required between transfer of various sample and reagents. The first transfer pipette mechanism 6 is utilized in kitting the various reagent pack liquid materials and sample into a reaction vessel 34. The reagents and the sample are properly kitted through means of the first transfer pipette mechanism 6 inclusive of pump means. The various carousels are rotated and aligned for kitting at the pipetting station. The kitted reaction vessel 34 is positioned by reaction vessel carousel 36 into the proper position for transfer to the transfer station 42. The reaction vessel 34 is transferred to the transfer station 42 through transfer means described below in more detail below (FIG. 9) wherein the transfer station 42 is then rotated to move the reaction vessel onto process carousel 46.

As shown, the process carousel 46 is driven by a stepper motor 48 and is serviced by a second transfer pipette mechanism 50. The process carousel 46 supported by three wheels for height control and control of any radial movement caused by irregularly shaped carousel elements. Both the FPIA and MEIA procedures utilize the system apparatus commonly up through and including the process carousel 46. The process carousel 46 includes FPIA processing 52 and FPIA processing lamp 54 for direct reading of FPIA analysis of kitted, pipetted and properly reacted reagents sample from the reaction vessel 34. The process carousel 46 holds, for example, 36 reaction vessels 34 and has a carousel diameter of about 12.5 inches. The process carousel 46 moves the reaction vessels 34 between the transfer station 42, the second transfer pipettor mechanism 50, the point of pipetting, and the FPIA reader processing 52. The controlled environment zone 18, which includes the transfer station 42 and process carousel 46, provides FPIA processing with air circulation under temperature control by cabinet air circulation fan 56. A wash cup 58 for the second transfer pipette mechanism 50 is provided. The second transfer pipette 50 is utilized for adding reagents (pipetting) under conditions of incubation and timing to the sample in the FPIA test schedule reaction vessel 34 for FPIA process.

MEIA processing can also utilize the second transfer pipette 50 for adding reagents to the sample before the reaction mix is added to MEIA cartridges 68 which are mounted on the auxiliary carousel 64, also referred to as the cartridge wheel carousel. The MEIA reagent mixed sample is transferred to the MEIA cartridge 68 by the second transfer pipette 50. The second transfer pipette 50 moves the pipette probe between the wells in the reaction vessel 34 on the process carousel 46 to the MEIA cartridge 68 on the auxiliary carousel 64 and to the wash cup 58. A rack-and-pinion drive through two axis stepper motor drives achieves precision drive on both the R and Z axis. Travel, for example, on the Z axis can be about 3 inches and on the R axis about 4.5 to 5.0 inches.

The auxiliary carousel 64 holds, for example, 32 MEIA cartridges 68 and has a diameter of about 9.5 inches. The auxiliary carousel 64 moves the MEIA cartridges 68 between various stations including the second transfer pipettor mechanism pipette point, the MUP dispense station 72, the MEIA washstation 70 and the MEIA reader 74 and the MEIA cartridge ejection point 62. The auxiliary carousel 64 is stepper motor driven and is carried by three wheels with one wheel located at the Z axis height control at the cartridge insertion point, the second wheel at the pipette point, and the third wheel at the MEIA reader in order to maintain the auxiliary carousel 64 within desired geometric relationships to these various functions.

MEIA cartridges 68 are loaded into a cartridge hopper 590 which feeds the MEIA cartridges 68 into the auxiliary carousel 64. The automatic feeding of the MEIA cartridges 68 is provided with a proper height adjustment of the cartridge 68 into the auxiliary carousel 64 as required by MEIA reading. The cartridge hopper 590 feeds individual cartridges 68 to the auxiliary carousel 64 and changes the axis of orientation of the cartridge 68 from horizontal to vertical by automatic means. Removal of the MEIA cartridges 68 is achieved through the use of an ejector 62 which operates through an ejection rod and forces the MEIA cartridge 68 from the auxiliary carousel 64 which is dropped into the solid waste container 200 (FIG. 3). the auxiliary carousel 64 is further serviced by a MEIA buffer heater and disperser 70, MUP heater and dispenser probe 72, and MEIA reader 74. The MEIA cartridges 68 are removed from the auxiliary carousel 64 by a cartridge ejector 62 after the MEIA read has been completed.

FIG. 5 provides a top view in isolation and partial section of elements of the drive and guide systems of the main carousel 4 with the various carousels removed. In FIG. 5 a sample cup carousel stepper motor 76 is shown mounted with mounting spring 78. The reagent pack carousel motor 80 is also shown with a mounting spring 82. The reaction vessel carousel motor 84 and mounting spring 86 are positioned to the exterior of the two inner carousels, i.e. The sample cups carousel 28 and the reagent pack carousel 32. Roller guides 88 are provided for the sample cup carousel 28 and a tensioning spring 90. The reagent pack carousel is provided with roller guides 92 and tensioning means 94. The reaction vessel roller guides 96 are also provided with spring elements 98, the purposes of the guide and these various spring elements being to maintain very finite tracking of the concentric carousels when motivated by the individual stepper motors.

Motion control for the system 2 is performed by 22 stepper motors of various sizes, some of which are identified herein. The specifications and operation of the stepper motors are described generally as follows, such description being sufficient for one skilled in the art. All the stepper motors are permanent magnet motors with 200 full steps per shaft revolution which is equivalent to 1.8 degrees revolution per step. A single stepping motor control system comprises the following:
(1) A step motor connected to a mechanism to move the mechanism as required.
(2) A drive which applies voltages to the step motor causing it to move in response to 3 control signals from control electronics, i.e., an "Indexer".
(3) An indexer which comprises electronics for controlling the motor by the driver. It determines move profiles, which include direction of rotation, number of steps to move and acceleration and velocity parameters.
(4) A home sensor is used for each step motor. The home sensor is used as a position reference by the Indexer and can also be used by the Indexer to check for errors.
(5) Encoders are used by the rotary devices, the carousels and transfer mechanism to verify correct movement. At the end of a move, the encoder count is checked to validate that the motor moved to the correct position.

The system microprocessor (CPU) is used to determine the distance, velocity and acceleration of a motor movement of the steppers. It transfers the information to the Indexer which then controls the movement. At the end of the movement, the Indexer then signals the system microprocessor (CPU) that the movement is complete. The system microprocessor (CPU) then checks the encoders to validate the movement if a rotary mechanism was being moved and checks the Indexer to verify it had detected no errors.

There are three indexer boards in each system 2. Each board is identical and can control up to eight stepper motor. Each board utilizes one slave microprocessor to provide the eight indexer functions on each board. Such a combination of unctions is referred to as an "8-axis" indexer. Two of the indexer axes are not used. The indexer boards communicate to the system microprocessor (CPU) over a backplane VME bus. The Indexers have addresses that are modified by jumpers before installation into the system. This is the mechanism that allows otherwise identical boards to reside in the same system backplane VME bus. Each board is connected via the VME backplane bus to one cable per board that carries the indexer signals to the drivers. The indexer provides a variety of movement profiles. Many of the step motor movements required that the speed of the motor be increased in a controlled fashion until the final velocity is reached. At some point in the movement, the speed must then be decreased in a controlled fashion. This process is called a "velocity profile" and can be done linearly, sinusoidally, or parabolically. The type of velocity profile executed is determined by the system microprocessor (CPU). The Indexers are available from vendors as "off the shelf" 8-axis indexers.

There are three PC boards used to provide the 22 separate motor drive circuits. Two of the boards are identical and referred to as the "Stepper Drive" boards. Each of the Stepper Drive boards comprises eight functionally identical stepper driver circuits. They differ only in the current levels applied to each stepper motor. The current is controlled by a separate resistor in each driver circuit. The third board is called a "Power I/O" board because it contains seven motor driver circuits and eight solenoid driver circuits. A single driver receives the following three inputs from an Indexer which controls its outputs to the step motor:
(1) Step input—for each step pulse input, the step motor will be moved one step,
(2) Direction input—constant level signal which controls the direction of motor rotation,
(3) Power Hi input—logic level input which causes the driver to apply maximum power to the step motor during movement. When Power Hi is not asserted, a lower power level is applied to the step motor to reduce heat and to reduce system power consumption when the motor is not being moved.

Each driver circuit has a pair of current setting resistors to set motor current level for Power High and to set a different motor current level when Power High is not asserted. There are two pairs of current setting resistors for each driver circuit. Additionally, each board has logic used to identify the position of the board in the card cage. There are two pins in the power backplane connectors which are used to encode each connector slot for the three boards that drive motors. By grounding or leaving unconnected, four combinations of two pins are possible. The board logic decodes the connector position and, through FET switches, each driver circuit than connects the correct pair of current setting resistors. The board output is only enabled if the Stepper Drive is plugged into one of the two connectors allocated for Stepper Drive boards. Each stepper drive circuit is known in the industry and available from most circuit vendors. The circuit is known as a "Bipolar chopper half-step driver". Although there are 200 "full steps" per shaft revolution, the motor can be driven in such a way as to cause the shaft to stop midway between the "full step" position. It can of course also stop at the "full step" positions, which provides a total of 400 steps per shaft revolution. This adds to the resolution of the moving mechanism and aids in reducing motor induced vibration.

The Power I/O board includes the seven stepper drive circuits and eight solenoid drivers as indicated above. Six of the stepper driver circuits are identical in function to those of the Stepper Drive boards. The seventh is functionally the same except that it is provided with less heat sink and therefore is limited to driving lower power motors. This circuit is used to drive the small ejector 62. There is only one pair of current setting resistors per driver circuit since there is only one Power I/O per system. Position decoding logic on the Power I/O enables outputs only when it is plugged into the connector designated for the Power I/O board.

The Home Sensors are fed into the Indexers and the Encoder circuits are fed into a VME general purpose board which provides counters for counting the encoder pulses and which also makes the counters available to the system microprocessor (CPU). At the beginning of a move, the system microprocessor (CPU) sets the appropriate encoder counter to zero. It then commands an Indexer to move the corresponding stepper motor the required number of steps. At the end of the move the system microprocessor (CPU) checks the encoder counter to verify that the motor did move the correct number of steps. There is a "window" of acceptability, such that the counter can be off by a few counts. If the counter is off by more than the permissible number of counts, an error is declared by the system microprocessor (CPU) and appropriate action is then taken by the system microprocessor (CPU).

The Power I/O board provides "chopper drives" to control various solenoid valves in the system. The system microprocessor (CPU) sets a bit of one of the digital I/O boards to energize a valve. The bit is optically coupled to the Power I/O solenoid drive circuit. The solenoid drive circuit then provides a 36 V turn on voltage for approximately 300 msec, after which the voltage is lowered to about 27 volts to reduce power dissipation and solenoid temperature rise. The lower voltage is achieved by applying the 36 V in a chopped fashion such that the time average is about 27 volts, although the actual waveform is comprised only of 36 V and ground signal levels. This is also known as pulse width modulation.

Referring to FIG. 6, the process carousel 46 is shown in an isolational cross-sectional side view. One reaction vessel 34 is at rest or nonoperative position and a second reaction vessel 34 is in position for FPIA read. The process carousel 46 is capable of bidirectional motion for timely movement of the various reaction vessels 34 to pipettor action, read, or transfer to and from the carousel. Up to about 36 or more reaction vessels 34 can be processed at one time on the process carousel 46 depending on diameter and sizing of the reaction vessels 34.

Referring now to FIG. 7, the first transfer pipette mechanism 6 shown in more detail includes a transfer pipette Z axis motor 102 which moves the probe arm 104, probe 106 and probe tip 108 in a vertical direction while transfer pipette R axis motor 100 drives the probe arm 104, probe adjustment means 106 and probe tip 108 in a horizontal motion. The first transfer pipette mechanism 6, sometimes labeled "Sample Probe Arm Mechanism", moves the probe between the sample cup 26, the reagent pack 30, the reaction vessel 34 and the wash cup 40. The wash cup 40 is used to wash the interior and exterior surfaces of the first transfer pipettor mechanism 6 probe. The drive of the first transfer pipette mechanism is a rack-and-pinion drive means along the Z and R axis by two-stepper motor drivers. A brake is provided to hold the Z axis position when power is lost, thus avoiding damage to the system apparatus. For example, the first transfer pipette mechanism can be designed to have a Z axis travel of about 3 inches and an R axis travel of about 11½ inches.

Figure 8:
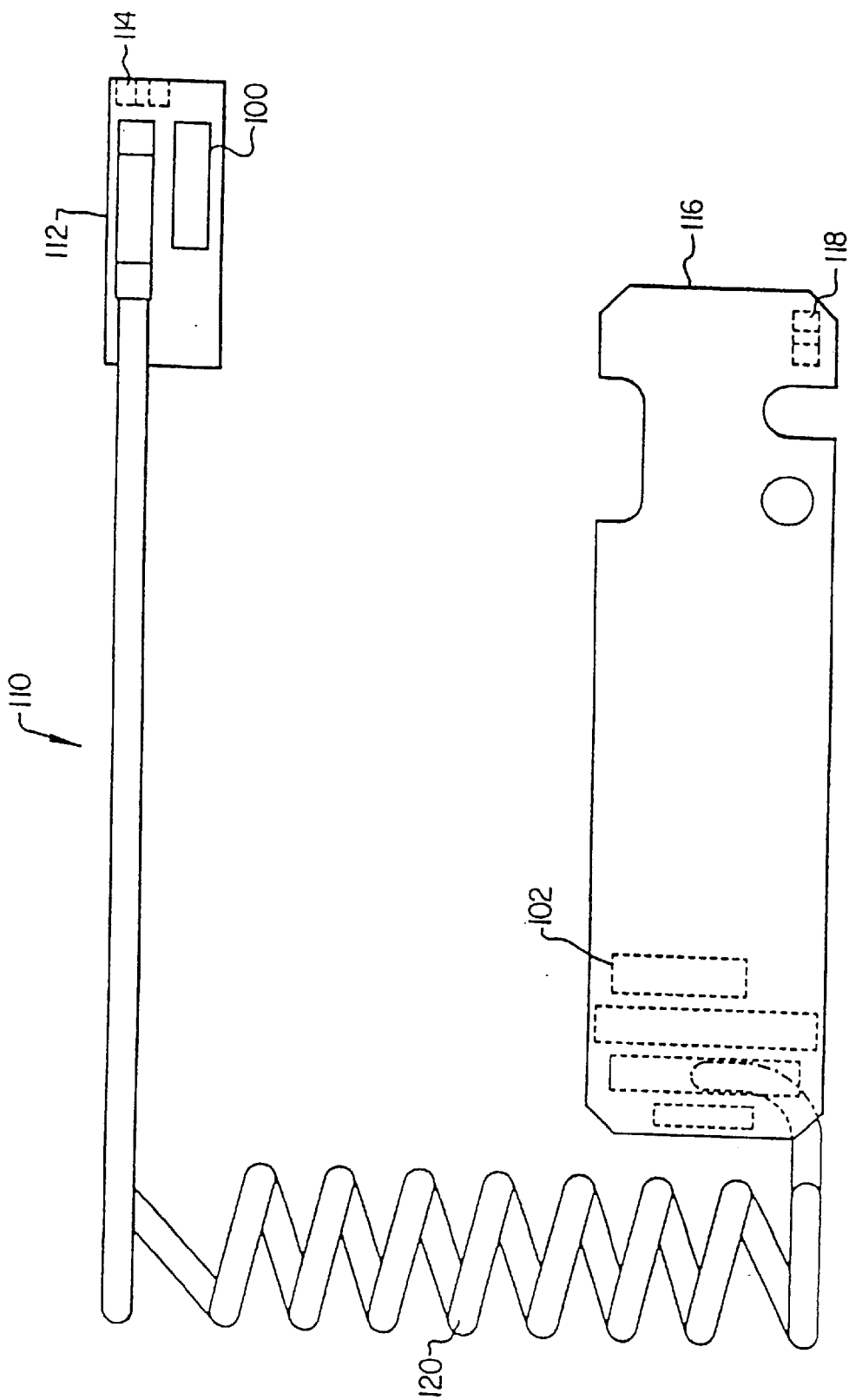
FIG. 8 is a schematic side view of the probe arm wiring and sensor means of the automated analytical system.

The first transfer pipette mechanism 6 and the second transfer pipette mechanism 50 are closely related in general system apparatus function and design, with variation on travel and size being the only substantial differences. Both units have a probe arm circuit 110 as illustrated by the schematic side view of FIG. 8. The schematic illustrates the R axis motor 100 and the Z axis motor 102 in relationship to an upper PCB 112 and a R axis home sensor 114. A lower PCB 116 is illustrated in relationship to the Z axis home sensor 118 with a coil cable 120 connecting the various elements.

Figure 9A:
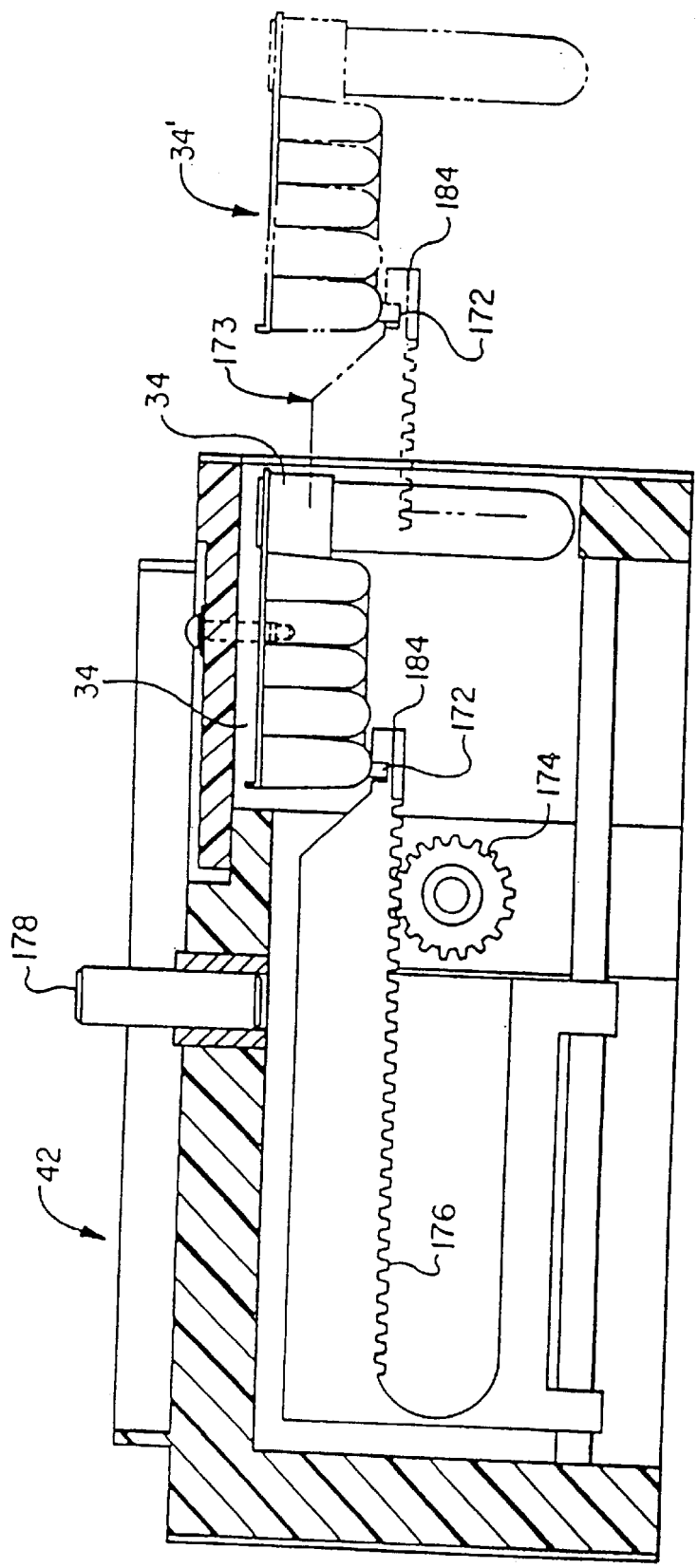
FIG. 9A is a sectional side view of the transfer element of the automated analytical system engaging a reaction vessel for transfer from the main carousel into the transfer station.
Figure 9B:
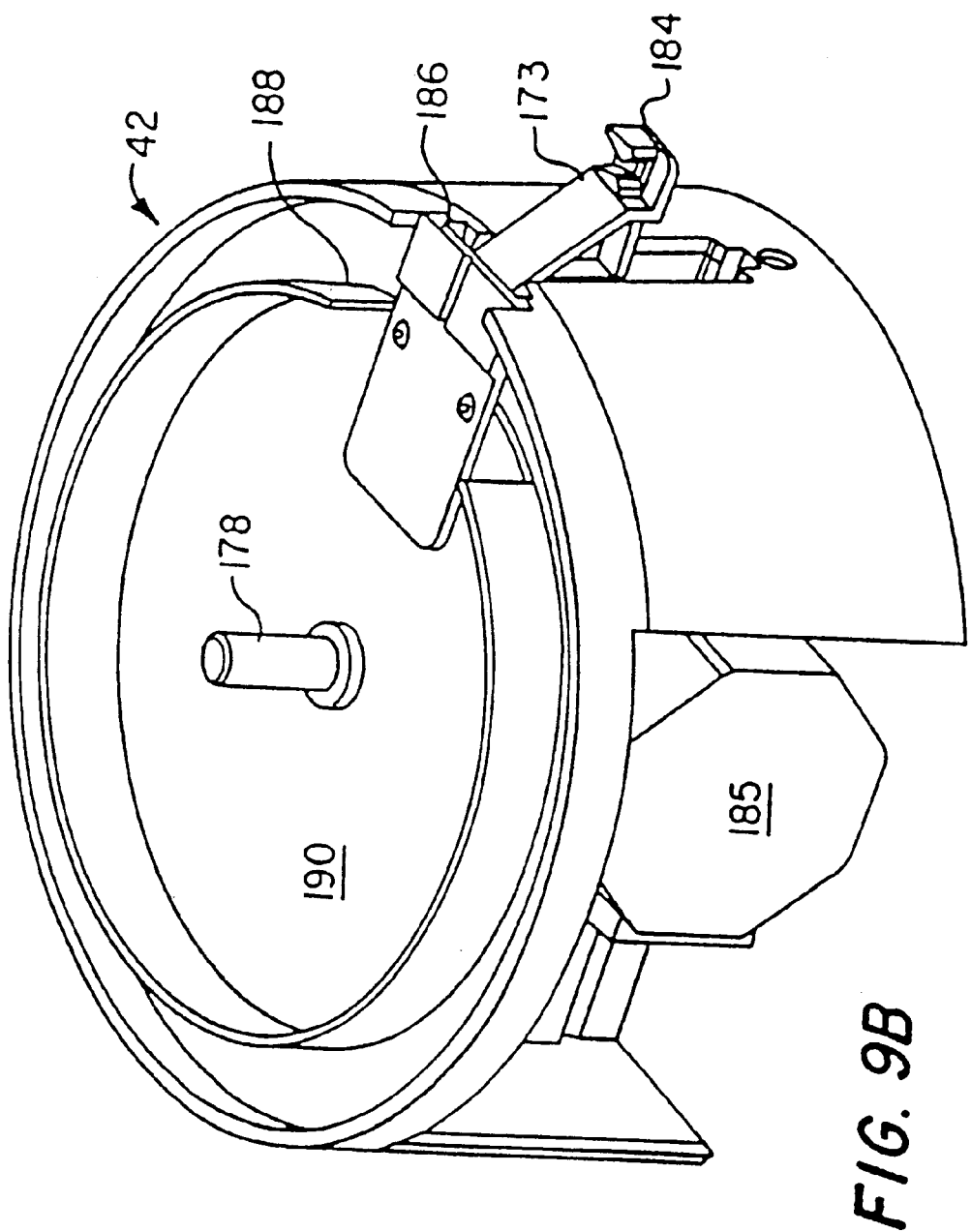
FIG. 9B is a perspective side elevational view of the transfer station of the automated analytical system.

The transfer station 42 plays a key role in apparatus and process function. Referring to FIGS. 9A and 9B, the transfer element at the transfer station 42 is shown engaging reaction vessel 34 by means of a reaction vessel transfer projection 172. The transfer arm 173 is projected out between reaction vessel elements of the reaction vessel carousel 36 and, by rotation of the transfer station 42, engages the reaction vessel transfer projection 172. By means of a transfer arm drive gear 174, the transfer arm 173 rack gear 176 moves the transfer arm 173 out and in relationship to the transfer station 42. The transfer station 42 has a rotation axis 178. A reaction vessel 34', shown in phantom, is shown as mounted on the front end carousel 4, reaction vessel carousel 36 being engaged by the transfer arm 173 by means of reaction vessel transfer projection 172. The reaction vessel 34' has a transfer handling means, i.e. transfer projection 172 which allows the transfer arm 173 of the transfer carousel to position an engagement means or pick 184 for engaging the reaction vessel 34' transfer projection 172. The reaction vessel 34 is illustrated onboard the transfer station by reaction transfer station 42 which moves the reaction vessel 34 between the front end carousel 4 and the process carousel 46. The transfer station 42 moves the discarded reaction vessel 34 from the process carousel 46 to the waste ejection station (not shown). The transfer station 42 is driven by a stepper motor drive and is supported by precision linear ball bearings and axis of rotation ball bearings.

SCHEDULING OPERATION OF THE SYSTEM

According to the present invention, the analytical system 2 is controlled by software executed by the system microprocessor (CPU) which also executes application software for generating and optimizing the tests being run on the analytical system 2 (hereinafter the "scheduler"). The scheduler schedules the activities of assays that have been modelled by using a flexible protocol technology which enables the scheduler to minimize components of the analytical system 2, i.e., the resources, remain idle by properly sequencing the activities which comprise the assay. These activities can be, for example, pipetting (P), optical or other types of readings (R), cartridge washings (W), and MUP dispensing (D), all of which are accomplished using the system's resources. The resources according to preferred embodiment of the analytical system 2 include the primary carousel 46, the auxiliary carousel 64, and the process pipettor 50. Generally, an activity uses only one resource, i.e., a reading (R), washing (W), or dispensing (D) at one station of a carousel. However, the pipetting (P) uses more than one resource, i.e., the pipettor 50 and one or both of the carousels 46, 64. The flexible protocol technology is developmental software used by a chemist to model assays, such as the FPIA and MEIA assays, for execution by instrumentation software on the analytical system 2. When the chemist is modelling an assay, the flexible protocol inhibits any sequence of activities for the assay that will not run on the system 2. Thus, the system 2 never sees a corrupt assay because the flexible protocol rules are already imbedded in the assay protocol.

Figure 10:
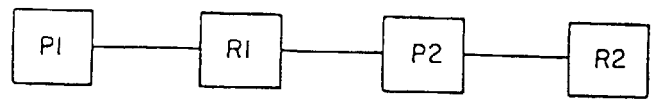
FIG. 10 is a block diagram showing the sequence of activities to be performed in a first assay.
Figure 11:
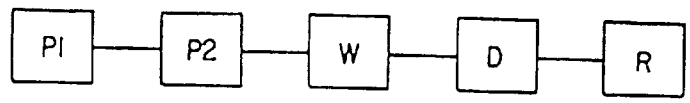
FIG. 11 is a block diagram showing the sequence of activities to be performed in a second assay.

The flexible protocol technology used to model an assay specifies (1) what activities are to be performed for a particular assay and the order in which the activities are to be performed, (2) the incubation periods between the activities, (3) how the activities are to be performed and their time durations, and (4) the equilibration and evaporation constraints for each assay. With respect to the first specification of the flexible protocol, the activity protocol, FIGS. 10 and 11 show activities to be performed by an assay and the order in which the activities to be performed. Referring more specifically to FIG. 10, a sequence of four activities is shown: a first pipetting activity (P1), a first reading activity (R1), a second pipetting activity (P2), and a second reading activity (R2). This sequence of activities can be, for example, the sequence for the FPIA assay as described in more detail below. Referring to FIG. 11, a second sequence of activities is shown including two pipetting activities (P1) and (P2), a washing activity (W), a dispensing activity (D), and a reading activity (R). This sequence represents, for example, the MEIA sequence of activities also described in more detail below.

Figure 12:
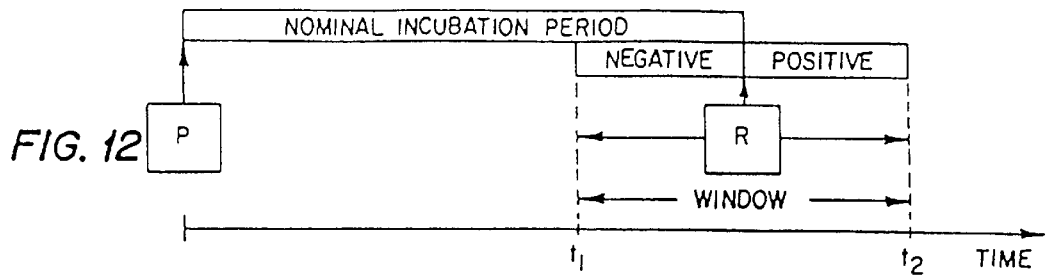
FIG. 12 is a block diagram showing an incubation period between two activities as comprising a nominal incubation period and a variable incubation window.
Figure 13:
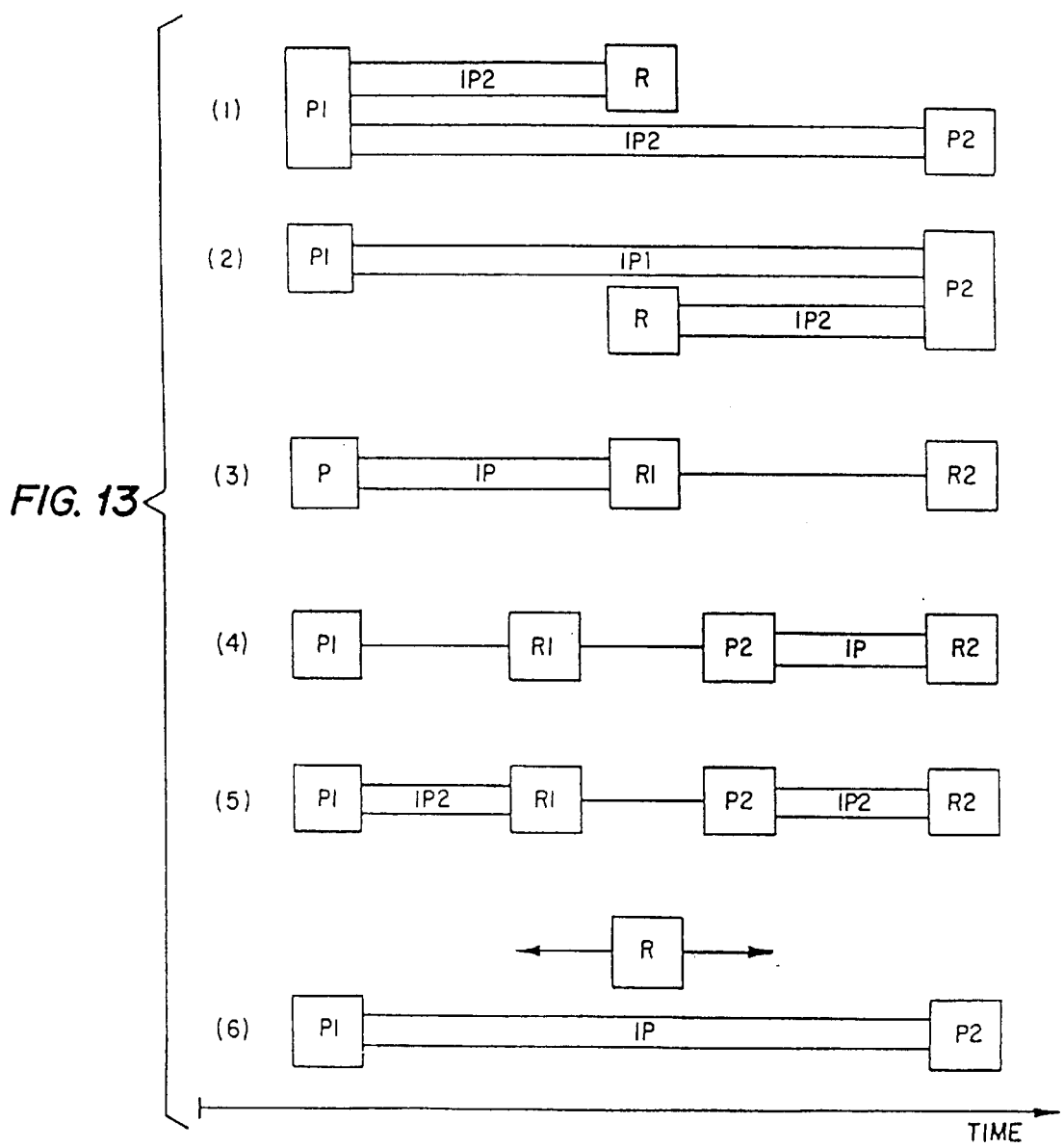
FIG. 13 is a set of six block diagrams each showing a different combination of activities and incubation periods reflecting the rules of a flexible protocol technology.

The second specification of the flexible protocol, i.e., the incubation schedule, relates to the incubation periods between the activities as shown in FIGS. 12 and 13. The incubation schedule defines the time periods between the activities, i.e., the time dependencies between the activities. More specifically, the incubation period includes a nominal time lapse between two activities, i.e., the nominal incubation period (NIP), and the amount of time that it can be varied, i.e., the incubation window. The incubation window includes the amounts of time which the scheduler may add to or subtract from the nominal incubation period (NIP) to optimize throughout of the system 2. Referring more specifically to FIG. 12, the nominal incubation period (NIP) defines the time between the pipetting activity (P) and the reading activity (R). The nominal incubation period can be reduced by the amount of time indicated by the negative portion of the window, in which case the reading activity (R) will occur sooner, or increased by the amount of time indicated the positive portion of the window, in which case the reading activity (R) will occur later. Thus, the scheduler has enough flexibility to vary the incubation period from time T1 to time T2 to optimize the task being performed on the system 2.

Referring to FIG. 13, six incubation schedule rules are shown with respect to time. These rules describe the proper and improper sequence of activities associated with incubation periods. Rule (1) specifies that one activity can initiate more than one incubation period. More specifically, the first pipetting activity (P1) initiates a first incubation period (IP1) constraining the reading activity (R), as well as second incubation period (IP2) constraining the occurrence of a second pipetting activity (P2). However, the converse is not permitted. Referring to Rule (2), only one incubation period can terminate in an activity. In other words, one activity cannot be constrained by more than one incubation period. For example, the second pipetting activity (P2) cannot be constrained by the two incubation periods (IP1) and (IP2) initiated by the first pipetting activity (P1) and the reading activity (R), respectively. The flexible protocol technology would invalidate this sequence. Referring to Rule (3), the last activity of an assay must be a termination point for an incubation period. Thus, the flexible protocol technology would invalidate the second reading activity (R2) because it does not terminate an incubation period, unlike the first reading activity (R1) which terminates the incubation period (IP) initiated by the pipetting activity (P). Such "post-incubation" activities are not permissible. Referring to Rule (4), activities not constrained by an incubation period that occur prior to the first incubation period are permissible. These "pre-incubation" activities such as, for example, the first pipetting activity (P1) and the first reading activity (R1), are permissible activities in an assay even though they are not constrained by an intervening incubation period, as long as they occur prior to the first incubation period (IP) which constrains the second pipetting activity (P2) and the second reading activity (R2). Although pre-incubation activities are permissible, Rule (5) specifies that activities constrained by an incubation period cannot precede a pair of unrelated activities constrained by a second incubation period. More specifically, referring to the specific example for Rule (5), even though the pipetting activity (P2) and reading activity (R2) are constrained with respect to each other by the second incubation period (IP2), they float in time because neither are constrained by either the first pipetting activity (P1) or the first reading activity (R1). Finally, Rule (6) states that an activity can float unconstrained between two other activities constrained by an incubation period. More specifically, the first and second pipetting activities (P1) and (P2) are constrained by the incubation period (IP) which does not constrain the reading activity (R). The reading activity (R) is a float activity which is not constrained by time, but only constrained by its order with respect to the other two activities, i.e., it must occur after the first pipetting activity (P1) and before the second pipetting activity (P2).

Figure 14:
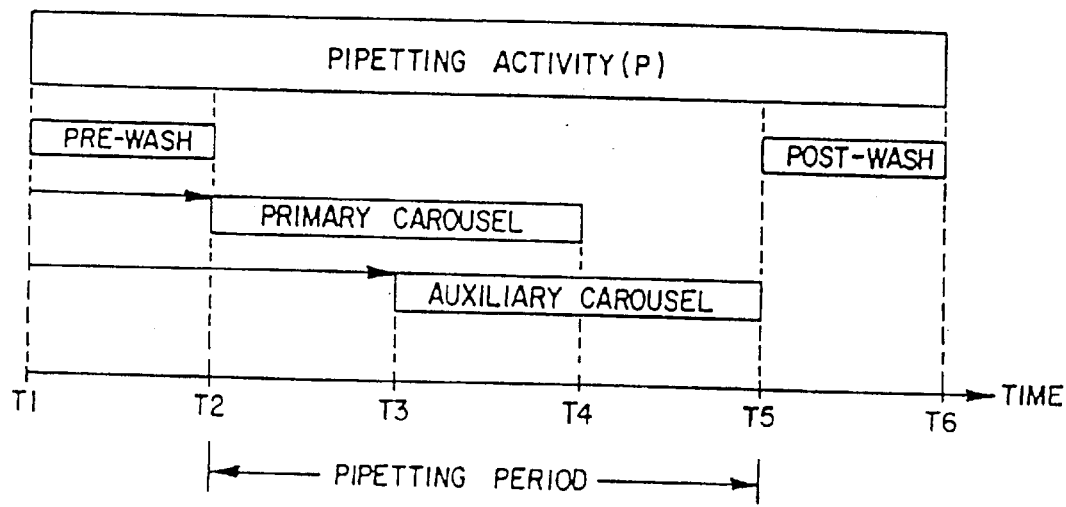
FIG. 14 is a block diagram showing the timing protocol for a pipetting activity.

The third specification of the flexible protocol technology, the activity description, specifies how activities are to be performed and their time duration, i.e., the timing protocol, as indicated above. Referring more specifically to FIG. 14, the timing protocol for a pipetting activity (P) is shown. This particular pipetting activity (P) is similar to the one used for the MEIA assay which requires three resources of the analyzing system 2, including the primary carousel 46, the auxiliary carousel 64, and the process pipettor 50. The pipetting activity (P) consists of 6 events, commencing with a pre-wash event at time T1 when the application software determines that the pipettor 50 must be cleaned of contaminants from a previous pipetting activity. If, however, the system software knows that the previous pipetting activity will not contaminate the current pipetting activity (P), the pre-wash event will not occur. The pre-wash event will be described in more detail below.

The duration of the pre-wash period is known to the system software which commences execution of the pipetting activity (P) relative to the second event related to the primary carousel 46. The second event occurs at time T2 corresponding to the amount of time that elapses before the reaction vessel 34 is available on the primary carousel 46 for the pipettor 50. The reaction vessel 34 will not be available until other activities have been completed and the primary carousel 46 has been repositioned if necessary. At time T2, the pipettor 50 begins aspirating fluid from the reaction vessel 34. When fully aspirated, the pipettor 50 moves into position with the auxiliary carousel 64. The pipetting period for the primary carousel 46, time T2 to time T4, includes the time necessary for the pipettor 50 to aspirate fluid from the reaction vessel 34 and the amount of time necessary for the pipettor 50 to move clear from the primary carousel 46. The third event occurs at time T3 representing the amount of time that elapses before the cartridge 68 is available on the auxiliary carousel 64 for the process pipettor 50. At time T3, the auxiliary carousel 64 is in position for the pipettor 50 to begin dispensing the fluid into the cartridge 68. Events 4 and 5 occur at times T4 and T5, respectively, and represent the time after which the carousels 46, 64 are no longer needed for the current pipetting activity (P), and are available for subsequent activities. When the auxiliary carousel 64 becomes available, the pipetting period from time T2 through time T5 is complete. After the pipetting period, the pipetting activity (P) concludes with the completion of a post-wash cycle at time T6. Whether or not the post-wash cycle is necessary is dependent on whether the current pipetting activity (P) would contaminate the next activity to be performed.

The foregoing description clearly shows that the flexible protocol technology enables the scheduler to properly sequence assay activities, compress incubation periods and perform other functions so that the analyzing system 2 is optimized to operate continuously at high throughput rates. The flexible protocol technology is to be distinguished from a "fixed" protocol, such as the one disclosed in European Patent Application 410,645 published Jan. 30, 1992, which describes an analyzer restricted to a fixed cycle that cannot be optimized. When the scheduler begins the process of scheduling a test, the process is broken into two stages: (1) the scheduler reviews the assay activities just described and the fixed system activities, such as for example reaction vessel 34 loading and unloading activities, to ensure that execution of the test will not clash with the activities of other test in process before the test is kitted, and (2) an attempt to perform each test activity prior to its original scheduled execution time within the parameters of the assay protocol to minimize the amount of time resources are idle and increase the throughout of tests in the system.

In the first stage, the operator chooses the order that tests are prepared to run on the system 2 by selecting the placement of samples 26 on the system 2. The sample 26 placed closest to the pipette station is the first sample prepared to run on the system 2. To guard against evaporation, a test will not be prepared until the scheduler ensures that all resources used by the test's activities will be available at the required times set forth in the test's assay protocol. Preparation of the next test in line is postponed when activities of other tests in progress are using resources at the time required by an activity of the next test. The sample preparation area of the system 2 remains idle until the next test is successfully scheduled without conflict. For example, if a pipetting activity (P) requiring twenty seconds must be performed sometimes during a two-minute window within 3–5 minutes after a kitting activity, preparation is postponed until the pipetting activity can be accomplished somewhere in that window. When proper scheduling of the next test can be achieved, the test will be prepared and transferred into the process area.

The second stage of the scheduling process is to optimize the workload for each system resource to minimize both the resource's idle time and the time required to perform the resource's workload. Once tests are transferred into the process area, the scheduler optimizes the existing schedule for each resource. At predetermined intervals, the scheduler examines the next interval of work for each resource. If there is any idle time in this interval, the scheduler attempts to minimize the idle time by rearranging the resource's workload to eliminate idle time, providing the activities remain within their allowed incubation windows. When optimization of this interval is complete, this section of the workload is performed by the resource at the designated times. The scheduler continues to prepare samples as long as there are samples 26 on the system 2 that have tests ordered to be run. Optimization of the resources' workloads will continue until all tests transferred into the system have finished processing.

Another feature of the invention provides a procedure for interrupting the scheduler's preparation of samples 26. According to this feature, the operator of the system 2 identifies a sample 26 for priority handling (hereinafter the "stat sample") in both the front-end sample are and the processing area of the analytical system 2. The operator chooses the order that tests are prepared to run on the system 2 by selecting the placement of samples 26 on the sample carousel 28. The sample 26 placed closest to the pipette station is the first sample prepared to run on the system 2. This pattern of sample 26 preparation is interrupted whenever the operator places a stat test on the system 2. Whenever a stat test is ordered, the system 2 will finish preparing the test on the current sample, and then move directly to the stat sample to prepare al its tests. To guard against evaporation, sample preparation will not begin for a test before proper scheduling of the test's activities in the processing area is ensured.

The system scheduling algorithm is also modified for stat processing. The scheduling algorithm used for normal tests attempts to maximize the number of tests processed in the instrument each hour. This occurs by allowing sufficient time between test activities to enable other tests' activities to be performed in these gaps. The scheduling approach used for stat tests attempts to process this one test in the shortest amount of time possible. Each activity of a stat test is scheduled at the earliest possible times of execution as defined in the test's assay definition. When all activities of a test are guaranteed proper scheduling in the system 2, sample preparation of the test will begin. After all tests on the stat sample are prepared, the system 2 will return to the sample 26 it was working on before it serviced the stat sample.

Stat tests receive special consideration in the processing area when there is idle time in a resource's workload. At predetermined intervals, the scheduler examines the next interval of work allocated to each resource in the processing area of the system. If there is any idle time during this interval, the scheduler attempts to minimize it by rearranging the resource's workload as described above in greater detail. Test activities scheduled for this resource that can be performed earlier than they are currently scheduler, as defined by their assay protocols, are moved forward to fill the idle time. Stat test activities are the first candidates to be pulled forward in the workload, thus further decreasing the amount of time needed to process the stat test in the instrument. Although stat tests receive special scheduling treatment, it does so without negatively affecting the system's throughout.

It is to be understood that the scheduling operation of the continuous and random access analytical system of the present invention can be utilized in similar automated instruments requiring protocols for scheduling activities and incubation periods to optimize the performance of assays. For example, the invention can be used in conjunction with performing homogeneous assays, heterogeneous assays and immunoassays, as well as the FPIA and MEIA immunoassays. The protocols being modelled would simple reflect the assays being performed on the analyzer.

ASSAY VERIFICATION

The method of the present invention can be employed in the various assay methods described herein, whether such methods are performed manually or with the various assay detection systems and instruments described herein. The method of the present invention employs an assay verification sample comprising a positive analyte component, the test sample under analysis, and one or more assay reagents, wherein the assay verification sample is analyzed employing the same assay reagents and essentially the same assay methodology employed to analyze the test sample. The assay verification sample is prepared by adding the positive analyte component to the test sample under analysis for the separate analysis thereof. Such separate analysis can be performed by either (i) first removing a portion of the test sample for the separate analysis thereof, and then forming the assay verification sample with the remaining portion thereof for the separate analysis thereof, or (ii) the test sample can first be independently analyzed, and then the assay verification sample can be formed with the independently analyzed test sample together with any assay reagents present during such first analysis. The positive analyte component is the analyte under determination, or analog thereof, which is present in the assay verification sample at a known amount or concentration to provide a detectable signal or response in the particular assay methodology being performed.

In particular, when analyzing a test sample employing an assay verification sample according to the present invention, the test sample is analyzed according to a desired assay protocol or methodology employing the necessary assay reagents therefor, and the assay verification sample is independently analyzed according to essentially the same assay protocol or methodology and employing the same assay reagents which were utilized to analyze the test sample. Accordingly, if the test sample provides a negative result, an appropriate signal difference with the assay verification sample verifies that such negative result is due to the absence of analyte. On the other hand, if the assay verification sample does not provide an appropriate detectable signal or response, then the negative result for the test sample could be due to a number of reasons. For example, the assay reagents could lack potency or are otherwise not capable of performing the particular assay to provide accurate results; the test samples or assay reagents could have been tampered with or adulterated, such as by the addition of blocking agents or inhibitors to a test sample for the analysis of such test sample for drugs of abuse and other controlled substances; the test sample could have been incorrectly processed, such as incorrect pipetting steps or incorrect addition of reagents; contaminants or other substances which could interfere with assay performance may be present as the result of, for example, manufacturing, sterilization, washing, and the like processes, of test tubes, reaction vessels, assay containers, assay devices, and the like.

The method of the present invention is particularly useful when analyzing test samples for the presence of analytes which are typically present in low frequencies. Such analytes include, but are not intended to be limited to, hepatitis B surface antigen (HBsAg), antibodies to hepatitis B core antigen, such as anti-hepatitis B core antigen IgG and IgM (Anti-HBC), human immune deficiency virus 1 and 2 (HIV 1 and 2), human T-cell leukemia virus 1 and 2 (HTLV), hepatitis B e antigen (HBeAg), antibodies to hepatitis B e antigen (Anti-HBe), and the like analytes. Since such analytes occur in low frequencies, particularly when performing assays therefor on hundreds of test samples during the course of a day, the majority of such assay results may be negative. Accordingly, when performing such analyses employing the assay verification sample according to the present invention, potency of assay reagents employed therein and proper performance of the assay methodologies is verified.

According to one embodiment, the method of the present invention is particularly useful when performing a heterogeneous immunoassay format. According to such assay format, a reaction mixture is formed by contacting the test sample containing the analyte under determination with a labeled reagent or tracer comprising an analyte, and analog of the analyte, or an antibody thereto, labeled with a detectable moiety, to form a free species and a bound species thereof. In order to correlate the amount of tracer in one of such species to the amount of analyte present in the test sample, the free species is separated from the bound species. Such separation is accomplished by contacting the reaction mixture, either simultaneously or sequentially, with a solid phase material for the direct immobilization of one of the binding participants in the binding reaction, such as the antibody, analyte or analog of the analyte, wherein one of the binding participants is immobilized on the solid phase material, such as a test tube, beads, particle, microparticles or the matrix of a fibrous material, and the like, according to methods known in the art. Following, for example, one or more washing steps to remove any unbound material, an indicator material is added to produce a detectable response which can be detected and correlated to the amount of antigen or antibody present in the test sample. Another form of a heterogenous immunoassay employing a solid phase material is referred to as a sandwich immunoassay, which involves contacting a test sample containing, for example, an antigen with a protein such as an antibody or another substance capable of binding the antigen, and which is immobilized on a solid phase material. The solid phase material typically is treated with a second antigen or antibody which has been labeled with a detectable moiety. The second antigen or antibody then because bound to the corresponding antigen or antibody on the solid phase material.

When performing such heterogeneous immunoassays according to the present invention, the reaction mixture containing the free and bound species is divided into first and second portions, wherein the free and bond species of the first portion are separated as described above and an indicator reagent added thereto a provide a first result. A positive analyte component is added to the second portion to form the assay verification sample according to the present invention, and is similarly analyzed independently to provide a second result. Alternatively, subsequent to obtaining the first result, the second portion containing the positive analyte component can be added to the first portion to provide the second result. In either case, if the first result is negative, an appropriate second result, i.e., an appropriate detectable signal or response, verifies that such negative result of the test sample is due to the absence of analyte in the test sample. On the other hand, if the first result is negative, absence of an appropriate second result indicates that one or more of the events described could have occurred.

According to the present invention, the various known assay techniques and formats described herein, can be performed manually or can be performed employing various analytical apparatus described herein, as well as other analytical apparatus known in the art. It is to be understood that when such assay techniques according to the present invention are performed with an automated analytical system utilizing one or more automated pipetting steps, the various pipette additions of assay reagents and formation of the assay verification sample as described herein can be performed sequentially or simultaneously. In addition, the method of the present invention is particularly useful in the automated continuous and random access analytical system described below, which typically does not necessarily perform the same pipetting sequence consecutively for the determination of the same analyte in a different test sample, such as with batch analyzers known in the art. Generally, such assay techniques and formats include, but are not intended to be limited to, spectrophotometric absorbance assays such as end-point reaction analysis and rate of reaction analysis, turbidimetric assays, nephelometric assays, radiative energy attenuation assays (such as those described in U.S. Pat. No. 4,496,293 and U.S. Pat. No. 4,743,561 and incorporated herein by reference), ion capture assays, colorimetric assays, fluorometric assays, electrochemical detection system, potentiometric detection systems, amperometric detection systems, and immunoassays. Immunoassays include, but are not intended to be limited to, heterogeneous immunoassays such as competitive immunoassays, sandwich immunoassays, immunometric immunoassays, and the like, where the amount of a detectable moiety employed therein can be measured and correlated to the amount of analyte present in a test sample.

SMART WASH

The present invention additionally provides a method and apparatus for identifying analytical interactions which are likely to occur between various steps in a random access analytical system, particularly steps involving pipetting sequences in which the likely interactions are carryover by or cross contamination of test samples or reagents. The method and apparatus of the present invention determines when those interactions are likely and allows for random access processing even in those situations (that is, the method and apparatus allows the system to react in a different manner in instances in which those interactions are likely, than in instances in which the interactions are less likely). The invention can do this because the system software (in particular, the scheduler software) is able to randomly insert and remove pipetting events from the processing timeline in order to control carryover or cross-contamination. By so inserting and removing pipetting events, the system varies test sample and reagent wash volumes to correspond with wash volumes necessary for the particular test samples or reagents being processed in order to eliminate the possibility of interactions.

The present invention is capable of controlling carryover or contamination by utilizing a simple matrix, as described below in detail. The matrix is set up in order to relate the particular pipetting steps performed by the system to the potential of those steps for carryover and contamination. Based upon values determined by the system from that matrix, the system modifies wash volumes between pipetting steps to minimize wash volumes but to allow sufficient wash volumes to eliminate contamination or carryover. The apparatus and method of the invention is particularly useful when incorporated in the automated analytical system particularly described herein, which system is capable of simultaneously performing two or more assays on a plurality of test samples in a continuous and random access fashion.

In order to reduce carryover and contamination, the present system and method, in effect, looks at the sources that create the problem. This can be better understood in concept by considering the general scheme of the scheduler software and the pipetting and wash steps. Since each pipette step can result in carryover or contamination, as well as possibly be sensitive to carryover, the present invention provides simple categories for the contaminating potential of each pipette step and then identifies to which of those categories each assay step is sensitive. This is where the aforementioned matrix comes into play. The matrix is set up to identify when carryover or contamination is likely, based upon preceding and succeeding pipetting steps scheduled by the scheduler software. The apparatus and method, based upon values from the matrix corresponding to the preceding and succeeding pipetting steps, causes the analytical system to respond with appropriate wash characteristics to eliminate the possibility of undesirable carryover or contamination when they appear likely. In operation, the analytical system is automatically cleaned to a nominal level, suitable for eliminating carryover or contamination in the typical instance. In the prior systems, it was necessary that the system be cleaned at an extreme level which would eliminate carryover or contamination in the worst cases. The present invention, however, provides for extra washing in those cases in which the system software identifies, based on the scheduled sequence, the situation of a potentially contaminating step occurring before a sensitive step. In the instance of that combination, the software causes the system to activate a predetermined super wash that is adequate for controlling the carryover in those extreme instances.

This approach in the present invention reduces the amount of washing performed by the system because sensitive steps do not necessarily always follow contaminating steps and so the super wash is not always employed. In short, the method of the system accounts for both the situation where normal wash is required and the situation where a greater wash is required, and determines which type wash is necessary in any instance, even though it is not possible, due to the random and continuous access nature of the system, to know and priori when carryover is or is not likely to occur. The present invention also allows for pipette steps to be removed or inserted into the processing timeline as required due to the random access nature of the system, and maintains the system to eliminate the possibility of a contaminating situation. Even further, the invention allows the software to adjust the required washing without having to manipulate other pipetting steps in the processing timeline, even in a system which allows continuous operation.

The method and apparatus are designed to minimize wash fluid consumption by the instrument by having the system software track some basic information relating to the pipetting steps that immediately precede and follow any given step on the timeline. Since they involve the interaction of all assays with one another, it is preferred that all assays use the same approach to cleaning the pipette within their protocol. Unlike wash systems and methods previously described, the method according to the present invention (1) reduces wash volumes to help the management of onboard liquid and waste; and (2) reduces washing times to help improve throughput.

In particular, probe wash control in systems previously described was provided by recommendations for post washing after each pipetting block as follows:

| Pipetting Sequence 1 | Post Wash 1 | → | Pipetting Sequence 2 | Post Wash 2 |
|---|---|---|---|---|

According to the invention, the basic pipette cleaning is provided as before, i.e., with a post wash which should be sufficient to control carryover for most of assay steps that might follow it. However, if the recommended post wash is inadequate for controlling cross-contamination or carryover to the following step, then a prewash is incorporated for that second step as follows:

| Pipetting Sequence 1 | Post Wash 1 | → | Pre Wash 2 | Pipetting Sequence 2 | Post Wash 2 |
|---|---|---|---|---|---|

The prewash is variable and has two levels, nominal and super. The nominal prewash is the volume that should be used all the time. When carryover is possible, the super wash would then be used. Typically, the nominal wash volume would be zero. Since the methodology software feature identifies when carryover is possible, the post wash volumes used across the system can be reduced in value from what they were prior to the method, whereby each assay is no longer required to be cleaned well enough to control the worst case carryover situation. Additional wash needed to control carryover will be added through the super wash when the software identifies a carryover potential.

Parameters, Tables and Terminology for Smart Wash

The method preferably utilizes five parameters to describe each pipetting step, two index values and three wash parameters, wherein (i) the two index values are sus (susceptibility to contamination) and con (probability to contaminate); and (ii) the three wash parameters are nom (nominal prewash number), sup (super prewash number), and pw (post wash number). The wash parameters are not volumes. The wash parameters are numbers that identify washes in a wash library as described below.

| | Current Wash Library | | |
|---|---|---|---|
| Wash Number | Volume | Total Waste | Washcup |
| 0 | 0 ml | — | — |
| 1 | 2 | 1 ml | 1 ml |
| 2 | 2.5 | 1 | 1.5 |
| 3 | 3 | 1 | 2 |
| 4 | 3.5 | 1.5 | 2 |
| 5 | 4 | 2 | 2 |
| 6 | 4.5 | 2 | 2.5 |
| 7 | 5 | 2 | 3 |
| 8 | 1 | no | yes |
| 9 | 2 | no | yes |
| 10 | 3 | no | yes |
| 11 | 4 | no | yes |
| 12 | 5 | no | yes |

The sus and con parameters are used to flag the probability for carryover or cross-contamination to occur. They are related to each other through the matrix of the present method.

The matrix of the present method contains only 0's and 1's, corresponding to off and on, respectively; 0=no probability for carryover; 1=probability for carryover does exist.

| | | Method Matrix | | | |
|---|---|---|---|---|---|
| | | none 1 | sus parameter | | |
| | | | 1 | 2 | 3 |
| con parameter | | | 0 | 0 | 0 |
| | w/airgap | | | | |
| | | | 2 | 0 | 1 | 1 |
| | w/o airgap | | | | |
| | | | 3 | 0 | 0 | 1 |

| con | description |
|---|---|
| 1 | not contaminating (no sample) |
| 2 | aspiration of sample or sample mix with airgap |
| 3 | aspiration of sample or sample mix without an airgap |

| sus | description |
|---|---|
| 1 | not susceptible to contamination |
| 2 | sensitive to aspiration of sample or sample mix with an airgap |
| 3 | sensitive to aspiration of sample or sample mix without and with an airgap |

For example, a pipette block is susceptible to all sample pipetting (sus index=3). For a preceding pipette step which has a con index of 1 (matrix value=0), no super wash is performed. For a preceding pipette step which has a con index of 2 or 3 (matrix value=1), the super wash is performed.

The matrix of the present method provides information to the software that the probability for carryover or cross-contamination exists, but it does not provide information to the software as to what volumes to use for a wash step, which is instead provided from the nom, sup and pw parameters. The matrix of the present method may be expanded should other contaminating species in addition to sample be defined.

The con parameter and the pw numbers describe to the software what state the probe is in prior to the next pipetting step. The rules established for identifying these parameters for pipetting steps are requirements for all assays to follow.

The con and pw parameters are defined as follows:

| Description | con value | pw number/vol |
|---|---|---|
| Not contaminating (no sample) | 1 | (2 ml) |
| Asp of sample/sample mix with airgap | | 2 |
| *<= 50 μl aspirated | 1 | (2 ml) |
| *<= 100 μl aspirated | 3 | (3 ml) |
| *<= 150 μl aspirated | 5 | (4 ml) |

Aspirating>150 μl of sample or sample mix with an airgap is discouraged because of the necessity to use excessive washing.

Asp of sample/sample mix without an airgap 3, use the same pw values as above.

"*" indicates the level of sample carryover present when the method of the present invention is not utilized (post wash only) is 10 ppm or less with the above recommendations. In all cases, the minimum allowable pw value is 2 ml wash.

The sus, nom and sup parameters are under the control of the assay protocol. It is to be understood that any criteria established for identifying these parameters are recommendations, and that the assay protocol developer will best know which pipetting sequences are sensitive to carryover, which sequences create the problem and what wash volume is necessary to clean the probe.

Nominal and super washes are used for a susceptible pipette block for control of carryover. Use 0 for Wash Library number 8 through 12, where only wash to washcup is needed: nom=0—no nominal prewash is preformed; nom=8 to 12—use Wash Library numbers 8 through 12 (1–5 ml wash-washcup); sup=0; no super prewash is performed; sup=8 to 12—use Wash Library number 8 through 12 (1–5 ml wash-washcup)

Because of scheduling constraints, the super wash volume may not be greater than the minimum post wash (2 ml), plus the nominal wash; if it is necessary to use more super wash volume, the nominal wash should be increased as well. For example, if the nominal wash is 0 ml, super wash may only be 0, 1 or 2 ml. If the required super wash is 4 ml, nominal wash must be at least 2 ml.

The minimum post wash requirement and super wash volume constraint not only ensures proper scheduling, but also protects the system from a highly contaminating step being "hidden" from a susceptible step because a simple step sits between them on the timeline that needs only a minimum wash. The minimum post wash requirement guarantees that the probe will be properly cleaned when that susceptible step is to be pipetted.

The kitting center is treated as one pipette block. Carryover experiments have shown that a post wash of at least about 2 ml is sufficient to clean the probe to a carryover level of 1 ppm or less when sample is kitted first followed by wash and pipetting of reagents. Total wash following sample should be about 4 ml total wash before next kitting activity. Contamination of the reagent bottle following sample will come from the outside of the probe. This is reduced to insignificant levels by wash to waste cup, e.g., 200 to 1,000 $\mu$l, followed by from between about 1 ml to about 2 ml wash to the wash cup.

CHEMILUMINESCENT TEST

The present invention includes a unique system and method for automated, continuous and random access analytical testing, capable of performing chemiluminescent assays such as described in commonly owned U.S. Pat. No. 5,089,424 and U.S. patent application Ser. No. 206,645 filed Jun. 14, 1988, which are each incorporated herein by reference. At least two types of chemiluminescent assays, magnetic particle capture and microparticle membrane capture, are possible by the system and method.

According to one embodiment, magnetic particle capture, a chemiluminescent detection signal is produced by immobilized immune complexes comprising antibody coated magnetic particles. A cuvette having satisfactory optical qualities is used to contain the immune complexes suspended in solution. A magnetic field is imposed along the wall of the cuvette to perform a separation of immune complexes in solution from other particles in the solution. The immune complexes, once separated, are washed, a trigger reagent is added to the complexes, and a resulting chemiluminescence from the immune complexes is detected and measured. The detection and measurement is performed using a chemiluminescent detection system while the immune complexes remain in the cuvette.

According to another embodiment, microparticle membrane capture, analyte is captured in a liquid phase employing, for example, microparticles, polyionic capture agents and the like, having a binding affinity for the analyte. The capture agents are mixed with the bind the analyte. The captured analyte is subsequentially immobilized. Immobilization may be performed by utilizing a solid, porous element which holds the captured analyte but allows passage of solution. A chemiluminescent signal is then chemically excited and detected. This embodiment utilizes fast fusion rates in solution to provide highly sensitive assays for a wide range of analytes.

These chemiluminescent assay systems and methods may be employed with an automated, continuous and random access analytical system and method, as described herein. The automated, continuous and random access analytical system and method can further include fluorescent assays and chemiluminescent assays processing simultaneously and concurrently on the same platform. Such as automated analytical system and method is capable of simultaneously performing two or more of these and/or other assays on a plurality of test samples in a continuous and random access fashion.

Figure 15:
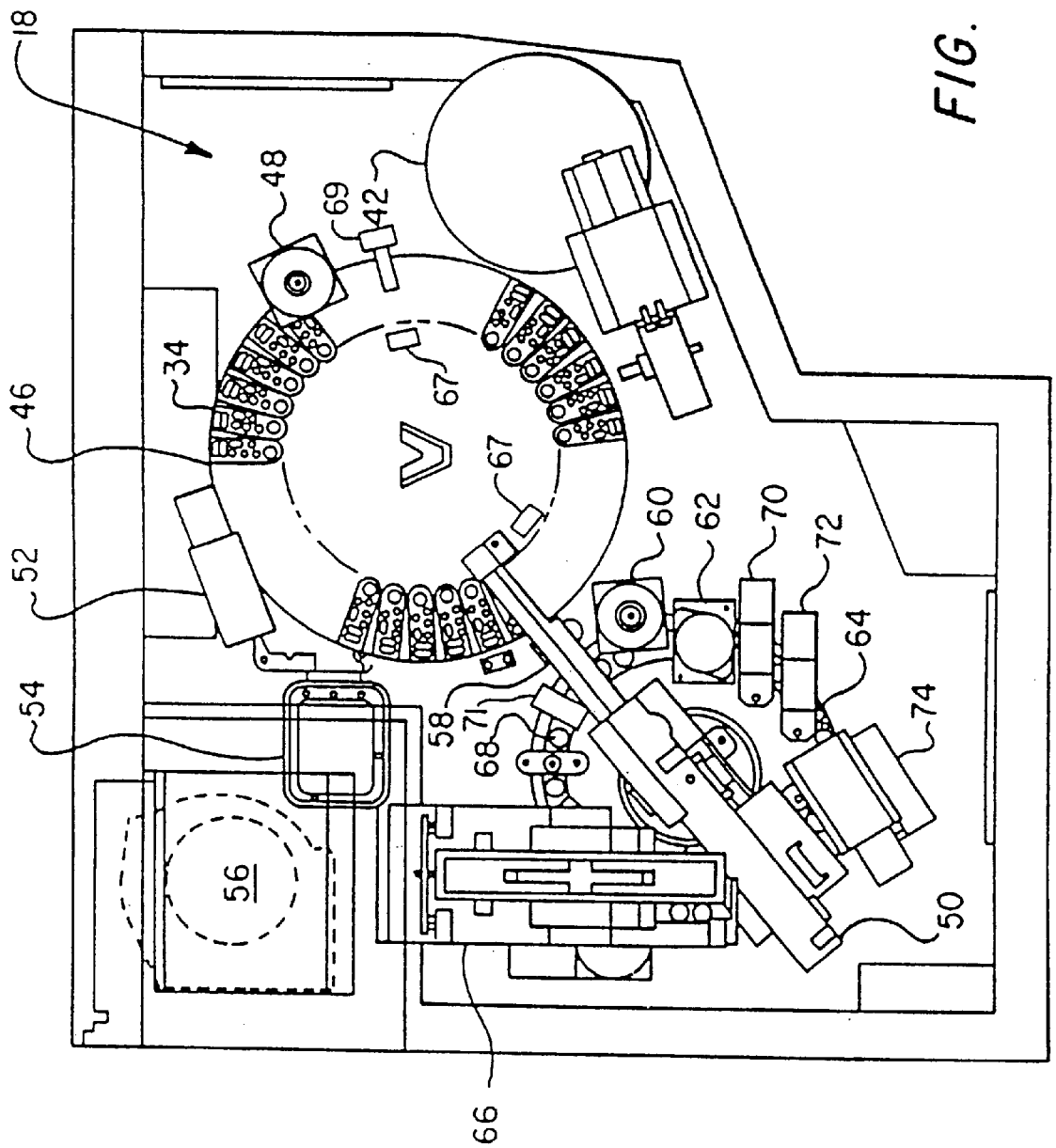
FIG. 15 is a top plan view of the automated analytical system in section with component covers removed to show the automated analytical apparatus in detail and relative position inclusive of a chemiluminescent reader for a magnetic particle capture technology and a chemiluminescent reader for membrane particle capture technology.

FIG. 15 is a top plan view of the automated analytical system in section with component covers removed to show the automated analytical apparatus in detail and relative position of the two types of detection systems utilizing chemiluminescent assay technology, both magnetic particle capture and microparticle membrane capture, which may be employed in the present invention. In one of such detection systems, the process carousel 46 has two magnetic separation stations 67 and a chemiluminescent reader detection module 69 for magnetic particle capture incorporated thereon for providing chemiluminescent magnetic particle capture assays. In the other one of the detection systems, the auxiliary carousel 64 has mounted thereon a chemiluminescent reader 71 for providing microparticle membrane capture assays.

Figure 16:
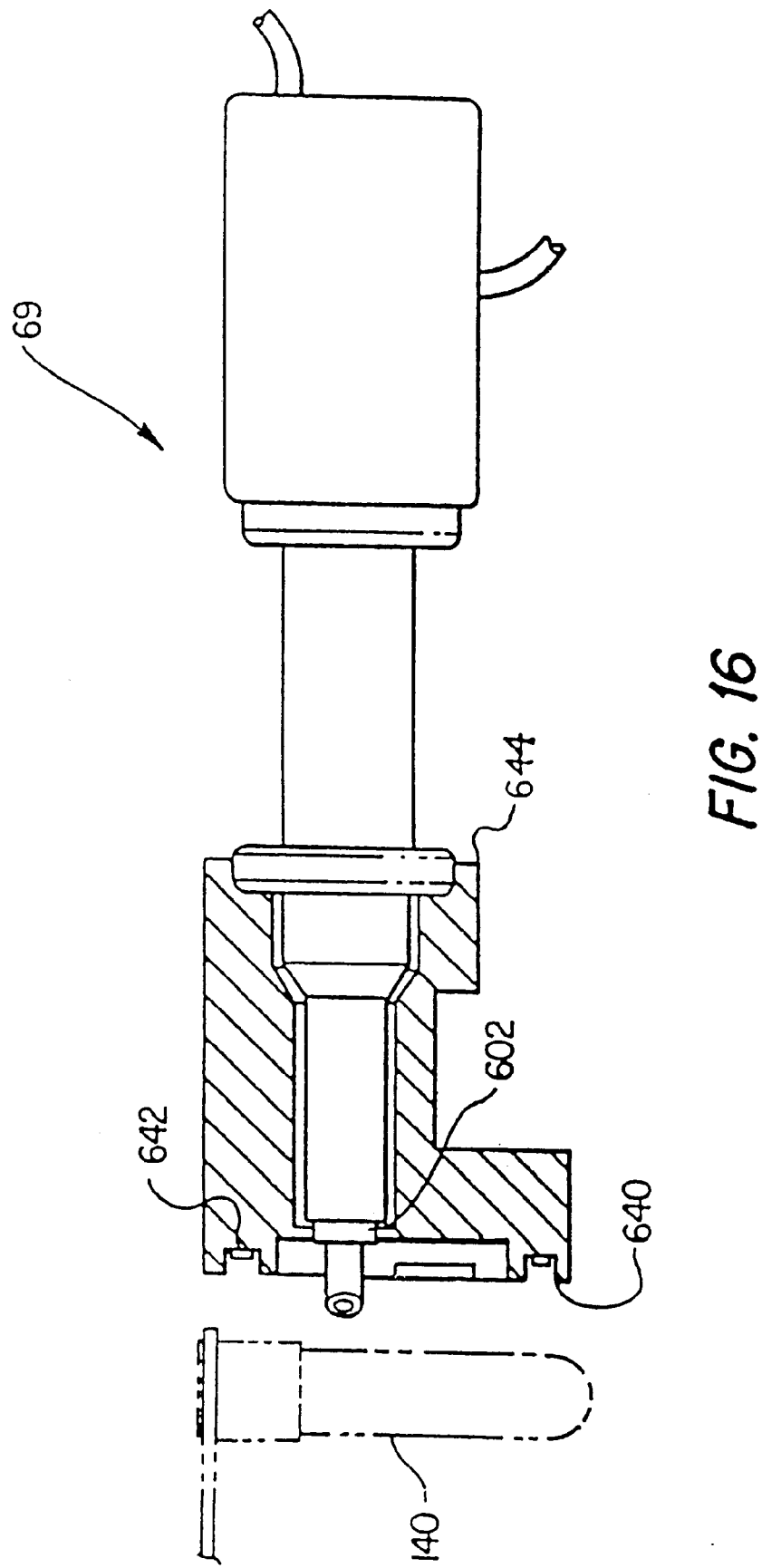
FIG. 16 is a cross-sectional view of a detection head of the detection device for chemiluminescent detection.

A depiction in schematic cross-sectional view of a signal detection module 69 for use in the magnetic particle capture system 67, 69 is shown in FIG. 16. The detection module 69 comprises a light guide 602 and is mounted horizontally in a housing 644 at a station for viewing the disposable cuvettes 140 (shown in phantom) carried on the process carousel 46 (not shown in FIG. 16). At this station, the signal detection module 69 takes readings of the contents of each cuvette 140 as it passes the module 69.

Figure 17:
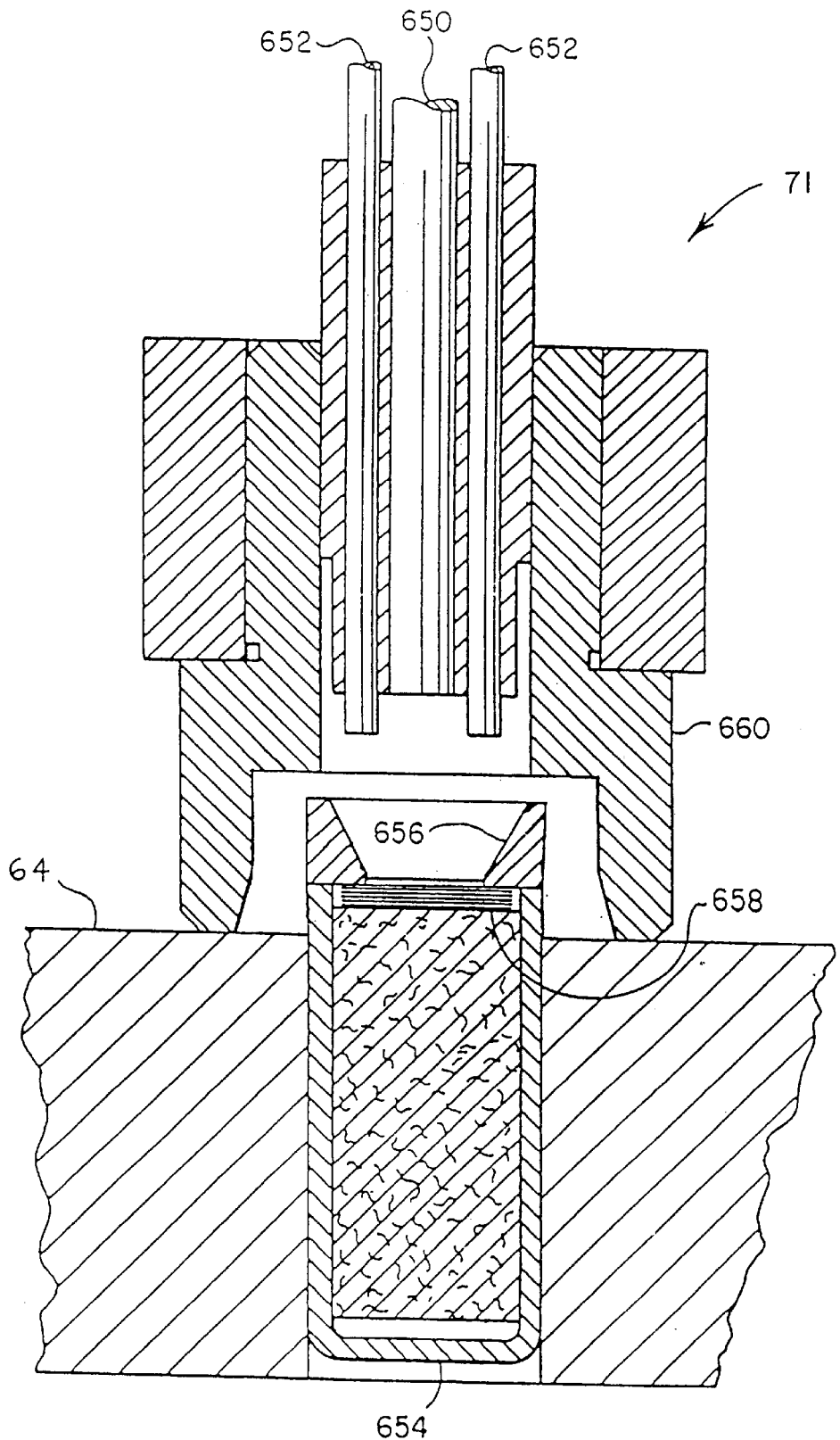
FIG. 17 is a cross-sectional view in section of the detection device light pipe positioned over a chemiluminescent particle capture container with light shield in place.

In FIG. 17, a depiction of a cross-sectional view of a signal detection module 71 for use in the microparticle membrane capture system is illustrated. The detection module 71 includes a light pipe 650 and injection conduits 652 positioned on either side of the light pipe 650. The module 71 is mounted vertically above the fiber cartridges 654 carried by the auxiliary carousel 64 (in a manner similar of MEIA cartridge 68 shown in FIG. 15) at a station for viewing the contents of each cartridge 654 as the auxiliary carousel 64 rotates each one underneath the module 71. The cartridge 654 is similar in structure to the MEIA cartridge 68 shown in FIG. 55 described in more detail below and, as such, comprises a funnel-shaped aperture 656 opening to a solid, porous element 658, preferably in the form of a fibrous matrix. The module 71 also comprises a light shield 660 which shrouds the emitting end of the light pipe 650 and the aperture 656 of the cartridge 654 to shield them from other light sources which would interfere with the reading.

It is to be understood that each of the magnetic particle capture systems 69 and the microparticle membrane capture system 71 shown in FIGS. 16 and 17, respectively, is intended as exemplary of those type systems. Other systems and arrangements and configurations are possible. The operation of any such system will, however, operate in about the same manner. Chemiluminescent released photons from the contents of the cuvette 140 or cartridge 654, as the case may be, are transmitted through the light pipes 602, 650 of the detection module 69, 71 to a photomultiplier tube (not shown). The module 69, 71 and photomultiplier tube measures the chemiluminescent signal of the contents of the cuvette 140 or cartridge 654, as applicable.

It is to be understood that the chemiluminescence testing system and method of the present invention can in similar manners be utilized in any automated instrument where chemiluminescence testing is desired. As is clearly seen, the present invention provides significant advantages in this technology. The present invention is believed to be especially effective when manufactured and employed as described herein, however, those skilled in the art will readily recognize that numerous variations and substitutions may be made in the device and method and its use, steps, and manufacture to achieve substantially the same results achieved by the embodiments and, in particular, the preferred embodiment expressed and described herein. Each of those variations is intended to be included in the description herein and forms a part of the present invention. The foregoing detailed description is, thus, to be clearly understood as being given by way of illustration and example only, the spirit and scope of the present invention being limited solely by the appended claims.

LIQUID LEVEL SENSING

The present invention includes a unique system and method for sensing fluid levels in the various sample containers of the automated analytical system. The fluid level sensing system detects whenever the automated pipette probe contacts a liquid. The system detects amplitude change in a near-ratio frequency (RF) signal which is radiated by the probe and received by a series of antennas located below the various sample containers. The system can be through of as detecting a change in capacitance between the probe and the applicable antenna when the probe contacts liquid. The system continually monitors the capacitance of the probe in air and detects a quick change in capacitance in response to the probe contacting liquid.

A significant feature of the fluid level sensing system is that the presence of liquid is reported only when both signal amplitude and rate of signal change indicate that the probe has contacted liquid. Previous systems which utilized signal amplitude to detect liquids reported liquid detections based only on signal amplitude exceeding a present threshold. Therefore, these systems were adversely affected by changes in signal amplitude induced by changes in temperature, humidity, aging of parts, parts variation, and most significantly, probe position in relation to other components in the automated analytical system. These conditions caused previous systems at times to falsely indicate the presence of fluid, or conversely, to fail to detect fluid presence. Basing liquid detections on both signal amplitude and rate of change of signal amplitude greatly reduces the number of such false or failed detections.

Some previous liquid level detection systems detected in electrical phase shift of a sinusoidal signal present at the pipette probe whenever the probe contacted a liquid. These phase-shift systems were limited, however, to analytical systems which utilized only deionized water in the fluid line to the probe. The present invention's use of signal amplitude for liquid detection enables the use of a conductive diluent, such as saline solution, in the fluid line to the pipette probe.

Figure 18:
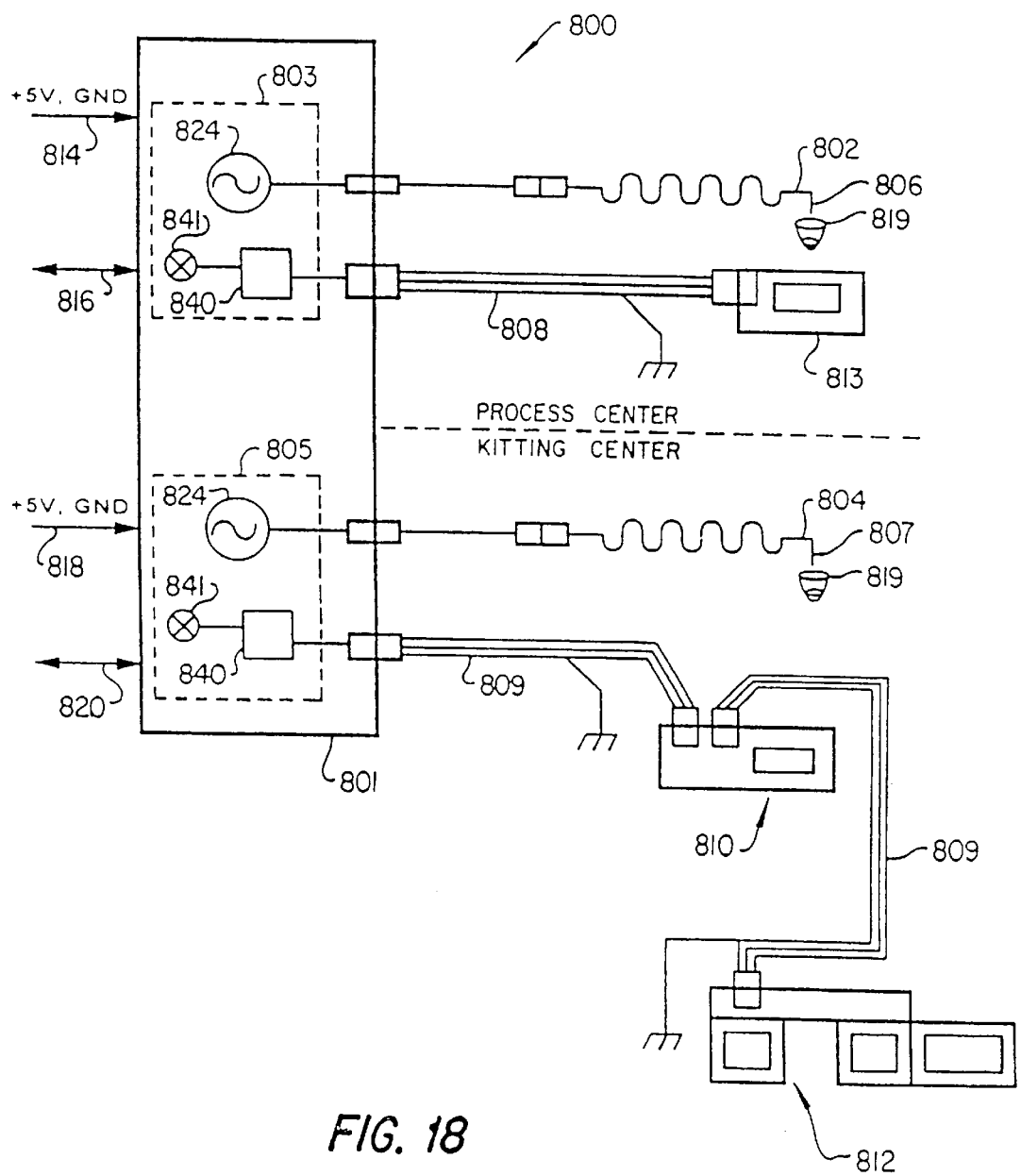
FIG. 18 is a simplified block diagram of the preferred embodiment of the liquid level sensing device of the present invention utilized in connection with an automated analytical system.

FIG. 18 is a simplified block diagram of the preferred embodiment of the liquid level sensing system 800 of the present invention in connection with an automated analytical system. A liquid level sensing circuit board 801 is utilized to monitor pipette probes 806 and 807 (corresponding to the probe of the pipettor mechanism 50 in the process center and the probe 108 of the pipettor mechanism 6 in the kitting center, respectively) when enabled by the automated analytical system computer (not shown), and to stop probe movement when the probes have contacted liquid. The liquid level sensing circuit board 801 mounts in a standard VME card cage, receiving only about +5 V and ground from the VME bus at connections 814 and 818. DC/DC converters (not shown) on the board generate local operating voltages, isolating the board from the VME bus. Control signals to and from the board are routed to system I/O boards (not shown) through connections 816 and 820.

The board 801 contains a process liquid level sensing circuit 803 and a kitting liquid level sensing circuit 805, each completely independent of the other. The process liquid level sensing circuit 803 is dedicated to liquid detections by probe 806 in the process center, and the kitting liquid level sensing circuit 805 is dedicated to liquid detections by probe 807 in the kitting center.

The liquid detection systems in the process center and in the kitting center are essentially identical, and liquid detections occur in the same manner in each system. Therefore, the following description, although describing the liquid detection system in the process center, is equally applicable to the kitting center.

Each of the two circuits 803 and 805 is controlled by a "CALIBRATE" signal from the analytical system computer, and each circuit provides two output signals, "READY" and "DETECT". In operation, CALIBRATE is set except when level sensing is desired. Calibration is performed by an auto-zero circuit 811 described in more detail below. The probe 806 is placed over a liquid sample container 819 (generically representing a container in a reaction vessel 34, a reagent pack 30, or a test sample container 26), preferably immediately over the fluid, and the analytical system computer sets desired gain bits which compensate for the various sizes of sample containers 819. When the circuit is calibrated so that its output signal level is zero, CALIBRATE is deasserted and READY is asserted. The probe is then moved toward the sample container 819 until liquid is encountered, at which time DETECT is set. The analytical system computer receives the DETECT signal, and in turn, signals the motor controller (not shown) to stop vertical probe movement. DETECT remains set as long as the probe 806 is in liquid. When the probe 806 is removed from liquid, DETECT is de-asserted, but will reset if liquid is contacted again. When the probe is withdrawn from the liquid, and fluid sensing is no longer required, CALIBRATE is again asserted. In CALIBRATE mode DETECTS do not occur, being disabled logically, regardless of the analog signal received.

A coax cable 802 carries an RF transmit signal from a low impedance driver signal source 824 on the sensing system circuit board 801 to the probe 806. A receiving antenna 813 is mounted in a stationary position below each rotating carousel, and beneath the area when liquid sensing is desired. In the kitting center, liquid detections occur in several locations; thus antenna 810 and antenna array 812 are mounted below the reaction vessel 34, the reagent pack 30, and the test sample segment container 26. The antennas are connected to the sensing system circuit board 801 by triax cables 808 and 809.

The RF signal is generated by the low impedance driver signal source 824, at a frequency of approximately 125 KHz, and is applied to the probe 806 through the coax cable 802. The RF signal then couples across the air space between the probe 806 and the receive antenna 813, located below the liquid sample container 819. In operation, when the probe 806 is lowered and contacts liquid, the signal from the probe to the antenna increases slightly above that received when the probe is in air. The signal increases because the liquid surface, in effect, becomes part of the transmitting probe, increasing the amplitude of the transmitted signal and redirecting the probe's electromagnetic field toward the receiving antenna 813.

The signal is coupled from the probe 806 to the antenna 813 primarily by an electrical field, which can be mathematically modeled by capacitance. The transmission media may be considered as a small capacitance from the probe 806 to the receiving antenna 813. This type of level sensing may therefore be referred to as capacitance level sensing. Since the electrical field is actually part of an electromagnetic field radiating from the probe, the sensing device may also be referred to as an "RF" (radio frequency) sensing system, although the actual frequency employed is several octaves below standard radio frequencies.

Figure 19:
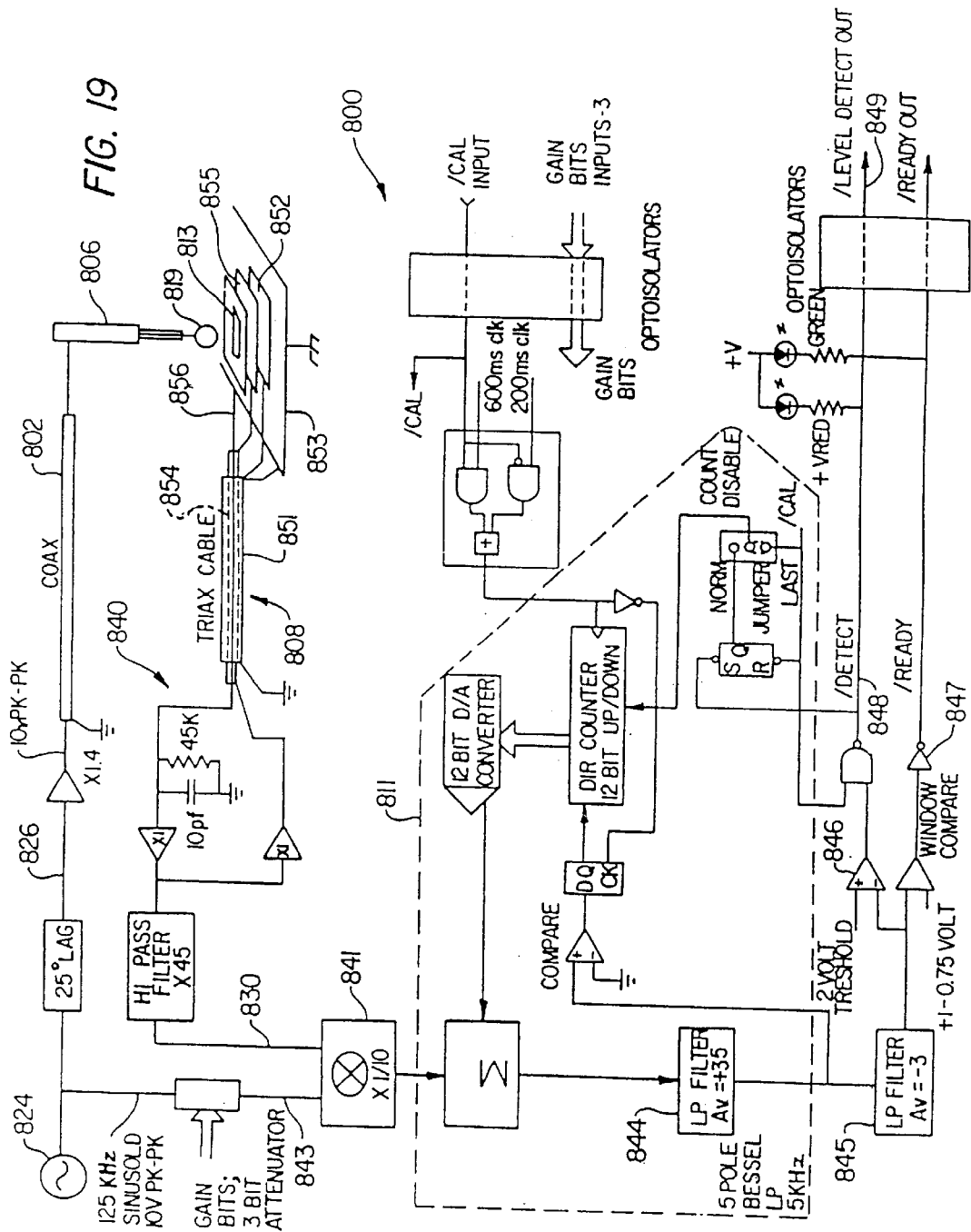
FIG. 19 is a more detailed block diagram of the liquid level sensing system of FIG. 18.

FIG. 19 is a more detailed block diagram of the preferred embodiment of the liquid level sensing system 800 of the present invention in connection with an automated analytical system. The fluid level sensing system 800 includes a synchronous (heterodyne) receiver which includes an amplitude detector 841 and a low pass filter 845. The receiver provides exceptionally narrow-band reception of the electrical signals detected by the antennas. In the synchronous receiver, the amplitude detector 841 multiplies an incoming signal 830 by a reference signal 843 in order to enable the extraction of amplitude information. The signal source 824 also uses the reference signal 843 to generate the transmitted signal 826, therefore both the transmitted and received signals are of substantially the same frequency. The incoming signal must also be substantially in phase with the reference signal.

After the incoming signal 830 is multiplied by the reference signal 843, the output of the amplitude detector 841 is passed through the low pass filter 845 to extract the amplitude information desired. The filter employed in the receiver of the preferred embodiment is a Bessel linear phase filter, which demonstrates minimal or no overshoot, and minimal or no ringing.

The liquid detection system 800 also includes an autozero circuit 811 which enhances signal detection in the preferred embodiment of the present invention. As the distance from the probe 806 to the antenna 813 changes, and as the probe approaches components within the automated analytical system with dielectric constants higher than the surrounding air, the level of the signal reaching the antenna 813 slowly changes. The autozero circuit 811 enables the fluid sensing system 800 to detect fluid with a very small increase in the received signal strength (approximately 0.2 pf) because the increase when the probe contacts liquid occurs very rapidly compared to the change that occurs when moving the probe 806 toward the antenna 813 in air. The autozero circuit 811 nulls out signals which slowly change in amplitude, and reports only rapidly changing signals which exceed a predetermined threshold value.

The autozero circuit timing is such that the output of the circuit is maintained at about zero when the probe 806 is stationary or moving vertically. Changes in signal amplitude which occur slowly, such as those caused by the probe approaching other components of the automated analytical system, are therefore reduced below the predetermined threshold value by the autozero circuit, and are not reported as liquid detections even if the amplitude variations exceed the threshold value. A rapid signal increase may occur in less than 200 microseconds due to fluid contact by the probe. When a rapid signal increase occurs, the autozero circuitry allows the output from low pass Bessel filter 844 to increase. The signal then passes through a second low pass filter 845 and is applied to a 2-volt simple fixed threshold 846. If the signal does not exceed the threshold value, the liquid detection system is maintained in the READY mode at 847. If the increase caused by fluid contact is sufficient to exceed the threshold 846, then a digital bit is output asserting DETECT at 848. At that time, the autozero circuit 811 is disabled. The DETECT signals are routed to the system motor control board at 849, so that when fluid is detected, the motor control board (not shown) can immediately stop the probe movement.

Still referred to FIG. 19, it may be seen that the fluid sensing circuit 803 is referenced to system ground in the immediate vicinity of its associated receiving antenna 813. As noted previously, the circuit 803 is connected to its antenna 813 by the triax cable 808 which, in the preferred embodiment, is about ten feed in total length. The outermost conductor of the triax cable 851, connected to a grounding plate for the antenna 852, and to a system baseplate 853, providing the ground reference for the circuit. The inner shield of the triax cable 854 is a "driven shield". The inner shield 854 is connected at one end to a driven shield plate for the antenna 855, and at the other end to the shield output side of a signal and driven shield circuit 840. The signal from the antenna 813 is carried by the inner conductor 856 to the input of the signal and driven shield circuit 840. The signal and driven shield circuit 840 acts as a buffer which, in turn, drives the inner shield 854. This reduces the effective capacitance of the cable 808 and antenna 813 by a factor of about sixty. The total capacitance of the antenna and ten-food cable is normally about 600 pf. The signal and driven shield circuit 840 effectively reduces this capacitance to about 10 pf. This reduction greatly simplifies the detection of the 0.2 pf increase in signal strength that occurs when the probe 806 contacts liquid.

Bessel filters are used in the transmit circuits for repeatability and in the receive circuit for minimum ringing due to noise spikes, resulting in minimum noise levels within the system. Sharper filters have potentially high overshoots and actually result in a higher noise and ripple level.

Figure 20:
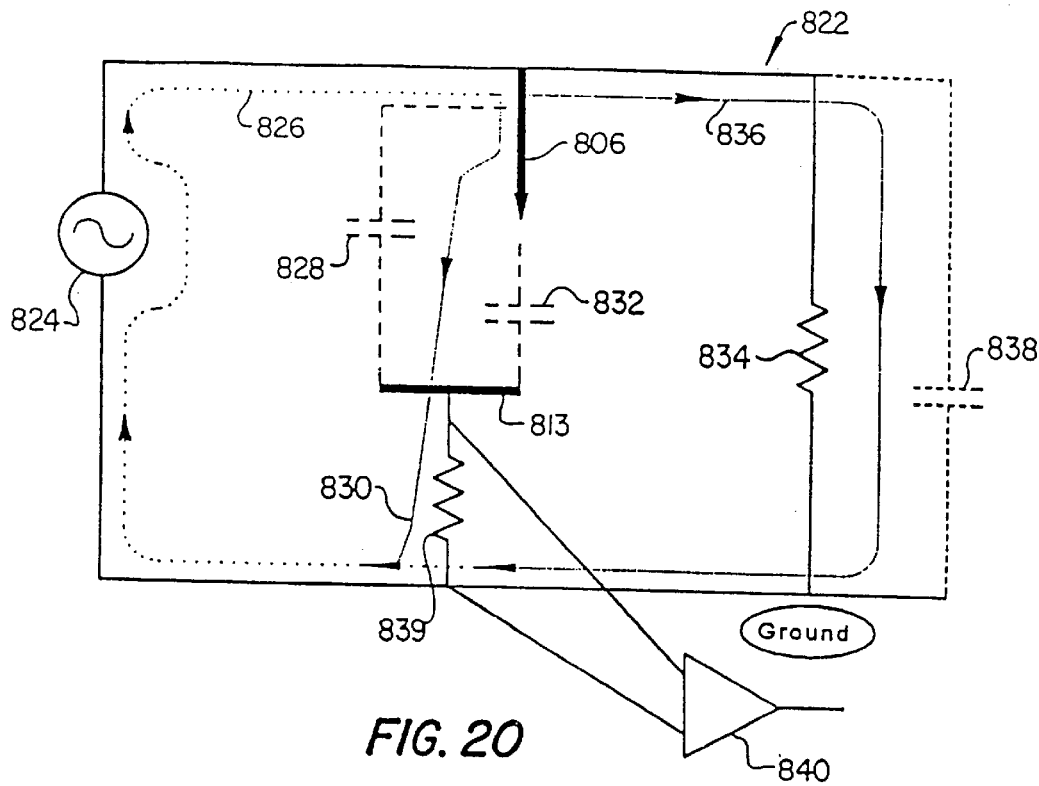
FIG. 20 is a simplified schematic diagram illustrating the current flow in the fluid level sensing system of the present invention.

FIG. 20 is a simplified schematic diagram showing the current flow through the fluid level sensing system 800 of the present invention. Total current 826 flows from the signal source 824 to the probe 806 where it is divided into two paths. In one path, current 836 leaves the probe and flows through diluent to ground, returning to the signal source 824. The diluent is represented by diluent resistance 834 and diluent coupling capacitance 838. Separately, a much smaller current 830 enters the probe 806 and couples through space to the receive antenna 813. Capacitor 828 represents the capacitance of the probe 806 in air. When the probe contacts liquid, additional current flows through the additional fluid capacitance 832, added by the increased surface area of the liquid. The wavelength of the transmitted signal is small compared to the geometries within the automated analytical system, therefore almost all of the coupling from the probe 806 to the antenna 813 is by the electric field. By applying a low impedance transmit signal to the probe and receiving the signal with a separate antenna, shunting effects of conductive diluent in the probe plumbing are avoided. It should be noted that the signal and driven shield circuit 840 (FIG. 19) measures only current from the antenna 813, not the current through the diluent.

Figure 21:
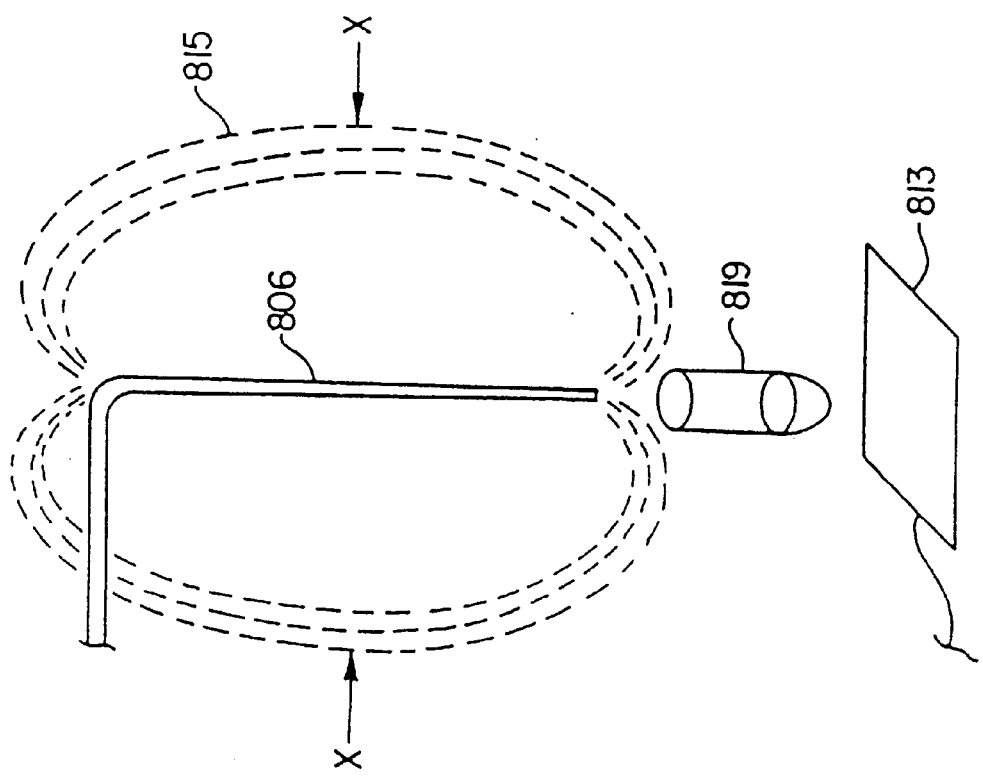
FIG. 21 is an illustration of the geometries between the probe, its electromagnetic field, a liquid sample container, and the antenna when the probe is in air.

FIG. 21 is an illustration of the geometries between the probe 806, its electromagnetic field 815, a liquid sample container 819, and the antenna 813 when the probe is in air. The antenna 813 is positioned directly below the liquid sample container, along the extension of the longitudinal axis of the essentially linear probe 806. As shown in FIG. 21, the electrical signal 815 radiated by the probe in air is strongest on a plane X—X which is perpendicular to the longitudinal axis and at the center of the probe's length. There is a null Y in the electrical signal along the extension of the longitudinal axis. Therefore, when the probe 806 is in air, very little signal reaches the antenna 813.

Figure 22:
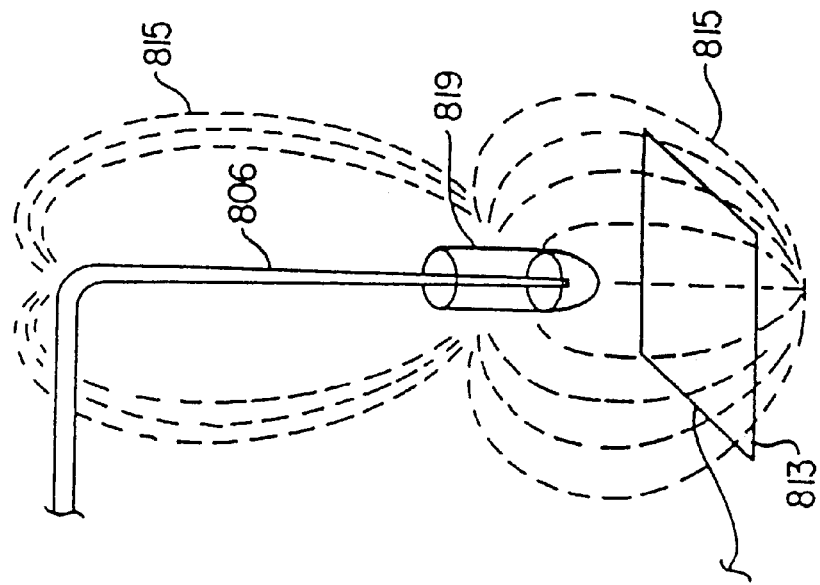
FIG. 22 is an illustration of the geometries between the probe, its electromagnetic field, a liquid sample container, and the antenna when the probe contacts liquid.

FIG. 22 is an illustration of the geometries between the probe 806, its electromagnetic field 815, a liquid sample container 819, and the antenna 813 when the probe contacts liquid. A greater signal level is radiated along the extension of the longitudinal axis than from the probe in air (see FIG. 21). Therefore, the signal level received by the antenna 813 rises significantly when the probe 806 contacts liquid.

Figure 23:
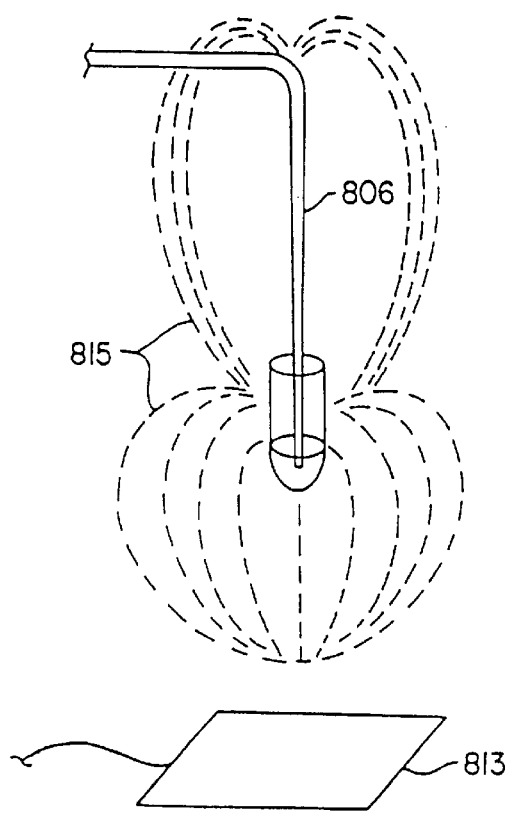
FIG. 23 is an illustration of the geometries between the probe, its electromagnetic field, a liquid sample container, and the antenna when the probe has contacted liquid and the distance from the probe/liquid combination to the antenna is too great to trigger a detection.

FIG. 23 illustrates that even the electromagnetic field 815 generated by the probe in liquid may be insufficient to generate enough signal at the antenna 813 to trigger a detection if the distance from the liquid sample container 819 to the antenna 813 is too great. This condition may arise when short sample cups are used in the sample segment container 600 (FIG. 36). therefore, the sample segment container 600 is equipped with fluid level sensing sleeves 608 mounted directly below the positions where short sample cups are inserted. The sensing sleeves 608 may be constructed of aluminum or any other electrically conductive material.

Figure 24:
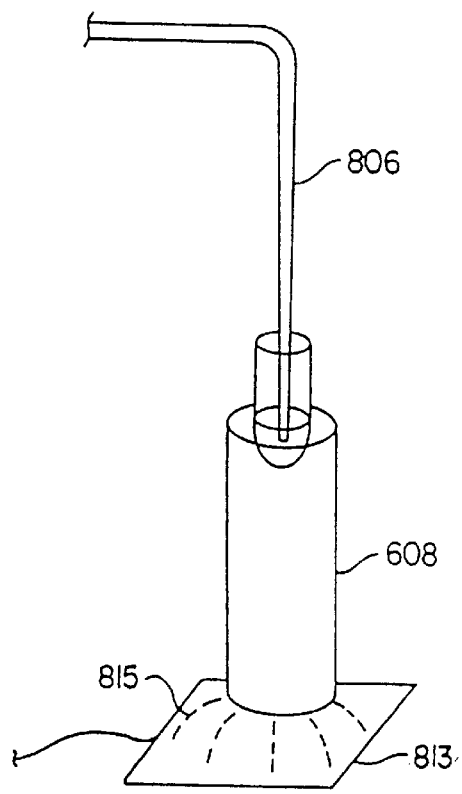
FIG. 24 is an illustration of a sensing sleeve which functions to channel the electrical signal from the probe/liquid combination to the vicinity of the receiving antenna.

As shown in FIG. 24, the sensing sleeve 608 functions to channel the electrical signal 815 from the probe/liquid combination to the vicinity of the receiving antenna 813. The sleeves 608 are mounted at a height at which the top of the sleeve approximately coincides with the top of the liquid in the sample cup. If the sleeve is mounted too high, it may cause false fluid detections due to channelling of the signal from the probe in air. If the sleeve is mounted too low, fluid detections will be missed because the sleeve will not adequately function to channel the electrical signal to the antenna 813.

Figure 43:
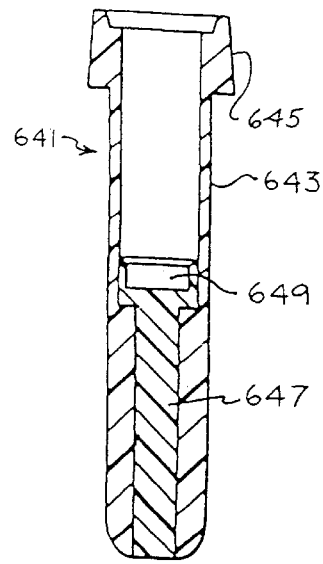
FIG. 43 is a cross-sectional view of a long test sample cup adaptor with tube in place.
Figure 44:
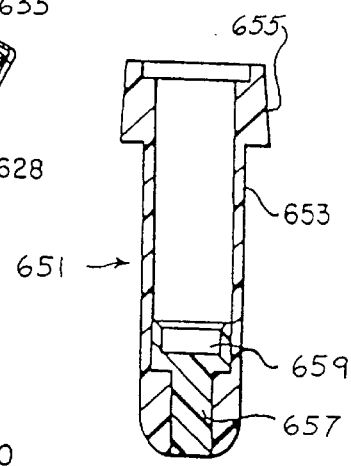
FIG. 44 is a cross-sectional view of a short test sample cup adaptor with tube in place.

FIGS. 43 and 44 are cross-sectional, elevational view of a long Vacutainer® tube 641 and a short Vacutainer® tube 651 which are used in the tube segment 626 shown in FIG. 40, all described below in more detail. Each tube 641, 651 has a conductive core 647, 657 formed from an electrically conductive material which may be, for example, aluminum. A sample cup for holding the liquid test sample conforms to the shape of the inside of the Vacutainer® tubes 641, 651 and is positioned therein so that the liquid test sample is also container within the reservoirs 649 and 659 of the conductive cores 647 and 657, respectively, also described in more detail below. When the probe contacts the surface of the liquid in the sample cup, the core 647, 657 conducts the electrical signal from the probe/liquid combination to the vicinity of the receiving antenna 813 mounted below.

Figure 25:
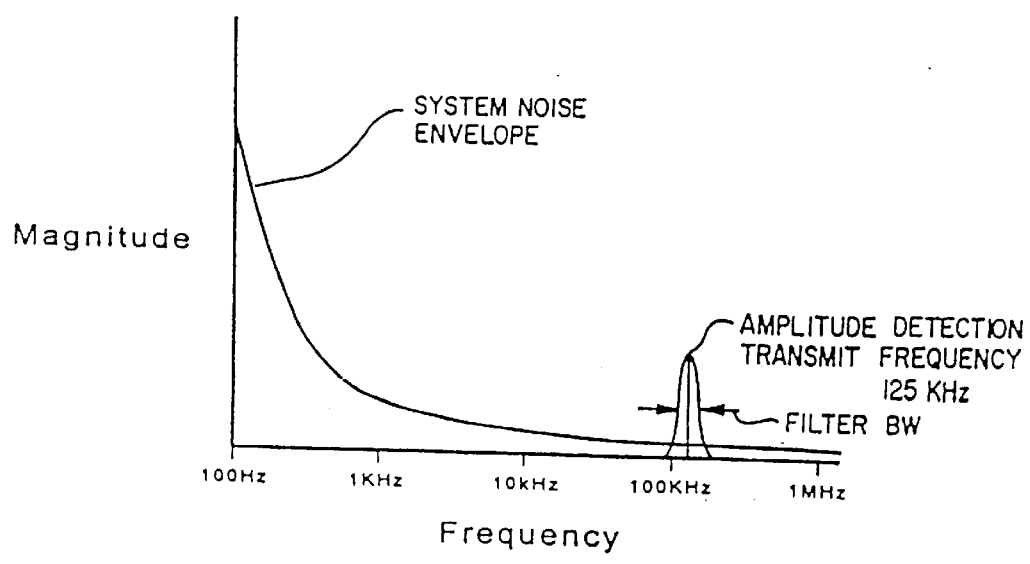
FIG. 25 is a graphical representation of system noise level versus signal frequency.

FIG. 25 is a graphical representation of system noise level versus signal frequency. The graph illustrates the importance of having a high center frequency (125 KHz) along with a narrow filter band width (250 Hz). The system noise level peaks at lower frequencies, and decreases as frequency increases. Thus, it is advantageous to operate at higher frequencies with narrow band width to reduce noise.

It is to be understood that the liquid level sensing system of the present invention can be utilized in any automated instrument where liquid level sensing is desired.

SYRINGE BUBBLE FLUSHER

Figure 26:
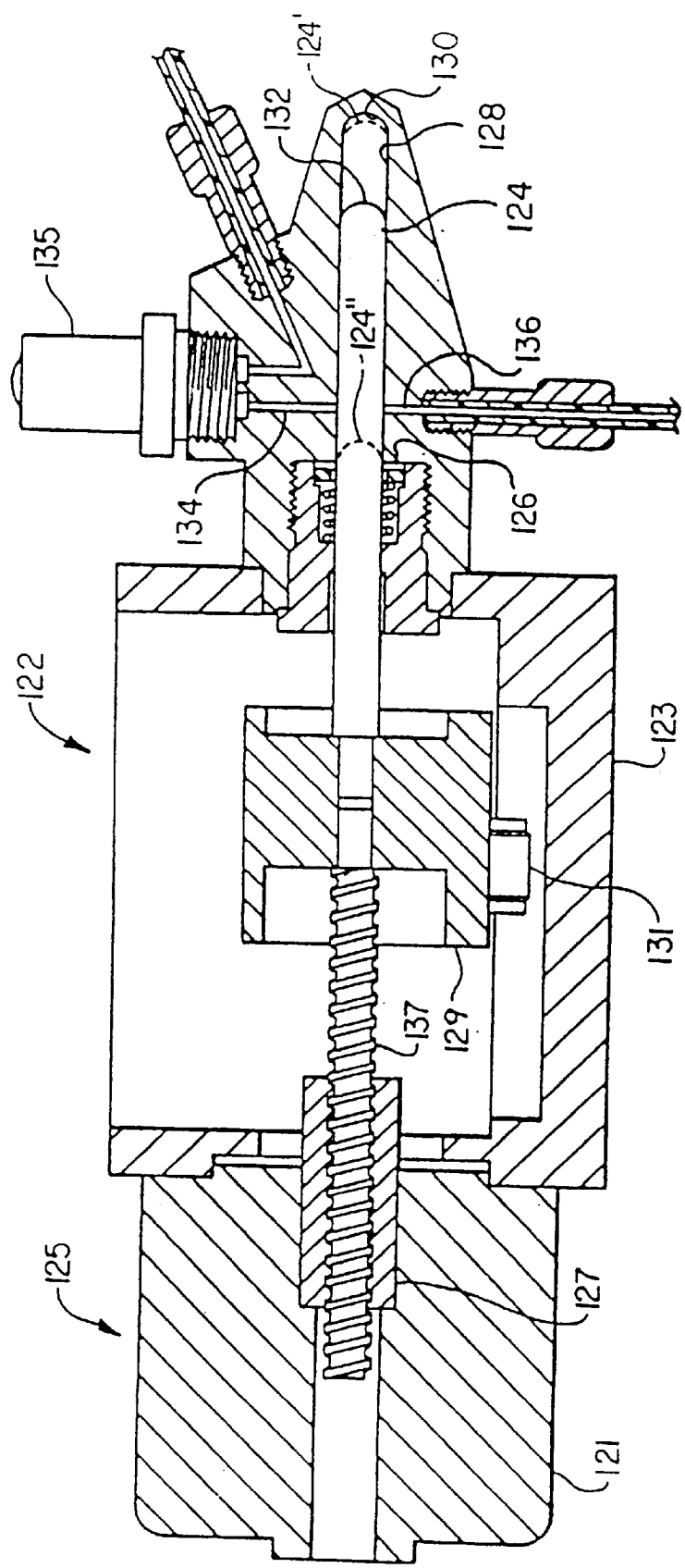
FIG. 26 is a cross-sectional side elevational view of an automatic bubble flushing syringe of the automated analytical system.
Figure 27:
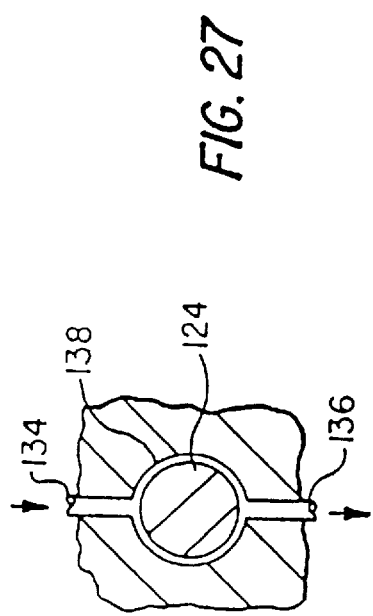
FIG. 27 is a sectional end view in isolation of the piston and bore of the automatic bubble flushing syringe of FIG. 26.
Figure 28:
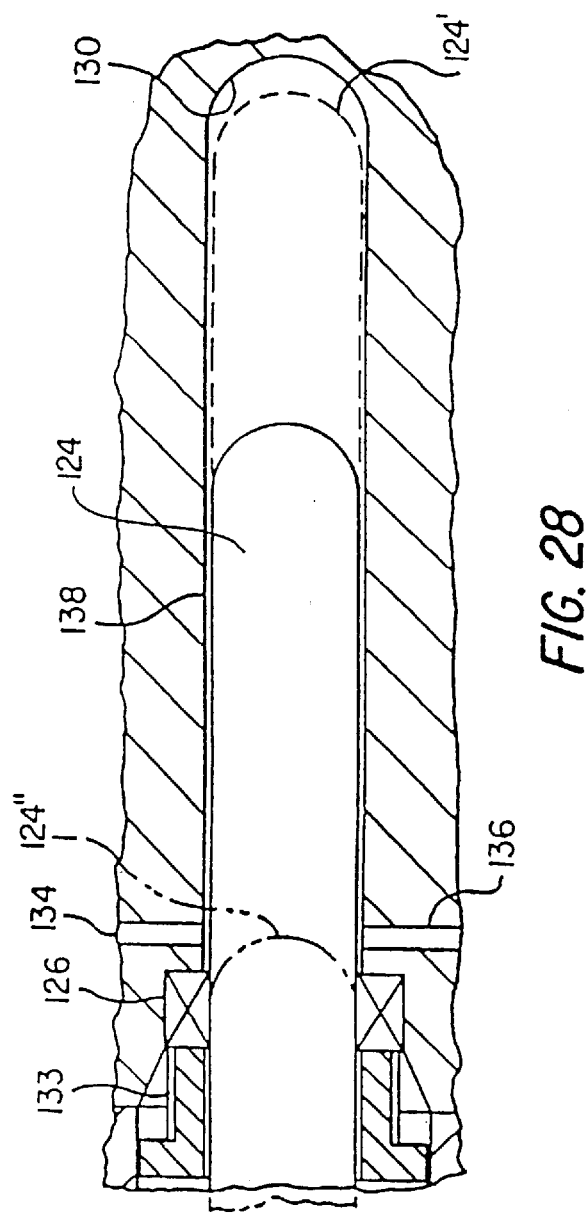
FIG. 28 is a sectional side view in isolation of the syringe bore end portion of the automatic bubble flushing syringe with the reciprocating piston near the end of travel toward the bore end portion and a phantom position within the bore illustrating the piston withdrawal to the outward extension.

Referring now to FIGS. 26, 27, and 28 in combination, there is shown syringe 122 which aspirates and dispenses fluids to the various pipetting mechanisms and has the ability to automatically flush bubbles from the syringe 122. The ability of diagnostic instrumentation to accurately perform an assay is critically dependent on the precision and accuracy with which the syringe 122 can aspirate and dispense reagents and samples through the open ended tip of a pipette. The precision and accuracy of a syringe is severely degraded by the presence of small air bubbles inside a syringe. Bubbles, unfortunately, are all too common and are difficult to remove or avoid. Syringe 122 avoids these problems by automatically flushing bubbles completely out of the fluidics system. The syringe 122 is configured such that a piston 124 reciprocates through a seal 126 and into a close-fitting bore 128. The end of the bore 120 is closed. The piston 124 has a piston end 132 which approximates the geometry of the closed bore end 130. An annulus 138 exists between the piston 124 and bore 128. A fluid entry port 134 and a fluid exit port 136 are positioned axially about 180 degrees apart and are located near the seal 126. Pressurized fluid is introduced to the fluid entry port 134 under the control of a two-way solenoid valve 135. The fluid flows into the annulus 138, round both sides of the piston 124, and then exits through the fluid exit port 136. This crossflow flushes bubbles from the area near the seal 126.

Still referring to FIGS. 26, 27, and 28 in combination, the piston 124 reciprocates inside the bore 128 while the crossflow of fluid through the annulus 138 near the seal 126 continues. This reciprocation causes high fluid flow velocities in the annulus 138 between the piston 124 and the bore 128. The high velocity of fluid flow dislodges any bubbles that my be adhering to the piston 124 or bore wall 128. The inward stroke of the piston 124 pushes these dislodged bubbles to the crossflow area where they are swept out of the syringe 122 by the crossflow of fluid. The piston end 132 and the bore end 130 have similar geometric shapes. When the piston 124 strokes to its full inward extension, it comes very close to the bore end 130. Any bubble that may be stuck on the bore end 130 is disrupted and dislodged. Likewise, the bubbles from the bore end 130 and the piston end 132 are dislodged and pushed to the crossflow area where they are swept out of the syringe 122 by the crossflow. The sequence of reciprocating the piston while crossflowing occurs can be automatically executed any time by the system apparatus. It is to be understood that the syringe 122 according to the instant invention can be used in any other automated analytical system or apparatus requiring a syringe which can aspirate and dispense fluids with precision and accuracy.

Referring still to FIGS. 26, 27, and 28, once the fluid leaves the fluid exit port 136 of the syringe 122, it must travel through tube fittings and tubing (not shown) into a probe 106 and out the probe tip 108. It is through the open end of the probe tip 108 that the aspirating and dispensing of reagents actually occurs. Any bubbles trapped between the syringe 122 and the probe tip 108 will also degrade performance. It is therefore necessary to use zero dead volume tubing fittings on the tubing between the syringe 122 and the probe 106, and a zero dead volume valve 135 to ensure that the bubbles are flushed out of the entire fluidic system therebetween. When the syringe 122 operates in the bubble flushing mode according to the present invention, the initial withdrawal velocity of the piston 124 from the at rest or home position 124' is slower than the velocity of the piston as it approaches a total withdrawal position 124". This type of manipulation of the piston action in relationship to the end of the bore avoids high vacuum and bubble creation within the bore 128. On the other hand, the piston 124 can be withdrawn from the home position 124' at full speed in order to expedite removal of preformed bubbles in the end of the bore 128. After such bubble flushing procedures, the valves are closed so that fluids can be aspirated. When the syringe 122 operates in the dispensing mode, the solenoid valve 135 is opened to meter predetermined quantities of liquid for dispensing out of the probe tip 108.

Referring more specifically to FIG. 26, when the syringe 122 operates in the aspirating mode after the bubble flushing mode described above, the piston 124 is placed in the home position 124' and the solenoid valve 135 is closed. With the solenoid valve 135 closed, the fluidics system is closed except for the probe tip 108. The fluid in the fluidics system is a tryss fluid, or hydraulic fluid medium, which preferably will not react or mix with the sample or reagent to be aspirated. Examples of hydraulic fluid mediums include, but are not limited to, deionized water and saline solution, and are selected based on the properties of the fluid to be aspirated. The probe tip 108 is positioned within the fluid to be aspirated. The piston 124 is then moved from the home position 124' to a position representing the amount of fluid to be aspirated. The withdrawal of the piston 124 causes the hydraulic fluid medium to withdraw from the probe tip 108, thereby drawing the desired fluid into the probe tip 108. The probe tip 108 is then positioned to a location for expelling the fluid just aspirated. The fluid is expelled by moving the piston 124 back to the home position 124'. Residual aspirated fluid is flushed from the fluidics system by positioning the probe tip 108 in a location for disposing of fluids, opening the solenoid valve 135, and forcing the hydraulic fluid medium back through the fluidics system. Once the fluidics system has been flushed, the solenoid valve 135 is closed and the syringe 122 continues to aspirate fluids.

Referring again generally to FIGS. 26, 27, and 28, in combination, the syringe 122 configuration can be, but is not intended to be limited to, about 8.3" long, 3.5" wide and about 2.7" deep. A linear actuator 125 is mounted to the frame 123. An actuator motor 121 spins a nut means 127 into which a mating lead screw 137 is screwed. The lead screw 137 is clamped to the coupler 129 which has a bearing 131 mounted on its bottom side. The bearing 131 runs in a groove in the frame 123. Since the coupler 129 is rotationally constrained by the bearing 131, the coupler 129 reciprocates when the liner actuator motor 121 spins the nut means 127 and the piston 124 which is clamped into the coupler 129, thus reciprocating the piston 124 through the seal 126. The piston 124 reciprocates through the seal 126 which is springloaded and carried by a polyethylene wear ring 133, the seal 126 being comprises of an O-ring over the polyethylene wear ring. The clearance between the piston and the bore is small and, according to a preferred embodiment, from between about 0.002" and about 0.008". When piston 124 reciprocates, very high flow rates are generated in the annulus 138 between the piston 124 and the bore 128. These high flow velocities flush bubbles in the bore 128 to the seal area where they are swept out of the syringe 122 by the cross flow. Zero (0) dead volume fittings are positioned between the syringe 122 and the tip release means to ensure that bubbles flushed out of the syringe 122 have no place to lodge as they are swept down the communicating tube and out probe the tip 108. Although the syringe operates effectively regardless of its orientation, the preferred embodiment points the plunger 124 downwardly using gravity to facilitate movement of the bubbles toward the cross-flow region between the fluid entry port 134 and the fluid exit port 136.

It is to be understood that the syringe of the present invention can be used in any situation where the precise manipulation of fluids is desired, whether the syringe is operated manually or by an automated instrument, including, but not limited to, precision aspirating and dispensing of fluids such as found in many medical diagnostic instruments and devices requiring precision analytical pipetting, particularly small volumes of fluid. In addition, the inclusion of a second valve downstream of the syringe converts the syringe into a precision positive displacement pump.

The syringe of the present invention is particularly useful with an automated analytical system which is capable of simultaneously performing two or more assays on a plurality of test samples in a continuous and random access fashion, such as the system described in greater detail herein. In particular, the automated immunoassay analytical system apparatus of the invention can be viewed as a microprocessor based system of integrated subassemblies with different groups of assays being run through separate and changeable software modules. The microprocessor bases system uses robotic arm pipettors with two degrees of freedom and bidirectional rotating carousels to process samples. Critical assay steps such as incubations, washes and specimen dilution are performed automatically by the instrument as scheduled.

CLOSURE AND MIXING OF REAGENTS

Referring to FIGS. 29 and 30, one embodiment of a reagent container 30 (see also FIG. 4A) stores reagents to be aspirated by a pipettor through an opening 30a in the top of the reagent container 30. The reagent container 30 has a cover 31 which pivots between an open and closed position on a pin 37 mounted on a support flange 30b of the reagent container 30. The pin 37 can include biased spring means to facilitate movement of the cover 31 between opened and closed positions. For example, such spring means can be a hinge formed from a stretched material, such as stretched plastic, to provide the desired bias. The cover 31 extends radially from the other side of the pin 37 forming a tab 33 as a lever arm for the cover 31.

The apparatus and method of the present invention is capable of controlling the opening acceleration of the reagent container closure systems to reduce or prevent contamination between reagent containers, and to prevent the loss of reagents by, for example, randomly sprayed or airborne liquid reagents, typically in the form of droplets, which may otherwise result from abrupt opening of the containers. According to this embodiment, the system apparatus comprises a linear actuator (not shown) positioned at an opening and closing station (not shown) on the front end carousel 4. The linear actuator reciprocates a plunger 35 having a notched lower end 35' for engaging the tab 33. When the linear actuator extends the plunger 35 downwardly, its notched lower end 35' engages the tab 33 to open the cover 31. When the actuator withdraws the plunger 35, its notched lower end 35' pulls the tab 33 up to close the cap 31. It is to be understood that the other closure systems described below are controlled in a similar fashion to reduce or prevent evaporation and the invasion of contaminants into the reagent containers.

The opening 30a of the reagent container 30 can also be fitted with a closure rather than making the cap 31 an integral part thereof. Referring more specifically to FIG. 33, a capped-closure for a reagent container (not shown) is indicated generally at 435, and comprises a closure 430 and a cap assembly 431 connected to the closure 430 by a hinge 437. The closure 430 fits tightly on the reagent container to prevent evaporation and has an opening 432 in the top through which a pipettor aspirates reagents. The cap assembly 431 comprises a cap 434 to which the closure 430 is hinged and a lever-tab 433 mounted on the top of the cap 434. The cap 434 has a cap closure 438 which fits over and closes the opening 432 of the closure 430 to prevent evaporation of the reagents and a stopper 436 fitting within and plugging the opening 432 to further prevent evaporation of the reagents and the invasion of contaminants when the cap assembly 431 is partially closed. One end of the lever-tab 433 is mounted on the cap 434, while the other end extends therefrom to provide a lever arm that opens the cap assembly 431 when pressed down. When the cap assembly 431 is closed completely to cover the opening 432 during extended periods of non-use or while being handled, the cap 434 provides a "hard seal" preventing evaporation from the reagent container. When, however, the cap assembly 431 is partially closed to cover the opening 432 as described above during operation of the analyzer for example, the stopper 436 of the cap 434 provides a "soft seal" that still prevents evaporation and the invasion of contaminants. It is to be understood that the other capped-closures described herein provide the same functions, e.g., cap 31 (FIG. 30) above and capped-closures indicted generally at 450 and 460 (FIG. 32) described in more detail as follows.

According to a preferred embodiment (FIGS. 31–35), a regent pack 31' is shown in FIGS. 31 and 32, FIG. 32 being a section taken along A—A of FIG. 31 and adding capped-closures 450 and 460. The reagent pack 30' supports three reagent containers 441 and an open bulk liquid container 443 within its walls 445. The reagent pack 30' also comprises a stabilization cover 458 fitting over the shoulders of the containers 441, 443 and a mounting bracket 447 seating on the reagent pack carousel 32 in the same fashion as the regent containers 30 shown in FIG. 4A. The containers 441, 443 have openings 442 and 444, respectively, on which the capped-closures 450 and 460, respectively, are seated as described above. The capped-closure 450 for the reagent containers 441 also comprise a closure 452 fitting on the opening 442 and a cap assembly, or cap, indicated schematically at 454 and pivotally hinged on the closure 452 by a pin 461 (FIG. 34). A stopper 454(a) on one end of the cap 454 fits within an plugs the opening in the top of the closure 452, and the other end 454(b) of the cap 454 functions as a tab lever. The capped-closure 460 also comprises a closure 462 and a cap assembly (not shown). Both capped-closures 450, 460 are functionally equivalent to the capped-closure 435 described above, e.g., the stopper 454(a) provides both a hard seal as shown and a soft seal (position not shown) that prevent evaporation and invasion of contaminants. The cap 454 is also shown in an open position 454' and a locked-open position 454", both of which provide adequate access for a pipettor to aspirate reagents therefrom. The cap 454 is preferably biased by a spring (not shown) into the locked-open position to prevent the cap 454 from closing inadvertently as a result of, for example, movement of the front end carousel 4. It is to be understood, however, that the cap 454 is not limited to these positions as shown.

Referring more specifically to FIGS. 34 and 35, a cap actuator station is shown generally at 464 in a first perspective side elevational view in FIG. 34 and a different perspective side elevational view in FIG. 35. The capped-closure 450 associated with the reagent containers 441 to be aspirated (not shown) are rotated into position below the cap actuator station 464 by the reagent carousel 32 (FIG. 32) to be opened or closed as previously described. The cap actuator station 464 comprises a housing 466 and a drive motor 468 mounted thereon. The housing 466 has a bracket 470 for mounting the cap actuator station 464 in a fixed position above the reagent carousel 32 (FIG. 3). The cap actuator station 464 further comprises opening pins 472 extending through a pin block 473 and being actuated by the drive motor 468 to move downwardly against the tab lever 454(b) of the cap 454 causing it to pivot on the pin 461 to pull the stopper 454(a) out of the closure 452 and flip the cap 454 from the closed position as shown in FIG. 35 to the desired open position 454' as shown in FIG. 34. The cap actuator station 464 further comprises a cap actuator 474 which includes three valve-shaped heads shown in an inactive position with the opening pins 272 extending downwardly from the pin block 473. The heads of the cap actuator 474 are driven by the drive motor 468 downwardly against the cap 454 to return it from the open position 454' as shown in FIG. 34 to the closed position shown in FIG. 35. This downward motion or positioning is also used in conjunction with the rotational motion of the reaction carousel 32 to cause the heads of the cap actuator 474 to drag along the top of the cap 454 to force it down to the closed position. Alternatively, the cap actuator 474 can be a single valve-shaped head having suitable dimensions for closing the cap assembly 431 of the capped-closure 435 (FIG. 33) or the cap 31 (FIG. 30). It should be understood that the present invention is not limited by the details of construction disclosed in connection with the cap actuator 474 and the correspondingly operable capped-closure 435, 450. For example, a separate cap 454 can be used for each reagent container 441 rather than being joined together so that they can be separately operated. The cap actuation station 464 can have opening pins 472 and cap actuators 474 wherein each of the individual pins and valves can operate independently to open the individual capped-closures 450 selectively or simultaneously.

In operation, the reagent carousel 32 rotates the desired reagent containers 441 (FIG. 32) to an opening position below the cap actuator station 464 for the opening pins 472 to contact the tab lever 454(b) to open the cap 454 to its substantially vertical open position 454' as shown in FIG. 34 and described above. The reagent carousel 32 then rotates the reagent containers 441 to a locking position under the cap actuator station 464 avoiding contact with the opening pins 472, but driving the heads of the cap actuator 474 into frictional contact with the top end of the cap 454 to push it from the open position 454' to the locked-open position 454" (FIG. 32) where the cap 454 is locked in place by an internal spring mechanism (not shown) as described above. In order to close the cap 454 of the capped-closure 450, from either the open position 454' or the locked-open position 454", the reagent carousel 32 moves the reagent containers 441 so that the top of the cap 454 is moved into frictional contact with either the opening pins 472 or the heads of the cap actuator 474 partially lowered to drag along the top of the cap 454 and overcome the force of the internal spring, thereby returning the cap 454 to a partially closed position or the soft seal position with the stopper 454(a) in the opening of the closure 452. Alternatively, the heads of the cap actuator 474 can move the cap 454 from the partially closed position down to the soft seal position, or farther down to the hard seal position in which the capped-closure 450 is completely closed. It is to be understood that the opening pins 472 can also close the cap 454 to form the soft or hard seal without assistance from the cap actuator 474 to prevent evaporation of the reagents and the invasion of contaminants.

According to a preferred embodiment, the acceleration of the opening of the cap 454 is controlled by the heads of the cap actuator 474 which contact the upper surface of, and reciprocate in an upward direction with, the cap 454 during the process of opening the capped-closure 450 as described above. When reciprocally contacting the upper surface of the cap 454, the cap actuator 474 provides downward resistance thereagainst to control the upward or opening acceleration thereof while, at the same time, allowing the cap 454 to open to the desired open position for access to the liquid reagent in the reagent container 441 by a pipette probe.

It is to be understood that other variation of the capped-closure 450 and operation of the cap actuator station 464 are contemplated without departing from the teachings of the present invention. For example, the internal spring can be associated with the pin 461 of the cap 454 or with the hinge 437 of the cap assembly 431 (FIG. 33), to effect closing of the caps 454, 434, respectively, without the assistance of the downward force of the opening pins 472 or the cap actuator 474. For example, the caps 454, 434 can be spring-biased to the closed position, with the opening pins 472 remaining in contact with the tab lever 454(b), 433, respectively, subsequent to the opening operation as described above to maintain the caps 454, 434 in an open position to allow aspiration of reagents from the reagent container 441 with a pipette probe. Once the pipette probe has been withdrawn from the reagent container 441, the opening pins 472 move in an upward direction away from tabs 454(b), 433 to allow the caps 454, 434 to return to their evaporatively sealed closed positions. The spring-biasing can be accomplished by a stretched material, such as stretched plastic, tension springs, and the like, whereby the desired bias can be ascertained by one skilled in the art apprised of the foregoing considerations. As would be understood by one skilled in the art, such embodiment can be employed, for example, in an Abbott IMx® analyzer or TDx® analyzer wherein means for movement of a reagent pack mounted therein are not provided.

In addition, a pipette probe transfer mechanism can either be located at a remote location or station removed from the cap actuator station 464, thereby requiring movement of a reagent pack 30' to such pipette probe transfer mechanism for access of reagents in a reagent container 441 by the pipette probe. Alternatively, the transfer mechanism can be integrated with the cap actuator station 464, so that movement or repositioning of the reagent pack 30' is unnecessary. Moreover, the cap actuator station 464 is not intended to be limited for use with the rotational movement of a carousel as described herein. For example, a reagent pack can be mounted or otherwise positioned on a non-concentric or linear conveyor system, whereby such non-concentric system reciprocates with a reagent pack to facilitate the opening and closing of a capped-closure as described herein. Similarly, the cap actuator station can be utilized in conjunction with carousels and non-concentric conveyor systems which are not necessarily in the horizontal plane.

The Kitting Center is treated as one pipette block. Carryover experiments have shown that a post wash of at least about 2 ml is sufficient to clean the probe to a carryover level of 1 ppm or less when sample is kitted first followed by wash and pipetting of reagents. Total wash following sample should be about 4 ml total wash before next kitting activity. Contamination of the reagent bottle following sample will come from the outside of the probe. This is reduced to insignificant levels by wash to waste cup, e.g., 200 to 1,000 µl, followed by from between about 1 ml to about 2 ml wash to the wash cup.

In order or insure consistent, rapid resuspension and continued mixing of reagents with minimal operator involvement, the reagents are mixed automatically each time a new reagent pack is added to the reagent carousel, and periodically during instrument operation. This automated mixing can be accomplished by a back and forth motion of the reagent carousel with asymmetric pauses and is complete within approximately 1–2 minutes. The carousel acceleration, velocity, distance moved, and pause-asymmetry are optimized to yield the most rapid reagent resuspension without foaming or bubble formation for the range of fill volumes used on the instrument.

Automated reagent mixing provides the following benefits. The operator need not manually mix (e.g. by inversion or shaking) reagents which have been stored prior to their placement on the instrument. This allows the reagents to be loaded onto the instrument in less time and with less involvement of the operator. There is less tendency for reagents to foam or form bubbles with automatic mixing than with manual mixing such as inversion. Foam and bubble formation are detrimental to instrument function and can negatively impact assay performance. Automated mixing insures that reagents are always mixed sufficiently and that they are mixed consistently. Occasional automatic mixing during instrument operation keeps reagents in a consistent suspension, and makes it unnecessary for the operator to periodically remove reagent packs in order to mix the reagents. In some circumstances, automated mixing can dissipate bubbles present at the start of mixing. A detailed description of kitting and process activities according to the invention are presented later herein for FPIA procedures for a phenobarbital assay; and for MEIA procedures for a CEA assay.

SAMPLE CONTAINER SEGMENTS

Figure 36:
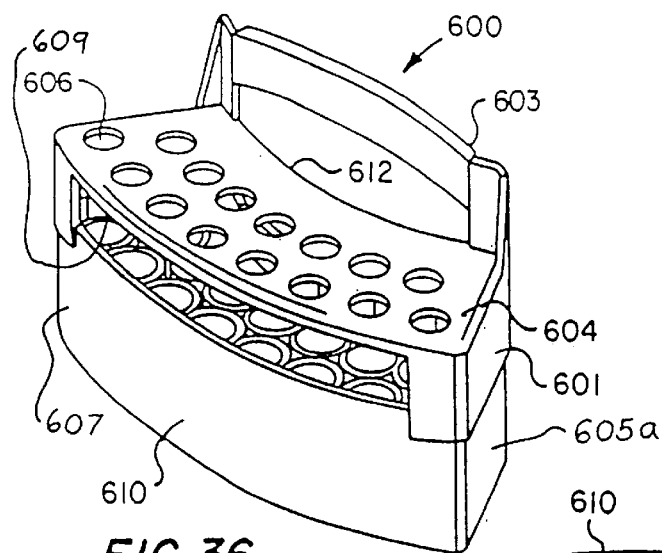
FIG. 36 is a perspective view of a test sample container segment assembly.
Figure 37:
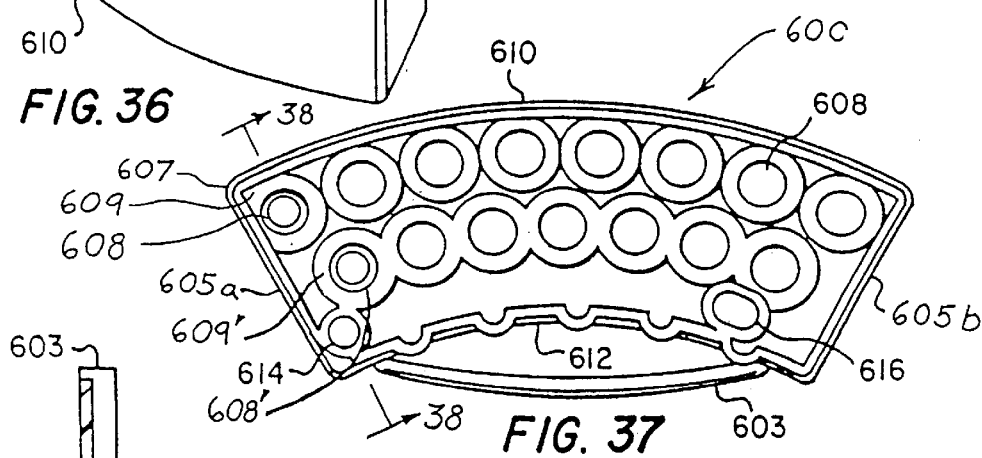
FIG. 37 is a bottom view of the test sample container segment assembly of FIG. 36.
Figure 38:
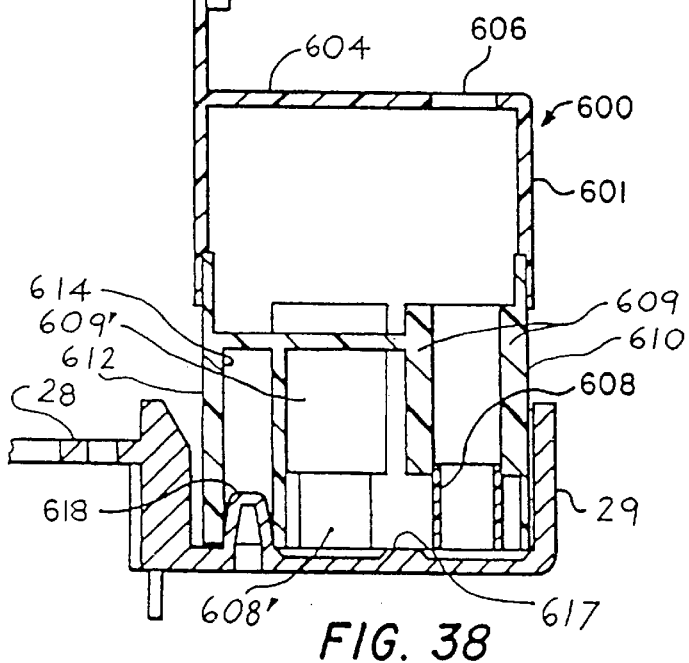
FIG. 38 is a cross-sectional view in isolation of the sample carousel with a mounted test sample container segment assembly also in cross-section.

Referring now to FIGS. 36, 37 and 38, a sample container segment is shown generally at 600 in a perspective view. The sample container segment 600 comprises a frame 601, a handle 603 connected to the top of the frame 601, and base 607 supporting the frame 601. The handle 603 extends above the frame 601 to facilitate handling by an operator. The base 607 is formed by arcuate vertical sidewalls, an outer sidewall 610 and an inner sidewall 612, closed by endwalls 605a and 605b. The frame 601 is formed by a horizontal shelf 604 having the same arcuate shape defined by the sidewalls 610, 612 and supported at both ends by legs seated on the top of the base 607. A plurality of container openings 606 are formed in the shelf 604 for receiving test sample containers such as, for example, the one indicated generally at 620 in FIG. 39 having an opening expanding diametrically to a skirt 624 for supporting the container 620 on the shelf 604 and described in more detail below. The base 607 further comprises a plurality of tubular sleeves 609 positioned therein to hold the bottom portion of the test sample container 620 in place within the sample container segment 600. Thus, the test sample containers 620 are inserted through the container openings 606 into the tubular sleeves 609 and supported therein by the skirt 624 resting on the horizontal shelf 604. In one preferred embodiment of the invention, a plurality of the sleeves 608 which operate as antennas for sensing the presence of liquid in the containers 620 are supported by and below each one of the tubular sleeves 609 at the bottom of the base 607. Referring more specifically to FIGS. 37 and 38, individual antenna sleeves 608 and 608' are shown positioned below the individual tubular sleeves 609 and 609'. Antenna sleeves for the other tubular sleeves are not shown. Referring now more specifically to FIG. 37, a bottom view of the sample container segment 600, the bottom of the base 607 is also arcuate in shape as defined by the sidewalls 610, 612 and shares a common radius center therewith. The bottom of the base 607 is also bounded by the endwalls 605a,b which lie on radius lines sharing the same common radius center.

Referring more specifically to FIG. 38, a cross-sectional view, in isolation, if the sample container segment carousel 28 with the sample container segment 600 mounted on a carousel through 29 which circumvents the periphery of the carousel 28 is shown. The carousel trough 29 comprises an inner wall mounted on the carousel 28 and an outer wall, both sharing the same common radius center with and sufficiently spaced to receive the sidewalls 610, 612 of the base 607 of the sample container segment 600. The carousel trough 29 also comprises a support rib 617 concentrically formed in the bottom of the carousel trough 29 and having a flat surface supporting the base 607 of the sample container segment 600 resting thereon. The carousel trough 29 further comprises a plurality of alignment pins 618 projecting upwardly from the bottom of the carousel trough 29 and spaced along the carousel trough 29 at a fixed distance from the common radius center near the inner wall of the carousel trough 29. Sequential pairs of alignment pins 618 are used to position sample container segments 600 side-by-side around the carousel in the carousel trough 29. Referring now to both FIGS. 37 and 38, the base 607 of each sample container segment 600 has slots for receiving the alignment pins 618, i.e., a circular slot 614 positioned near the intersection of the inner sidewall 612 and the endwall 605a and an elongated slot 616 positioned near the intersection of the inner sidewall 612 and the endwall 605b. The elongated slot 616 is adapted to adjust for distance variations between the alignment pins 618 paired to support a sample container segment 600.

Figure 39:
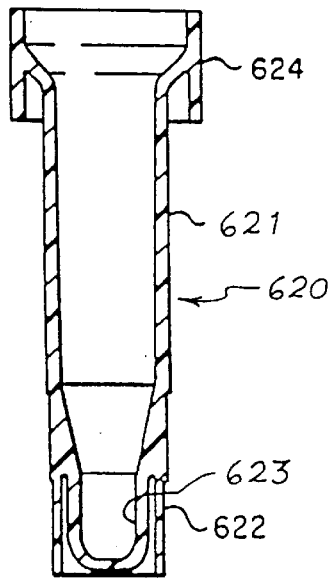
FIG. 39 is a cross-sectional view of a modified sample cup with skirts.

Referring now to FIG. 39, there is illustrated a test sample container 620 of the present invention, shown in a cross-sectional view. It is to be understood that the test sample containers contemplated according to the present invention include, but are not limited to, Vacutainer® tubes, test tubes, cuvettes, vials, sample cups and the like, all of which can be of varying sizes and dimensions. The test sample container 620 comprises a main body 621, tubular in shape, having an outer diameter slightly smaller than the container openings 606 in the sample horizontal shelf 604 of the sample container segment 600 shown in FIG. 36. The body 621 of the test sample container 620 opens up to the skirt 624 described above which has a diameter larger than the container openings 606 in the sample container segment 600. The inside bottom of the body 621 of the test sample container 620 tapers to form a reservoir 623 in which the test sample is contained. The outside bottom of the body 621 surrounding the reservoir 623 forms a base 622 generally cylindrical in shape and adapted to fit with the antenna sleeves 608 shown in FIG. 38. When the test sample container 620 is positioned in the sample container segment 600, the surface of the liquid test sample contained in the reservoir 623 is below the top of the sleeve 608 which functions as an antenna to detect the presence of the surface for liquid level sensing as described above.

Referring now to FIGS. 36–39 in combination, it can be seen how the sample container segments 600 of the present invention facilitates the loading of test samples for the automated analytical instrument 2 (shown in FIG. 1). The body 621 of the test sample container 620 is inserted within the container opening 606 of the sample container segment 600, and the skirt 624 of the test sample container 620 rests on the mounting shelf 604 of the sample container segment 600. In this manner, the sample container segment 600 supports the test sample container 620. The operator uses the handle 603 to position the sample container segment 600 in the carousel trough 29 so that the pairs of alignment pins 618 fit into the slots 614, 616 to locate the sample container segment 600 at a specific radial and angular location on the carousel 28. The sample container segment 600 positions the test sample containers 620 at a fixed location on the test sample carousel 28 so that the test sample carousel 28 can rotate the test sample containers 620 selectively to the station at which the pipette probe tip 108 (shown in FIG. 7) accesses the reservoir 623 within the test sample container 620 with only lateral and vertical movement. Additional sample container segments 600 are used with the test sample carousel 28 in a similar manner, each one carrying any number of test sample containers. For example, the test sample carousel 28 is preferably adapted to receive six of the test sample container segments 600 adapted to receive either six or ten of the test sample containers 620, wherein the number and sizes of test sample containers 620 will vary with each test sample container segment 600. It should be understood that the present invention is not limited to the number of test sample segments 600 used on the carousel 28, or the number of test sample containers 620 supported by each one.

In operation, the operator may instruct the system to place the test sample carousel 28 into a hold phase for loading and unloading of test sample container segments 600. Such instruction by the operator causes the kitting process to be suspended after the completion of the kitting cycle in progress. Once loading and unloading is complete, a second instruction will cause the kitting process to resume. The test sample container 620 may be placed into the sample container segments 620 before or after the sample segment containers 620 are placed on the test sample carousel 28. Preferably, each sample container segment 600 includes an identifying number or bar code which is read by a scanner in the automated analytical instrument 2 (shown in FIG. 1). Also, it is preferred that each test sample container 620 have an identifying number or bar code on the upper skirt 624 which is read by the scanner in order to facilitate the automatic analytical instrument 2 in locating a specific test sample. The automated analytical instrument 2 scans the sample container segments 600 and test sample containers 620 as the carousel 28 rotates those components to the scanning means (not shown) of the automated analytical instrument 2. However, when a "stat" test is ordered, the automated analytical instrument 2 scans all sample container segments 600 until it finds the one containing the "stat" test sample. When the stat kitting cycle is completed, the normal kitting process is continued causing the test sample carousel 28 to return to its original position. The status of onboard test samples is audited through a data entry screen 8 (shown in FIG. 1) of the automated analytical instrument 2. The operator uses the audit to determine which test sample container segments 600 have been emptied and can be removed from the carousel 28.

Figure 40:
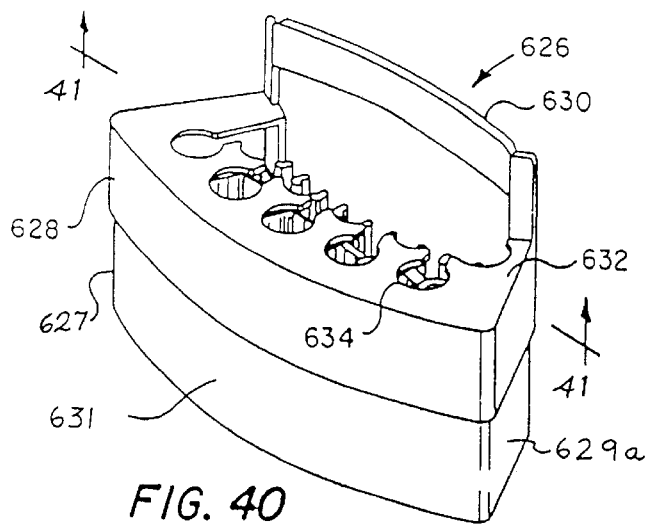
FIG. 40 is a perspective view of a short test sample Vacutainer® tube segment assembly.
Figure 41:
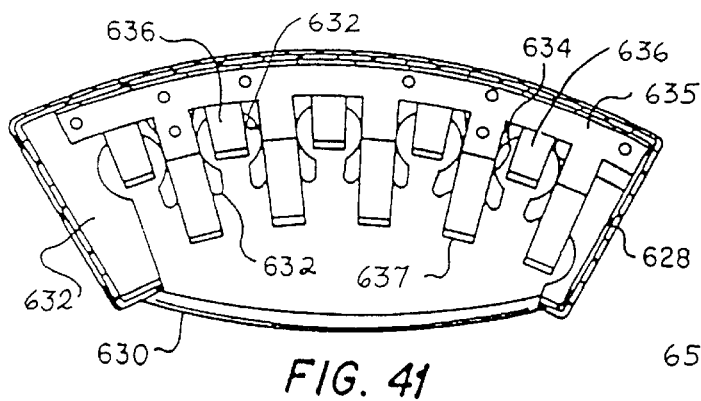
FIG. 41 is a top cross-sectional view of the short test sample Vacutainer® tube segment assembly taken along the line A—A of FIG. 40.
Figure 42:
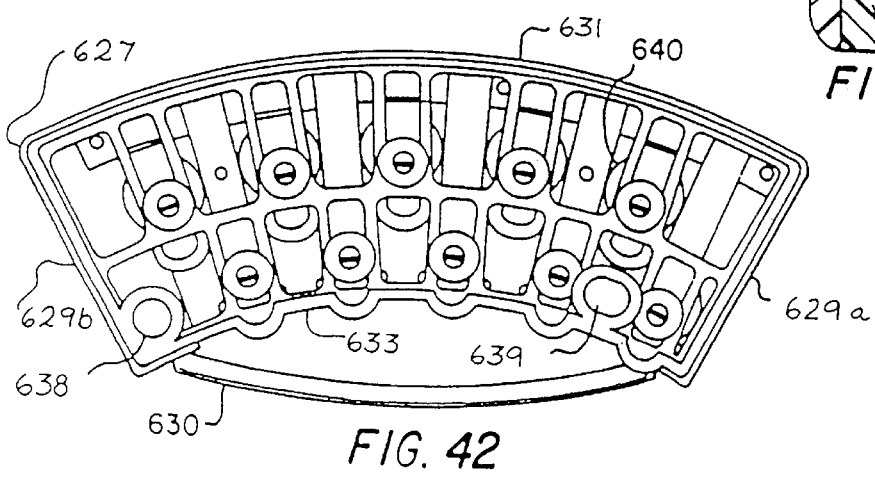
FIG. 42 is a bottom view of the short test sample Vacutainer® tube segment assembly of FIG. 40.

Another embodiment of a sample container segment is shown generally at 626 in a perspective view in FIG. 40, a sectional view on line A—A of FIG. 40 in FIG. 41, and a bottom view in FIG. 42. This particular sample container segment 626 is designed to hold Vacutainer® tubes, such as those shown generally at 641 and 651 (FIGS. 43 and 44, respectively), hereinafter referred to as the "tube segment 626". The tube segment 626 comprises a frame 628, a handle 630 connected to the top of the frame 628, and a base 627 supporting the frame 628. The handle 630 extends above the frame 628 to facilitate handling by an operator. The base 627 is formed by arcuate vertical sidewalls, an outer sidewall 631 and an inner sidewall 633, closed by endwalls 629*a* and 629*b*. The frame 628 is formed by a horizontal shelf 632 having the same arcuate shape defined by the sidewalls 631, 633 and positioned on top of the base 627. A plurality of tube openings 634 are formed in the shelf 632 for receiving the Vacutainer® tubes 641, 651. Leaf springs 636 are mounted below the horizontal shelf 632 adjacent each tube opening 634 for holding each Vacutainer® tube in place. An arcuate bracket 635 is mounted on the inside of the outer sidewall 631 to support a plurality of holding arms 637 extending radially inwardly between pairs of Vacutainer® tubes in order to provide additional support and positioning within the tube segment 626. The base 627 of each tube segment 626 has slots for receiving the alignment pin 618, i.e., a circular slot 638 positioned near the intersection of the inner sidewall 633 and the endwall 629*b*, and an elongated slot 639 positioned near the intersection of the inner sidewall 633 and the endwall 629*a*. These slots 638, 639 are adapted to adjust for distance variation between the alignment pin 618 in the same manner as for the sample container segment 600 described above. As can be seen, the tube segment 626 is constructed and positioned in the same manner on the sample container segment carousel 28 as in the sample container segment 600. The two segments 600, 626 are used interchangeable on the test sample carousel 28 and operate in the same fashion with the exception that the tube segment 626 does not include a component similar to the antenna sleeves 608, the equivalent of which are formed alternatively in the sample container itself, i.e., Vacutainer® tubes 641, 651. Despite this dissimilarity, the tube segment 626 functions in the same manner when the Vacutainer® tubes are positioned therein.

Referring now to FIGS. 43 and 44, there is illustrated a long Vacutainer® tube 641 and a short Vacutainer® tube 651, respectively, shown in a cross-sectional view. The Vacutainer® tubes 641, 651 are essentially identical with the exception of the length of the tubes. The Vacutainer® tubes 641 and 651 comprise a tube body 643 and 653, respectively, with an outer diameter slightly smaller than the tube openings 634 of the tube segment 626 in FIGS. 40–42. The body 643 of the large Vacutainer® tube 641 has a diameter from about 0.40 inches to about 0.65 inches, and a length from about 3.0 inches to about 4.0 inches. The body 653 of the small Vacutainer® tube 651 has a diameter from about 0.40 inches to about 0.65 inches and a length from about 2.0 inches to about 3.0 inches. The Vacutainer® tubes 641 and 651 also comprise a skirt 645 and 657, respectively, adjacent the opening thereof having an outer diameter greater than the openings 634 of the Vacutainer® segment 626. Conductive cores 647 and 657 are formed inside the bottom of the body 643, 653 of each tube 641 and 651, respectively, the lower ends forming part of the bottom of the tubes 641, 651 and the upper ends forming reservoirs 649 and 659, respectively, for the test samples. When the Vacutainer® tubes 641, 651 are positioned in the tube segment 626, the surface of the liquid test sample contained in the reservoirs 649, 659 is below the top of the conductive cores 647, 657 which function as antennae to detect the presence of the surface for liquid level sensing as described above. In this manner, liquid level sensing can be performed according to the system and method disclosed above to determine the level of liquid test samples in the Vacutainer® tubes 641 and 651 held by the Vacutainer® segment 626.

Referring now to FIGS. 40–41 in combination, it can be seen how the Vacutainer® tubes 641 and 651 operate with the tube segment 626 of the present invention to facilitate the loading of test samples for the automated analytical instrument 2 (shown in FIG. 1). The Vacutainer® tube 641, 651 is inserted into the tube opening 634 of the tube segment 626, the skirt 645, 655 of which rests on the horizontal shelf 632 of the tube segment 626. The leaf spring 636 holds the inserted Vacutainer® tube 641, 651 in the tube segment 626 which the holding arms 637 maintain the Vacutainer® tubes 641, 651 in a specific position in relationship to the tube segment 626. Thus, when the tube segment 626 is loaded onto the test carousel 28, the Vacutainer® tubes 641, 651 are not only positioned to a uniform height, but also are positioned at a specific location on the test carousel 28. In this manner, the carousel 28 rotates the Vacutainer® tubes 641, 651 selectively to the station at which the pipette probe tip 108 (shown in FIG. 7) of the automated analytical instrument 2, aspirates test samples from the reservoirs 649, 659 thereof. In a preferred embodiment, the Vacutainer® segment 626 and each skirt 645, 655 of the Vacutainer® tube 641, 651 has an identifying number of bar code that the automated analytical instrument 2 can use to find and identify particular samples, in the same manner as the sample container 620 and the sample container segment 600 in FIGS. 36–39.

REACTION VESSEL AND LOADERS

Referring to FIGS. 45A–C, a top view, cross-sectional view and end view of a reaction vessel is shown generally at 34. The reaction vessel 34 comprises a platform 144 having side edges 143 and 145 tapering at one end to form a front edge 147 semicircular in shape. The platform 141 also comprises a support skirt 149 generally tubular in shape extending below the platform 141 from an opening therein adjacent the semicircular front edge 147. The support skirt 149 is sized to secure the cuvette 140 in the reaction vessel 34. The support skirt 149 can be, for example, a press-fit aperture within which the cuvette 140 is inserted. A vertical tab 151 is formed at the opposite end of the platform 141 between the side edges 143, 145 and extends above the top surface of the platform 141.

The platform 141 also comprises containers or wells 142, 144, 146, 148, 150, 152, and 154, all extending below the platform 141 from openings therein. These containers or wells have specific shapes and locations suitable for storing reagents, samples, buffers, or dilution liquids necessary for the operation of the analytical system. Regardless of the arrangement, the container or well adjacent the vertical tab 151, in this case the well 154, comprises a reaction vessel tab 153 formed in the bottom of the well and externally downwardly therefrom. The reaction vessel tab 153 is used by the transfer station 42 (FIG. 4A) to engage the reaction vessel 34 for movement from the reaction vessel carousel 36 to the process carousel 34 as described in more detail above.

Figure 46:
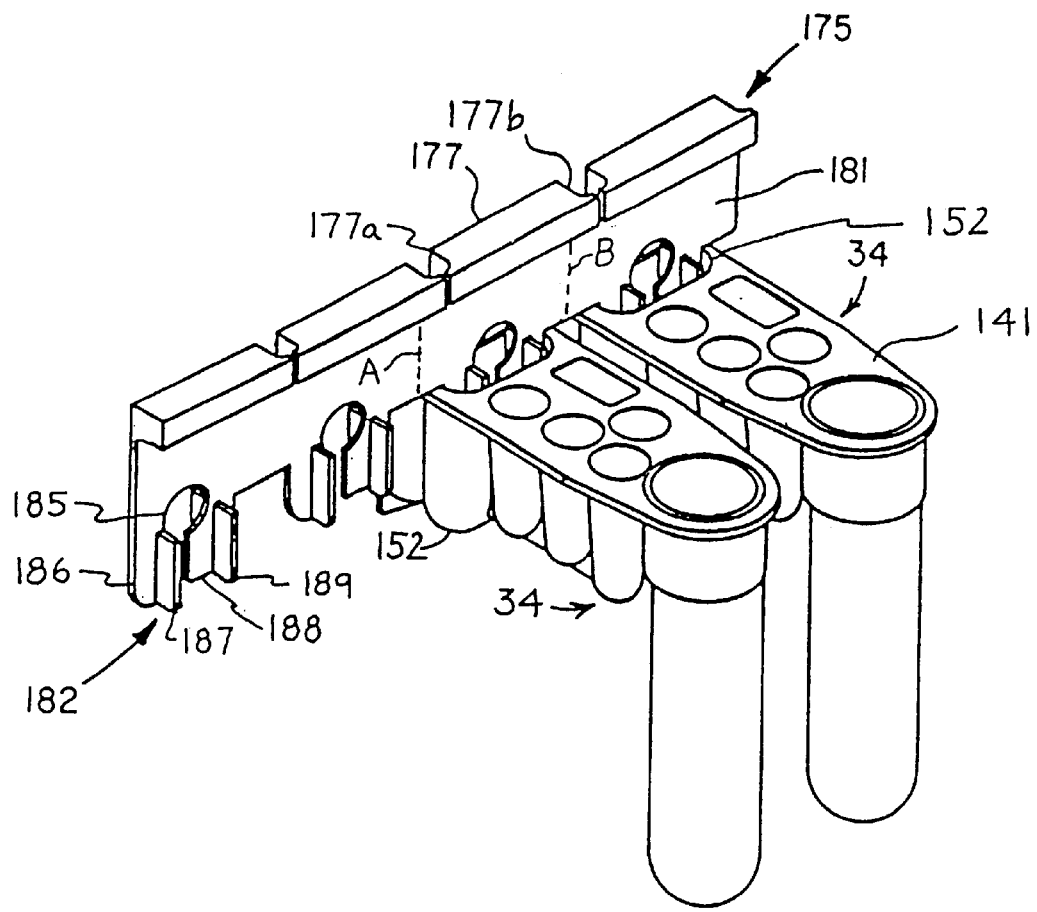
FIG. 46 is an isometric view in section of the reaction vessel loading device illustrating the device holding to vessels and means for mounting other vessels.
Figure 47:
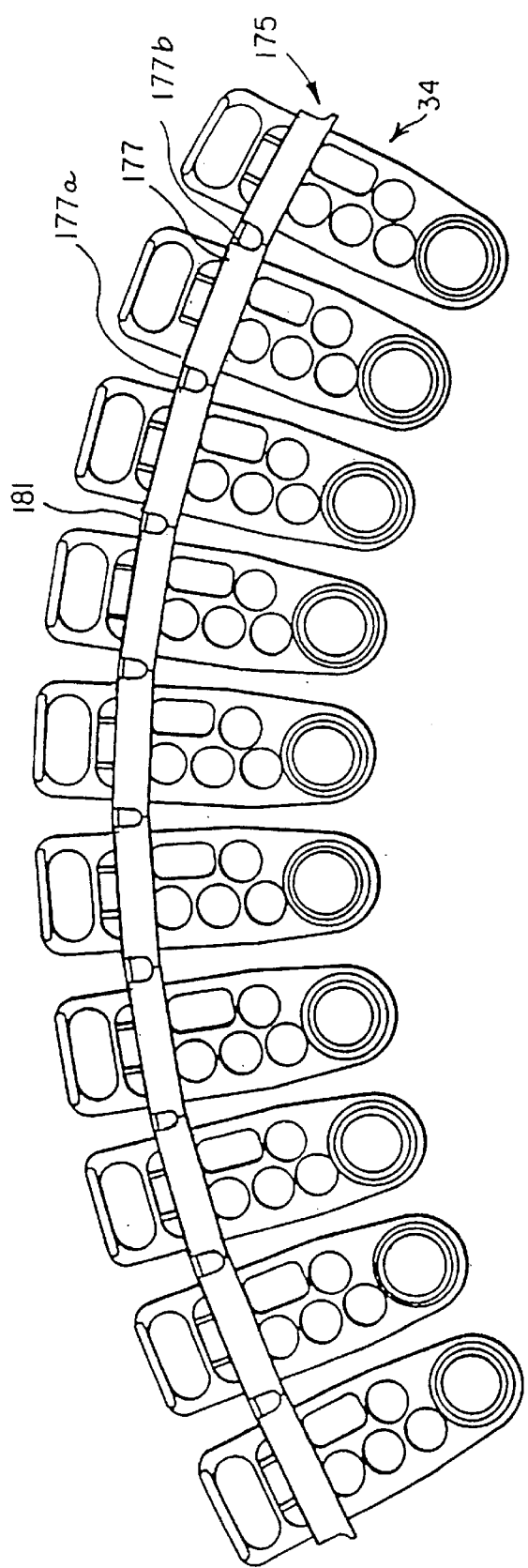
FIG. 47 is a top view of the reaction vessel loading device presented in an arc which matches the radius of the reaction vessel carousel, the loading device having mounted thereon ten reaction vessels.

Referring now to FIGS. 46 and 47, an isometric view and a top view of a loading strip 175 for supporting a plurality of reaction vessels 34 to be positioned in the reaction vessel carousel 36 is shown. The loading strip 175 is shown in section in FIG. 46 to be supporting two reaction vessels 34, and in FIG. 47 as supporting ten reaction vessels 34 for purposes of illustration only, recognizing that the loading strip 175 can be configured to accommodate any number of reaction vessels 34. The loading strip 175 comprises a continuous strip 181 having a plurality of ledge segments 177 formed on the upper edge and a plurality of mounting tabs indicated generally at 182 formed on the lower edge for supporting the reaction vessel 34. The mounting tabs 182 are formed by a pair of resilient legs 186 and 188 extending downwardly from the lower edge of the continuous strip 181 and having an aperture 185 therebetween shaped in the form of a key-hole. The mounting tabs 182 also include a pair of fins 187 and 189 each extending perpendicularly through the resilient legs 186 and 188, respectively, adapted to fit snugly within the well 152 of the reaction vessel 34. Each ledge segment 177 is centered above the mounting tab 182 so that the ends 177*a*, 177*b* thereof extend beyond the outer edges of the resilient legs 186, 188. The ledge segments 177 are aligned end to end forming a gap between each one of sufficient size to allow the continuous strip 181 to bend on either side of the reaction vessels 34 as indicated by dashed lines A and B. When the continuous strip 181 is bent, each ledge segment 177 maintains the rigidity of that portion of the continuous strip 181 supporting the reaction vessel 34 by the mounting tab 182 to prevent it from slipping off the mounting tab 182. Referring more specifically to FIG. 47, the gaps formed between each ledge segment 177 are sufficiently large to allow the continuous strip 181 to become sufficiently arcuate for positioning the reaction vessels 34 in the circular reaction vessel carousel 36.

In operation, the reaction vessels 34 are mounted on the loading strip 175 by inserting the mounting tabs 182 into the wells 152 of the reaction vessels 34. Each pair of resilient legs 186, 188 and fins 187, 189 fit snugly within the walls of the well 152 of the reaction vessel 34 to hold the reaction vessels 34 on the loading strip 175. When all the reaction vessels 34 are positioned on the loading strip 175, the operator loads them simultaneously on the reaction vessel carousel 36, thereby minimizing the amount of time that the reaction vessel carousel 36 is in a hold position. The operator loads the reaction vessels 34 on the reaction vessel carousel 36 by bending the loading strip 175 into an arc concentric with that portion of the reaction vessel carousel 36 in which the reaction vessels 34 are being positioned. When the reaction vessels 34 are inserted into the corresponding slots or positions on the reaction vessel carousel 36, the reaction vessels 34 are secured sufficiently tightly therein so that the mounting tabs 182 will slip out of the wells 152 when the operator lifts up the loading strip 175 away from the carousel 36.

Figure 48:
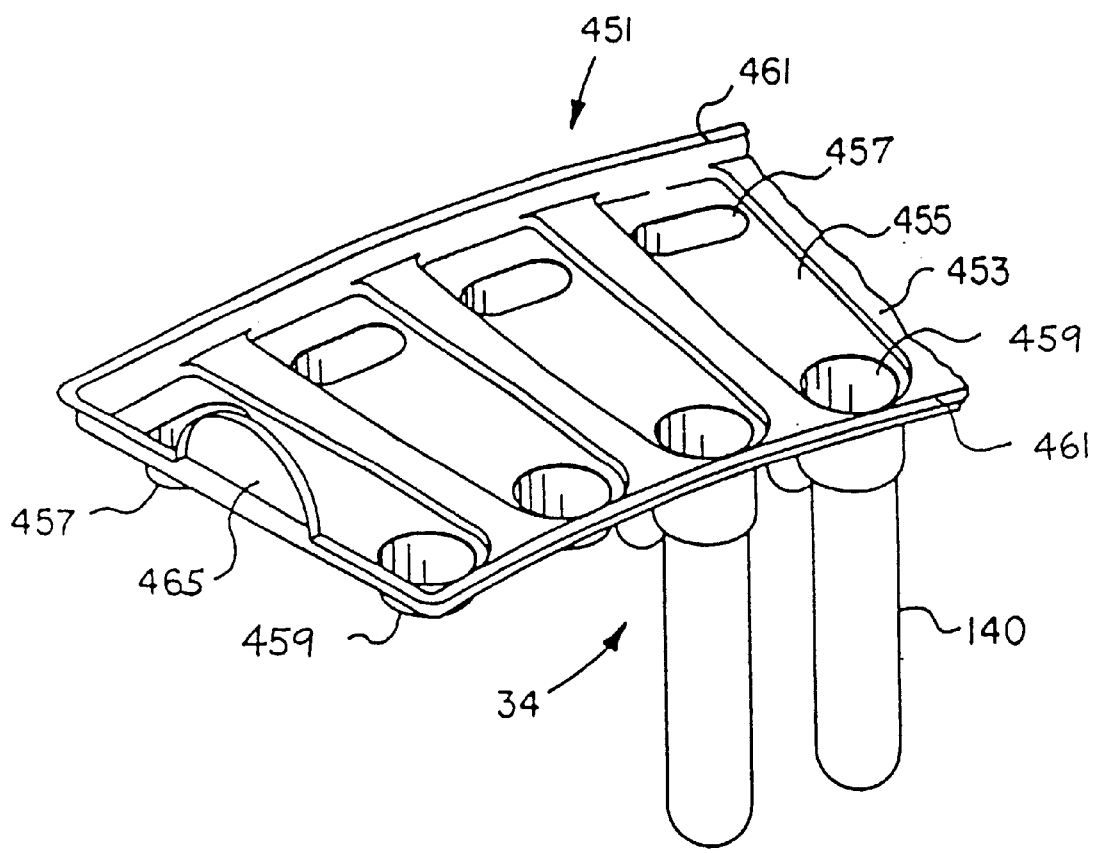
FIG. 48 is an isometric view in section of the reaction vessel loading device illustrating the loader mounted with two reaction vessels and means for mounting other reaction vessels.

Referring now to FIG. 48, there is shown an isometric view of a reaction vessel loading device 451, in section, having two reaction vessels 34 mounted thereon. The loading device 451 is preferably manufactured from a semi-rigid plastic, or the like, and is generally formed in a shape corresponding to the radius of curvature of the reaction vessel carousel 36 (shown in FIG. 4A). The loading device 451 has a planar surface 453. Extending below the planar surface 453 are a plurality of recessed planar surfaces 455 which have a shape generally conforming to the shape of the platform 141 of the reaction vessels 34 (shown in FIGS. 45A–C). Extending below the recessed planar surfaces 455 are cuvette plugs 459, which are sized and located for insertion into the cuvette 140 of the reaction vessel 34. Also extending below the recessed planar surfaces 455 are well plugs 457 sized for insertion into the well 152 of the reaction vessel 34, as shown, but also including plugs (not shown) which are sized and located for insertion into the other wells 142, 144, 146, 148, 150, or 154 of the reaction vessels 34. The well plug 457 and cuvette plug 459 are tapered downward from the recessed planar surfaces 455, thereby providing ease of insertion or removal of the well 152 and cuvette 140 of the reaction vessel 34. Extending upward around the outer parameter of the planar surface 453 is a continuous elevated rim 461, the top of which is substantially flat and parallel to the planar surface 453. At either end of the loading device 451 are handling fins 465 which are parallel to, and extend upward from, the elevated rim 461.

Figure 49:
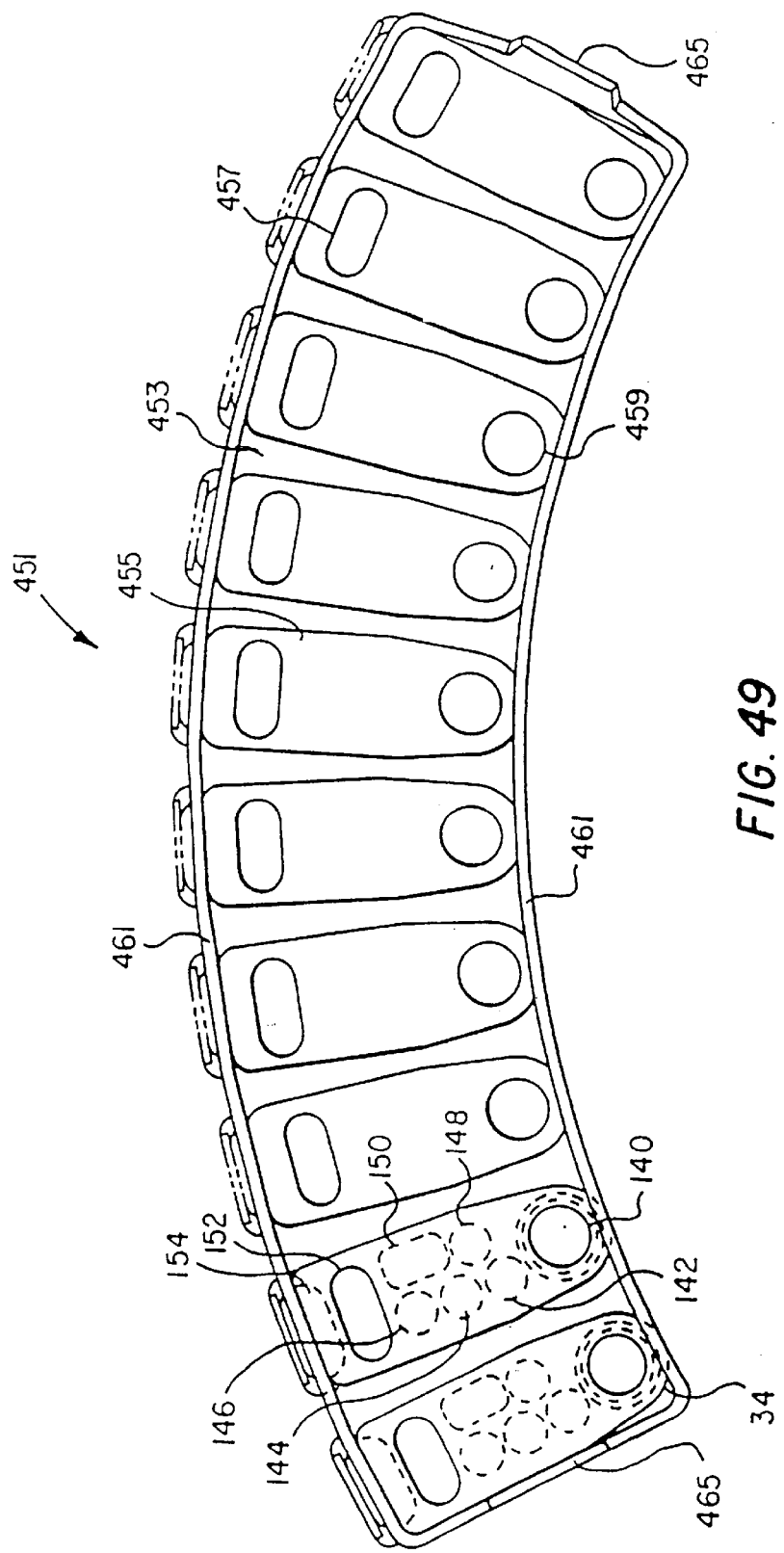
FIG. 49 is a top view of the reaction vessel loading device, the reaction vessel loading device having arced linear dimensions which match the radius of the reaction vessel carousel, the loader having mounted thereon two reaction vessels and the capability of mounting eight additional reaction vessels.

Referring now to FIG. 49, there is shown a top view of the alternate reaction vessel loading device 451 of FIG. 48 having ten (10) recessed planar surfaces 455 for holding ten (10) reaction vessels 34. Although the embodiment illustrated holds ten (10) of the reaction vessels 34, the loading device 451 can be configured to have any number of recessed planar surfaces 455 for holding any number of reaction vessels 34. The recessed planar surfaces 455 are spaced to correspond to the locations for mounting the reaction vessels 34 on the reaction vessel carousel 36 (shown in FIG. 4A). The well plug 457 and the cuvette plug 459 of the loading device 451 insert into, and engage, the well 152 and the cuvette 140 respectively, thereby securing the reaction vessel 34 to the loading device 451. Although the loading device 451 secures the reaction vessels 34 by engaging the well 152 and the cuvette 140, the loading device could secure the reaction vessel 34 by engaging singly, or in combination, any number of the wells 142, 144, 146, 148, 150, 152, and 154 of the cuvette 140.

Referring now to FIGS. 48 and 49 in combination, it can be seen how the loading device 451 is used with the reaction vessels 34. The reaction vessels 34 are loaded onto the loading device 451 by insertion of the well plug 457 and the cuvette plug 459 into the corresponding well 152 and cuvette 140 of the reaction vessel 34. In this manner, the recessed planar surfaces 455 provide a cover for the reaction vessels 34. Also, the well plug 457 and cuvette plug 459 provide a positive seal for the well 152 and the cuvette 140. The loading device 451, with reaction vessels 34 thereon, is positioned on the reaction vessel carousel 36 (shown in FIG. 4A) with the location of the reaction vessels 34 on the loading device 451 corresponding to the locations on the reaction vessel carousel 36 for the reaction vessels 34. An operator is not required to use extraordinary care in shaping the loading device 451 since the loading device 451 is preshaped to fit the dimensions of the reaction vessel carousel 36. In this regard, the reaction vessel loading device is a "drop in " type of loading device for reaction vessels 34. Once the reaction vessels 34 on the loading device 451 are aligned, the reaction vessels 34 are snapped into place on the reaction vessel carousel 36 using the handling fins 465 and elevated rim 461 of the loading device 451. In this manner, a plurality of reaction vessels 34 can be loaded on the reaction vessel carousel 36 at one time saving the operator time over a method of individually loading the reaction vessels 34 into the reaction vessel carousel 36.

Referring still to FIGS. 48 and 49 in combination, once the reaction vessels 34 are loaded into the reaction vessel carousel 36 (shown in FIG. 4A), the loading device 451 can be left in place to provide a cover and a seal for the reaction vessels 34 until used as described above. Removal of the loading device 451 from the reaction vessels 34 is then accomplished by pulling upward on the loading device, utilizing, for example, the handling fins 465 or the elevated rim 461. Removal of the loading device 451 does not dislodge the reaction vessels 34 from the reaction vessel carousel 36 because the holding force of the well plug 457 and cuvette plug 459 to the reaction vessels 34 is less than the force of the reaction vessel carousel 36 holding the reaction vessels 34. This reduced force is due in part to the tapered profile of the well plug 457 and the cuvette plug 458, which also eases the insertion of the reaction vessels 34 onto the loading device 451.

ENVIRONMENTAL CONTROL SYSTEM

Figure 50:
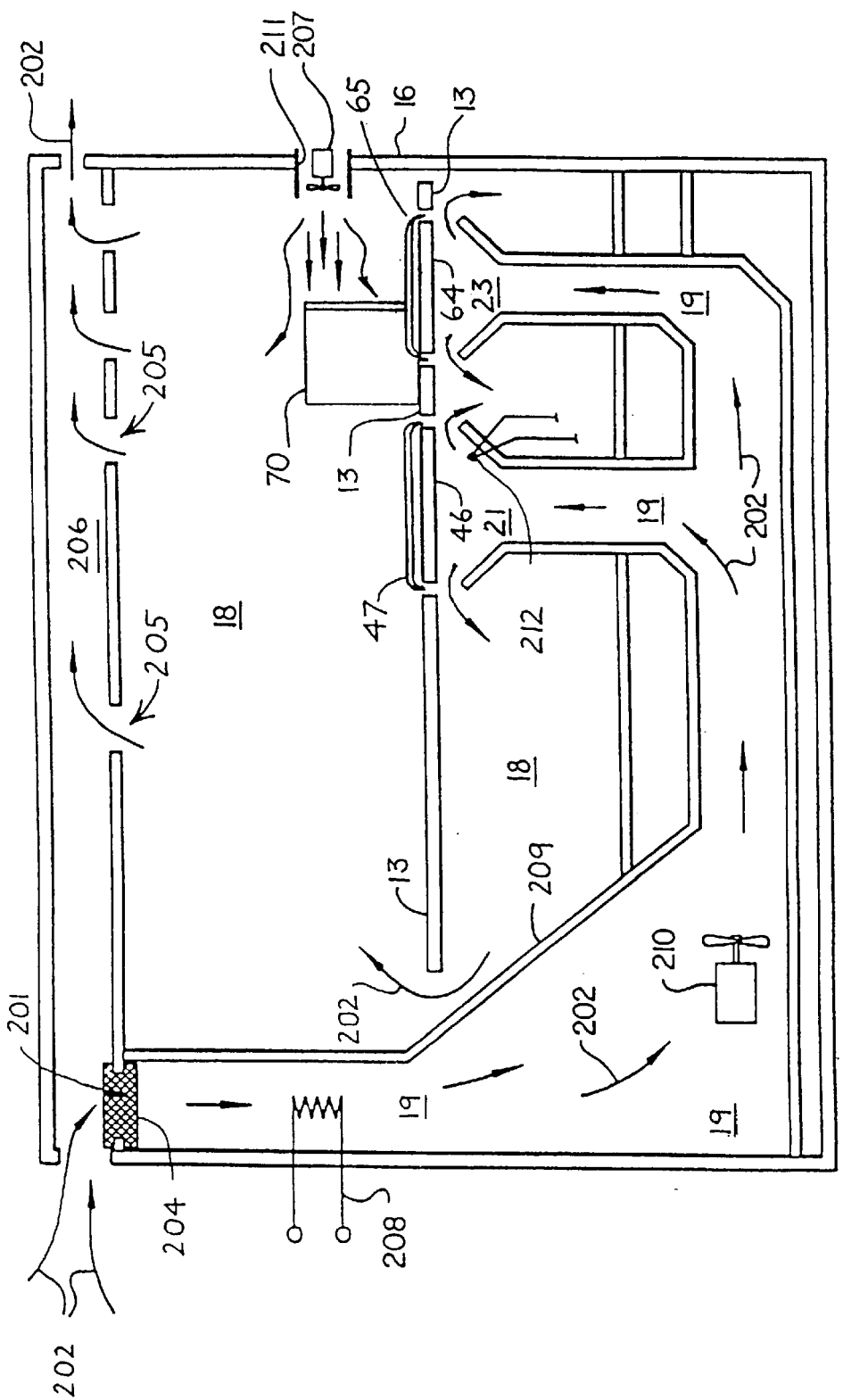
FIG. 50 is a schematic view illustrating the system control environment airflow and temperature control of the automated analytical system.

Referring to FIG. 50, a schematic view illustrating the environmental air flow and temperature control system constructed in accordance with the principles of the present invention is shown. Air flow through the system is indicated by arrows 202 throughout FIG. 50, and is motivated by a fan 210 which draws air through an air inlet 201 and an air filter 204 seated therein through the controlled environment zone 18 and exhausted through a plurality of air outlets 205 and out of the system through an air exhaust conduit 206. The air flow 202 is directed from the inlet 201 through duct means indicated generally at 19 and formed by a baseplate 209 and other walls comprising the body of the analytical system. The duct means 19 forms two pathways enlarging to shroud the process carousel 46 and auxiliary carousel 64 to form carousel environmental zones indicated generally at 21 and 23, respectively, for each carousel. Thus, the carousel environmental zones 21, 23 occupy the space surrounding the lower portion of the carousels 46, 64. The air flow 202 is forced past a heater element 208 positioned in the duct means 19 to direct heated air flow 202 toward the underside of the carousels 46, 64. The temperature in the carousel environmental zone 21 is measured by a sensor 212 electrically connected to a controlled portion of a central processing unit, CPU 255 (FIG. 64), which adjusts electrical power to the heating element 208 to optimize the temperature of the air flow 202 in the carousel environmental zones 21, 23 as required by the system. Temperature control for reaction and incubation in the carousel environmental zones 21, 23 is achieved by controlling the heated air flow 202 into the carousel environmental zones 21, 23. Transfer of heat in the carousel environmental zones 21, 23 can be enhanced by increasing the heated air flow 202 to create turbulent air flow through the carousel environmental zones 21, 23.

The heated air flow 202 flows out of the carousel environmental zones 21, 23 into the controlled environment zone 18 below the platform 13, and then further downstream into a chamber portion of the controlled environment zone 18 above the platform 13. The platform 13 supports heat-generating equipment as shown in FIG. 4A, including, without limitation, the fluid heater and dispenser 70, described in more detail as the heater block assembly 501 as shown in FIG. 52, utilized for temperature control in the fluidic system. While the fan 210 forces the heated air flow into the chamber portion of the controlled environment zone 18, another fan 207 mounted in an inlet 211 to the chamber forces ambient air therein to cool the heat-generating equipment including the fluid heater and dispenser 70. The introduction of ambient air through the inlet 207 is near the exhaust outlets 205 in communication with the controlled environmental zone 18. Although the top portion of the carousels 46, 64 can be exposed to the air flow in the controlled environment zone 18, carousel covers 47, 65 are seated in the platform 13 to prevent contaminants from blowing into the containers supported by the carousels 46 and 64, respectively. The air flow 202 through the duct means 19 is directed into the carousel environmental zones 21, 23 and out into the controlled environment zone 18 away from the space between the top portion of the carousels 46, 64 and the carousel covers 47, 65, respectively.

In operation, the heated air flow 202 provided by the duct means 19 provides a pathway having a substantial pressure drop immediately upstream from the carousel environmental zones 21, 23. The pressure drop in this portion of the duct means 19 is higher than the pressure drop in the carousel environmental zones 21, 23 immediately below the carousels 46, 64, regardless of whether the carousels are fully or partially loaded with containers. Thus, the heated air flow distributes itself evenly around the bottom portion of the carousels 46, 64 rather than flowing through gaps created by empty positions in the carousels 46, 64. Controlling the pressure in this manner minimizes the air flow in the space above the top surface of the carousels 46, 64 and below the carousel covers 47, 65. Reducing the air flow in this space reduces evaporation from the liquid surfaces exposed by the open containers positioned in the carousels 46, 64.

Figure 51:
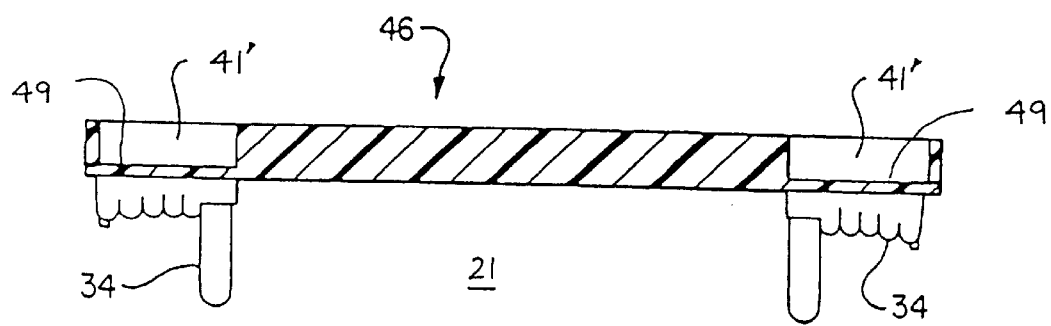
FIG. 51 is an elevational, cross-sectional view of the process carousel as disposed in the controlled environmental zone and holding a plurality of reaction vessels.

Referring now to FIG. 51, a cross-sectional view of the process carousel 46 constructed in accordance with the principles of the present invention is shown as an example, recognizing that the following description also applies to the auxiliary carousel 64. The process carousel 46 contains a plurality of reaction vessels 34 positioned at stations around its circumference. Each reaction vessel 34 is seated in a recessed area opening from the top portion of the process carousel 46 to a bottom plate on which the reaction vessels 34 are seated. The recessed area creates a dead space 46' immediately above the liquid surfaces exposed by the open containers in the reaction vessels 34, which further minimizes adjacent air flow and subsequent evaporation of the liquids contained therein. Thus, even though the lower portion of the reaction vessels 34 which occupy the process carousel environmental zone 21 are subject to air flow, the space above the carousel 46 and the dead space 46' are substantially isolated and do not communicate with the process carousel environmental zone 21 or any other air flow 202 in the controlled environment zone 18. Isolating these spaces from the process carousel environmental zone 21 facilitates heated air flow 202 of the process control environmental zones against the reaction vessels 34 without disturbing the air directly over the liquids contained in the reaction vessels 34, thereby transferring heat to the reaction vessels 34 while minimizing evaporation of the fluids therein.

LIQUID HEATER ASSEMBLY

Referring now to FIGS. 52–54 in combination, there is shown a heater assembly 501 (70 in FIG. 50). The heater assembly 501 generally comprises a heater block or body 502 having therein a coiled tube 521 for passing liquid, a pair of heating elements 505 and 506, a thermistor 508, a thermostatic connection 509, a backup thermostatic connection 511, and a ground pin 519. The heater body 502 is constructed of, for example, a metal such as aluminum, silver, copper, or any other suitable thermal conductive material. The heater body 502 can be constructed by casting around the components therein, or by machining the material of the heater body for insertion of those components. The heater body 502 includes an inlet connection 513 for connecting a liquid source to the coiled tube 521, and an outlet interface 515 for efficiently dispensing liquid from the coiled tube 521 into a container or other means for receiving the liquid, such as the MEIA cartridge 68 (not shown). The heater body 502 also includes mounting means 516 and 518, which are used to secure the heater assembly 501 to the proper location for dispensing the heated liquid.

Still referring to FIGS. 52–54 in combination, the coiled tube 521 is disposed in a generally central location of the heater body 502. The coiled tube 521 has an interior surface that is substantially inert to the liquid flowing therethrough. An inlet 521a of the coiled liquid tube 521 is positioned within the inlet connection 513 of the heater body 502 for receipt of the liquid to be heated. An outlet 521b of the coiled tube 521 is positioned within the outlet interface 515 of the heater body 502 for dispensing the liquid flowing from the outlet 521b of the heater assembly 501. The outlet 521b of the coiled liquid tube 521 extends below a planar surface 515a of the outlet interface 515. In this manner, heated liquid exiting the outlet 521b will not have a planar surface to which the liquid would cling or on which it would accumulate. A protective material 517 such as, for example, a teflon sleeve, can be placed over the exterior surface of the outlet 521b to help prevent liquid from clinging to the outlet 521b and migrating to the planar surface 515a of the outlet interface 515. In this manner, liquid does not accumulate on the outlet interface 515 which becomes contaminated and subsequently contaminates the heated liquid flowing therefrom.

Referring still to FIGS. 52–54 in combination, the pair of heating elements 505 and 505 are located in the heater body 502 on planes (e.g., the plane for heating element 505 cutting through the heater body 502 as shown in FIG. 53) substantially parallel with the coiled tube 521 disposed on a plane therebetween (i.e., the plane cutting through the heater body 502 as shown in FIG. 54). Each of the heating elements 505, 506 have a pair of electrical posts 505a,b and 506a,b respectively, which extend out from the top of the heater body 502 and connect to a source of power. The thermistor 508 is disposed within the heater body 502 so that it is centrally located with respect to the heating elements 505, 506 and the coiled tube 521. Also, the thermistor 508 has electrical terminals 508a and 508b which extend out of the top of the heater body 502. The thermostatic connection 509 is disposed in the heater body 502 near the heating elements 505, 506 and the coiled liquid tube 521, and has electrical terminals 509a and 509b which extend out of the top of the heater body 502. The backup thermostatic connection 511 is also disposed in the heater body 502 near the heating elements 505a–b and the coiled liquid tube 521. Likewise, the backup thermostatic connection 51 also has electrical terminals 511a and 511b which extend out of the top of the heater body 502. The ground pin 519 can be used to electrically ground the heater assembly 501 to other components.

Referring still to FIGS. 52–54, heat is supplied to the heater body 502 by applying an electrical current to the heating elements 505, 506. The amount of heat supplied to the heater body 502 is controlled by the amount of electrical current supplied to the heating elements 505, 506. The thermistor 508 is used to regulate the amount of electrical current supplied to the heating elements 505, 506. The thermistor 508 is an electrical resistor which provides an electrical resistance between the electrical terminals 508a and 508b that varies with the temperature of the heater body 502. As the temperature of the heater body 502 increases, the electrical resistance between the electrical terminals 508a–b also increases. Likewise, as the temperature of the heater body 502 decreases, the resistance between the electrical terminals 508a–b also decreases. In the preferred embodiment, the electrical terminals 508a–b of the thermistor 508 are connected to the power source in series with the heating elements 505, 506 which are electrically connected together in series or parallel. Thus, as the temperature of the heater body 502 decreases, the resistance of the thermistor 508 decreases, thereby increasing the supply of current to the heating elements 505, 506 and the amount of heat supplied to the heater body 502. Likewise, as the temperature of the heater body 502 increases, the resistance of the thermistor 508 increases, thereby decreasing the supply of current to the heating elements 505, 506 and the amount of heat supplied to the heater body 502. In this manner, the temperature of the heater body 502 can be precisely controlled by the thermistor 508. Alternatively, a controller (not shown) could be used to monitor the resistance of the thermistor 508 for heating the heater body 502, and supply electrical current to the heating elements 505, 506 to supply heat to the heater body 502 based on the resistance of the thermistor 508.

Referring still to FIGS. 52–54 in combination, under normal conditions the thermostatic connection 509 and the backup thermostatic connection 511 provide an uninterrupted electrical path between the electrical terminals 509a–b and 511a–b, respectively. However, when the heater body 502 extends a safe operating temperature, the thermostatic connection 509 and the backup thermostatic connection 511 provide an open circuit between the electrical terminals 509a–b and 511a–b, respectively. In the preferred embodiment of the heater assembly 501, the thermostatic connection 509 and the backup thermostatic connection 511 are electrically connected in a series arrangement between the power supply and the heating elements 505, 506, which can be electrically connected together in series or parallel. Thus, if either the thermostatic connection 509 or the backup thermostatic connection 511 sense that the temperature of the heater body 502 is above a predetermined overheat temperature, the thermostatic connection 509 or the backup thermostatic connection 511 sensing the unsafe temperature will open the circuit between the power supply and the heating elements 505, 506, thereby stopping the flow of heat into the heater body 502. In this manner, an overheated condition of the heater assembly 501 can be avoided.

Referring still to FIGS. 52–54 in combination, liquid flows into the heater assembly 501 through the inlet end 521a of the coiled tube 521. As the liquid progresses through the coiled tube 521, heat is transferred to and from the liquid by the heater body 502. By the time that the liquid reaches the outlet and 521b of the coiled tube 521, the liquid is substantially the same temperature of the heater body 502, as described above, the temperature of the liquid leaving the outlet and 521b of the coiled tube 521 can be controlled to within at least ±1.0° C. of the required liquid temperature, and preferably to within ±0.5° C. of the required liquid temperature. Positioning of the receiving means in relationship to the outlet interface 515 of the heater assembly 501, is such that the air gap between the outlet end 521b of the coiled liquid tube 521 and the point of deposition on the receiving means is one-half (½) inch or less, thereby depositing the liquid with little or no temperature change. The loss of temperature by the liquid as it passes from the outlet end 521b and the receiving means can be further reduced by reducing the air gap between the outlet end 521b and the receiving means to three-eighths (⅜) inch or less.

MEIA CARTRIDGE FEEDER AND CARTON

Figure 55:
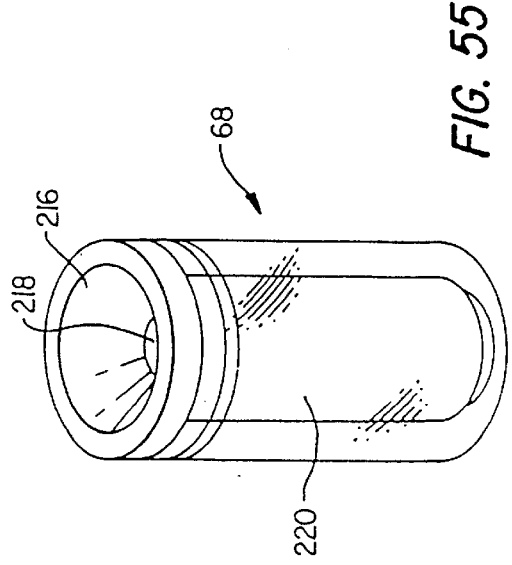
FIG. 55 is a side elevational view in partial section of a MEIA cartridge for use with the automated analytical system.

Referring now to FIG. 55, there is shown in MEIA cartridge 68 constructed in accordance with the principles of the present invention. The MEIA cartridge is generally cylindrical in shape containing a support matrix material 222. The top of the MEIA cartridge 68 forms a funnel throat 216 tapering downwardly to an opening 218 in the MEIA cartridge 68. The opening 218 provides access to the support matrix material 222 contained therein. The bottom of the MEIA cartridge 68 is substantially flat.

Referring now to FIG. 56, there is shown a cartridge feeder apparatus indicated generally at 500 which feeds MEIA cartridges 68 from a cartridge hopper 590 singly, upright, and on-demand to a trap door assembly indicated generally at 700. The cartridge hopper 590 holds a plurality of MEIA cartridges 68 positioned horizontally and gravity-fed into the cartridge hopper 590 without regard to the orientation of the top and bottom of the MEIA cartridge 68 which can be facing either direction. The cartridge hopper 590 is removably attached to a bridge 510 that is a stationary portion of the cartridge feeder apparatus 500. The bridge 510 has a bridge throat 514 for receiving MEIA cartridges 68 from the hopper 590 in single-file and providing a passage through the cartridge feeder apparatus 500. The bridge 510 also supports a pair of guide rods 512 (only one of the guide rod 512 has been shown for clarity), upon which a shuttle 520 is slidably mounted to move along a shuttle path in a horizontal direction perpendicular to the longitudinal axis of the MEIA cartridges 68 in the throat 514 of the bridge 510.

Referring still to FIG. 56, a linear motor 530 moves the shuttle 520 bidirectionally along the shuttle path on the guide rods 512 of the bridge 510. The shuttle 520 has a shuttle throat 522 for receiving MEIA cartridges 68 from the bridge throat 514 when the shuttle 520 is aligned therewith in a home position. The linear motor 530 then slides the shuttle 520 along the shuttle path to a drop position when aligned with a chute 560. As the linear motor 530 slides the shuttle 520 from the home position toward 530 slides the shuttle 520 from the home position toward the drop position, cup pins 550a–b grasp the MEIA cartridge 68. When the shuttle 520 reaches the drop position, the cup pins 550a–b release the MEIA cartridge 68 such that the bottom of the MEIA cartridge 68 drops first causing it to fall into the chute 560 in an upright position.

Still referring to FIG. 56, the chute 560 has a tapered inner profile which assists in orienting the MEIA cartridge 68 in the upright position as the MEIA cartridge 68 drops into the trap door assembly 700. The chute 560 is rotatably mounted to the cartridge feeder apparatus 500. A spring 562 holds the chute 560 in position during normal operation of the cartridge feeder apparatus 500. A dump lever 564 connected to the chute 560 rotates the chute 560 against the force of the spring 562 when actuated. In this manner, any MEIA cartridge 68 which lodges in the chute 560 can be cleared by pressing the dump lever 564, which rotates the chute 560 and dumps the MEIA cartridge 68. After the MEIA cartridge 68 has been dumped, the dump lever 564 is released and the spring 562 returns the chute 560 to its normal operational position.

Referring still to FIG. 56, pushers 540a and 540b are mounted on top of the shuttle 520 to engage the MEIA cartridges 68 through openings in side walls of the cartridge hopper 590. The pushers 540a–b pass through the openings in the cartridge hopper 590 and contact the MEIA cartridges 68 to move them and prevent them from blocking the passage to the bridge throat 514 of the cartridge feeder apparatus 500. When the shuttle is in the home position, the pusher 540a passes through one opening in the side wall of the hopper 590 and aligns the MEIA cartridges 68 above the bridge throat 514. When the shuttle 520 is in the drop position, the pusher 540b passes through the other opening in the opposing side wall of the cartridge hopper 590 and also aligns the MEIA cartridges 68 for passage through the bridge throat 514.

Figure 57:
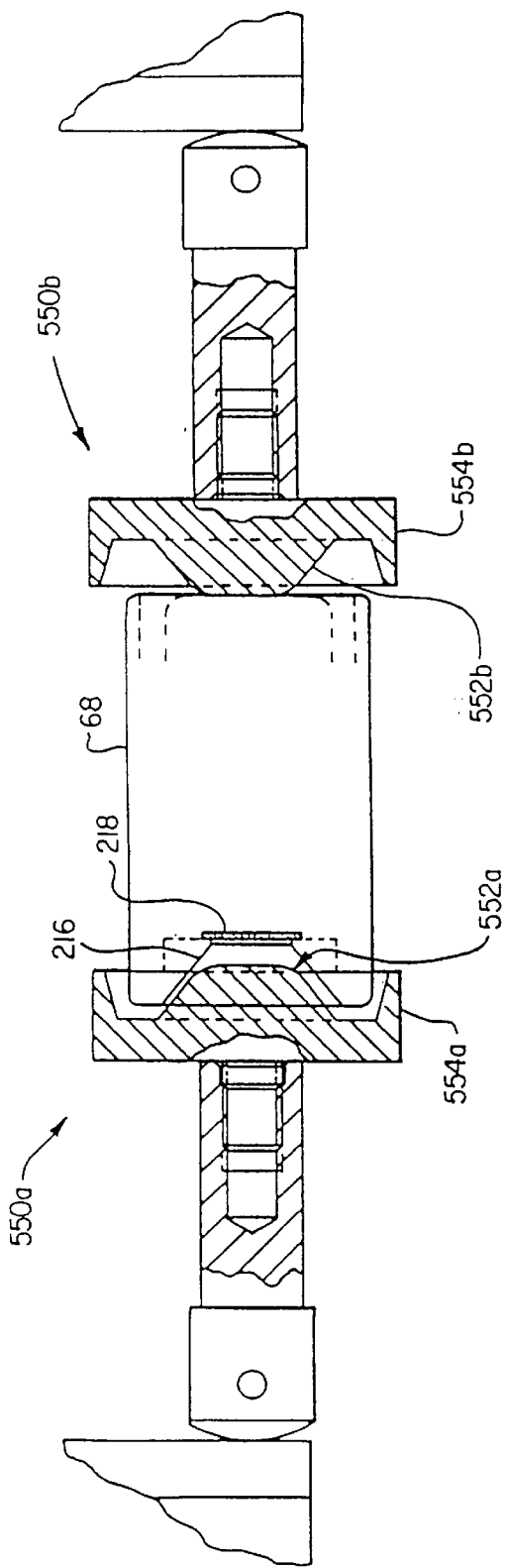
FIG. 57 is a side sectional view in isolation of the MEIA cartridge feeder-cartridge orientation pin mechanism of the cartridge feeder of FIG. 56.

Referring now to FIG. 57, the cup pins 550a–b have opposing center profiles 552a and 552b, each one having a contour matching the shape of the funnel throat 216 of the MEIA cartridge 68. The middle of the center profiles 552a–b are truncated so that they do not extend through the funnel throat 216 into contact with the cartridge opening 218 or the support matrix material 222 of the cartridge 68. The cup pins 550a–b also have an outer lip 554a–b concentric with the center profile 552a–b and having an inner diameter sufficiently large for receiving the top of the MEIA cartridge 68 to fit within the outer lip 554a–b surrounding the center profile 552a–b. Also, the outer lip 554a–b does not extend beyond the truncated middle of the center profile 552a–b.

Referring now to FIGS. 56 and 57 in combination, it can be seen how the cartridge feeder apparatus 500 feeds MEIA cartridges 68 singly in an upright position to a trap door assembly 700. As previously described, the MEIA cartridges 68 pass from the bridge throat 514 to the shuttle throat 522 when the shuttle 520 is in the home position. As the shuttle moves from the home position, the cup pins 550a–b close on the MEIA cartridge 68. When the cup pins 550a–b will be facing the funnel throat 216 and will fit therein to engage the top of the MEIA cartridge 68. Referring more specifically to FIG. 57, the cup pin 550a faces the funnel throat 216 to engage the top of the MEIA cartridge 68. In this position, the center profile 552a fits within the funnel throat 216 and the outer lip 554a surrounds the outside top of the MEIA cartridge 68. The flat bottom of the MEIA cartridge 68 has no recess for receiving the center profile 552b of the cup pin 550b. Consequently, the outer lip 554b will not surround and support the bottom of the MEIA cartridge 68.

Referring still to FIGS. 56 and 57 in combination, as the shuttle 520 approaches the drop position, the cup pins 550a–b begin to separate to drop the MEIA cartridge 68 into the chute 560. When the cup pins 550a–b begin to separate, gravity pulls the bottom of the MEIA cartridge 68 downward. The bottom drops first because the middle of the center profile 552b is flush with the bottom of the MEIA cartridge 68 which, consequently, is not supported by the outer lip 554b. As the cup pins 550a–b continue to separate, the center profile 552a and outer lip 554a of the cup pin 550a engaging the top of the cartridge 68 continue to engage the top of the MEIA cartridge 68 while the bottom of the MEIA cartridge 68 is dropping into the chute 560 due to gravitational forces. Once the cup pins 550a–b have separated a sufficient distance, the funnel throat 216 of the cartridge 68 will disengage from the center profile 552a, and the outer lip 554a of the cup pin 550a engaging the top portion of the cartridge 68 will disengage, allowing the MEIA cartridge 68 to fall in an upright position through the chute 560. It can be seen from FIG. 18, that the design of the cup pins 550a–b will drop the cartridge 68 in an upright position regardless of the orientation of the MEIA cartridge 68 between the cup pins 550a–b. Thus, MEIA cartridges 68 are dispensed on demand, singly, and in an upright position, from the hopper 590 through the cartridge feeder apparatus 500 into a trap door assembly 700.

Referring back to FIG. 56, the trap door assembly 700 comprises a trap door body 710 with a cartridge passage 712, a semicircular door 720 which rotates on an axis indicated by line X—X, and a cartridge height adjustor 722 mounted on the bottom of the semicircular door 720. The cartridge height adjustor 722 is a flange extending downwardly from the semicircular door 720 so that the bottom 723 of the flange is at a predetermined distance corresponding to a focal distance for optical equipment positioned adjacent the auxiliary carousel 64 (not shown, see FIG. 4A) at a subsequent testing station. The flange of the cartridge height adjustor 722 has a leading edge 724 forming an obtuse angle with the bottom of the semiconductor door 720. When the MEIA cartridge 68 falls into the cartridge passage 712, the semicircular door 720 has rotated to a position blocking the cartridge passage 712 to catch the MEIA cartridge 68. When the auxiliary carousel 64 (not shown) under the trap door assembly 700 is positioned to receive the MEIA cartridge 68, the semicircular door 720 rotates to a position that opens the cartridge passage 712 allowing the MEIA cartridge 68 to fall through into a chamber of the e auxiliary carousel 64. After the MEIA cartridge 68 passes through the cartridge passage 712, the semicircular door 720 continues to rotate moving the leading edge 714 of the cartridge height adjustor 722 against the top of the MEIA cartridge 68, thereby forcing it down into the spring-loaded chamber of the auxiliary carousel 64 to the predetermined focal distance. Thus, when the MEIA cartridge 68 is rotated by the auxiliary carousel 64 to the test station, it is always seated at a height which is a fixed focal distance from the optics at the test station regardless of its position in the chamber of the auxiliary carousel 64 which can vary as a result of variations in distance between the top of the auxiliary carousel 64 and the optical equipment at the test station.

Figure 58:
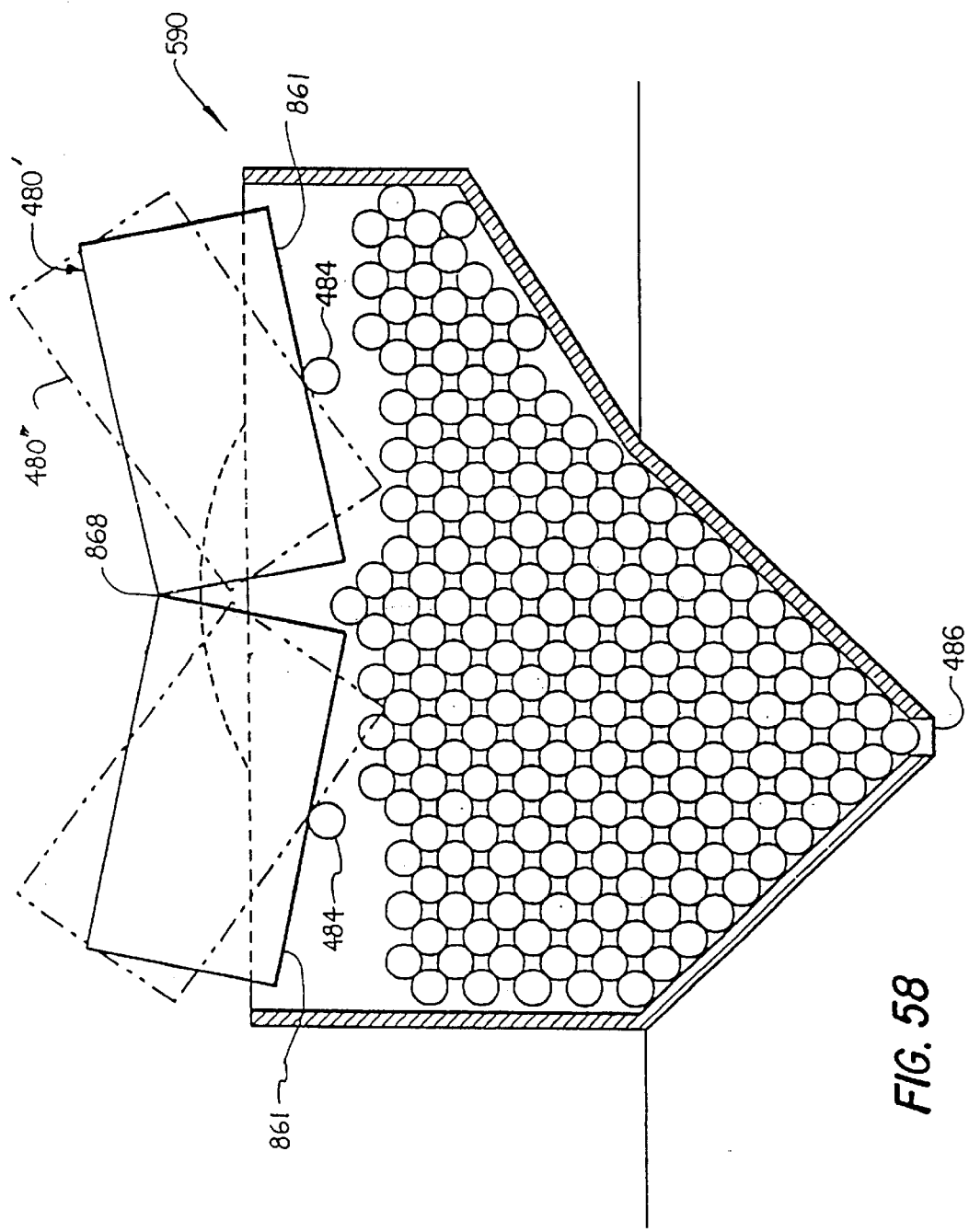
FIG. 58 is a side cross-sectional view in isolation of a split open cartridge carton shown in various open positions in phantom as engaged in cooperation with a cartridge hopper containing multiple cartridges.

Referring now to FIG. 58, there is shown a side cross-sectional view of a cartridge hopper 590 with a cartridge carton 480 positioned therein and partially open as indicated by 480' for unloading cartridges 68 into the hopper 590. The lower portion of the cartridge hopper 590 is tapered to a hopper release opening 486. The upper portion of the cartridge hopper 590 is large enough to act as a reservoir for all of the cartridges 68 in the cartridge carton 480. The cartridge carton 480 also has two roller pins 484 positioned between the sidewalls therein for supporting the cartridge carton 480. The cartridge carton 480 is also shown in phantom fully opened at a maximum unloading position 480", both ends of the carton 480 having been guided by the roller pins 484.

Figure 59A:
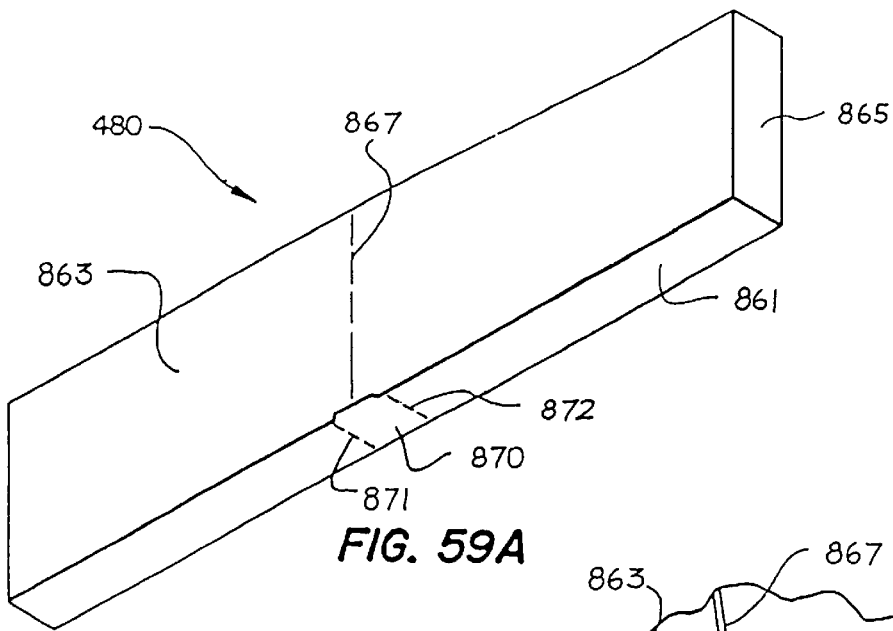
FIG. 59A is an isometric view of the cartridge carton, taken form the lower side of the cartridge carton.
Figure 59B:
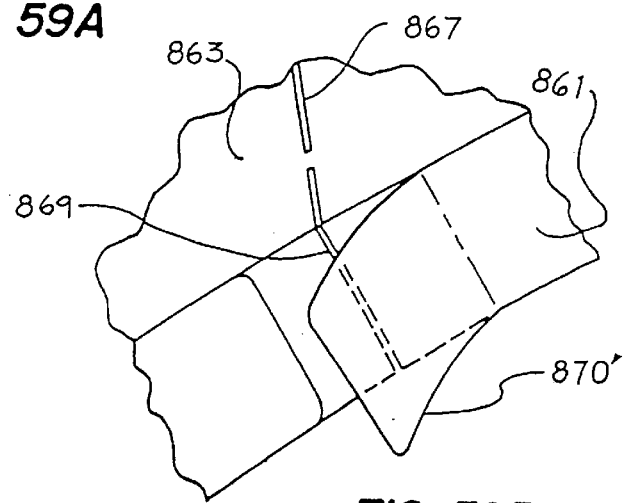
FIG. 59B is a partial, isometric view of the cartridge carton, illustrating the operation of the tab opening.
Figure 60:
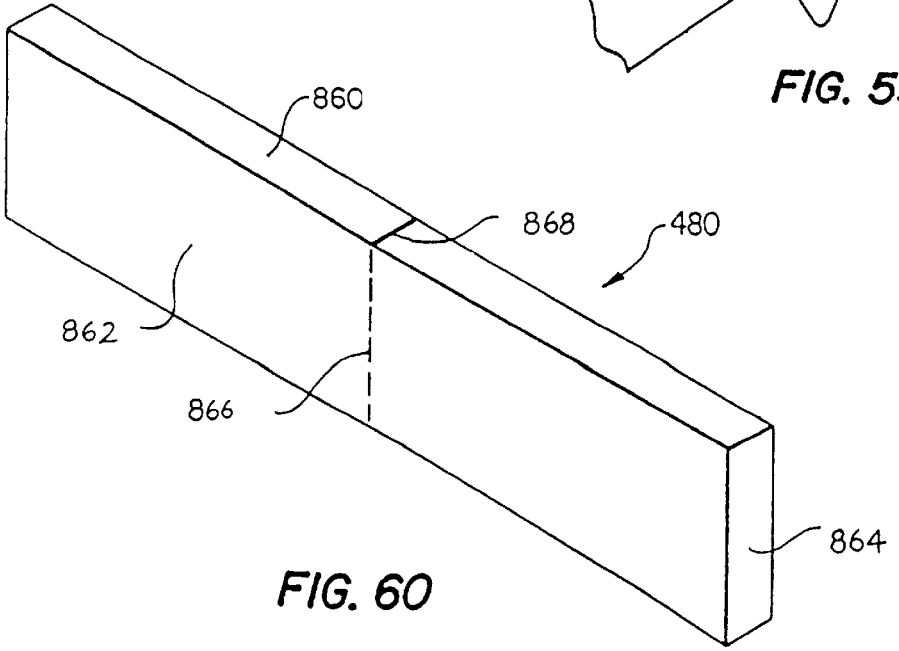
FIG. 60 is an isometric view of the cartridge carton, taken from the upper side of the cartridge carton.

Referring now to FIGS. 59A, 59B, and 60 in combination, there is shown the cartridge carton 480 from FIG. 58. The cartridge carton 480 comprises a top 860 and bottom 861, and parallel facing sidewalls 862 and 863 each joined to the top 860 and bottom 861 of the cartridge carton 480. The parallel facing sidewalls 862, 863 are separated by a distance at least as long as the height of the MEIA cartridges 68. However, it is preferable that the distance separating the parallel facing sidewalls 862, 863, not be too large to allow the MEIA cartridge 68 to rotate within the cartridge carton 480. The cartridge carton 480 is closed by end walls 864 and 865, each joined to the top 860 and bottom 861 of the cartridge carton 480, as well as the sidewalls 862, 863. The sidewalls 862, 863 each have a perforation line 866 and 867, respectively, between the top 860 and bottom 861 of the cartridge carton 480 dividing them in half. The top 860 of the cartridge carton 480 is creased to form a hinge 868 between the ends of the perforation lines 866, 867 in the sidewalls 862, 863. The bottom 861 of the cartridge carton 480 also has a perforation line 869 between the other ends of the perforation lines 866, 867 in the sidewalls 862, 863. The cartridge carton 480 also comprises a tab 870 covering the perforation line 869 in the bottom 861 and fastened on both sides of the perforation 869. The tab 870 can be torn away from the bottom 861 along perforation line 871 and 872 where fastened, as shown in FIG. 59A, or at only one end where fastened as shown at 870' in FIG. 59B. It is to be understood that the invention is not limited to the details of construction of the tab 870. The cartridge carton 480 contains a plurality of cartridges 68; however, a carton capacity of about one hundred cartridges 68 is suitable for operation of the cartridge hopper 590 with the roller pins 484 locations. The cartridges 68 are loaded in the cartridge carton 480 in a lateral orientation, end to end between the sidewalls 862, 863, regardless of which direction the cartridge opening 218 is facing.

In operation and also referring to FIG. 58, it can be seen how the cartridges 68 in the cartridge carton 480 are loaded into the cartridge hopper 590. To load the cartridge hopper 590, the tab opening 482 is torn from the bottom 861 of the cartridge carton 480. The cartridge carton 480 is then positioned on the roller pins 484 with the hinge 868 facing upward. A slight downward force applied to the hinge 868 causes the cartridge carton 480 to separate at the perforations 866, 867, 869 opening the cartridge carton 480 through the position indicated generally at 480' to the maximum open position 480" as shown in FIG. 58. When the cartridge carton 480 opens, the cartridges 68 fall into the cartridge hopper 590 in the correct horizontal position. Even though the cartridges 68 are deposited therein with the cartridge openings 218 facing different directions, they do not have to be realigned because the cartridge feeder assembly 500 drops the cartridge 68 in an upright position regardless of their orientation as described above.

Figure 61:
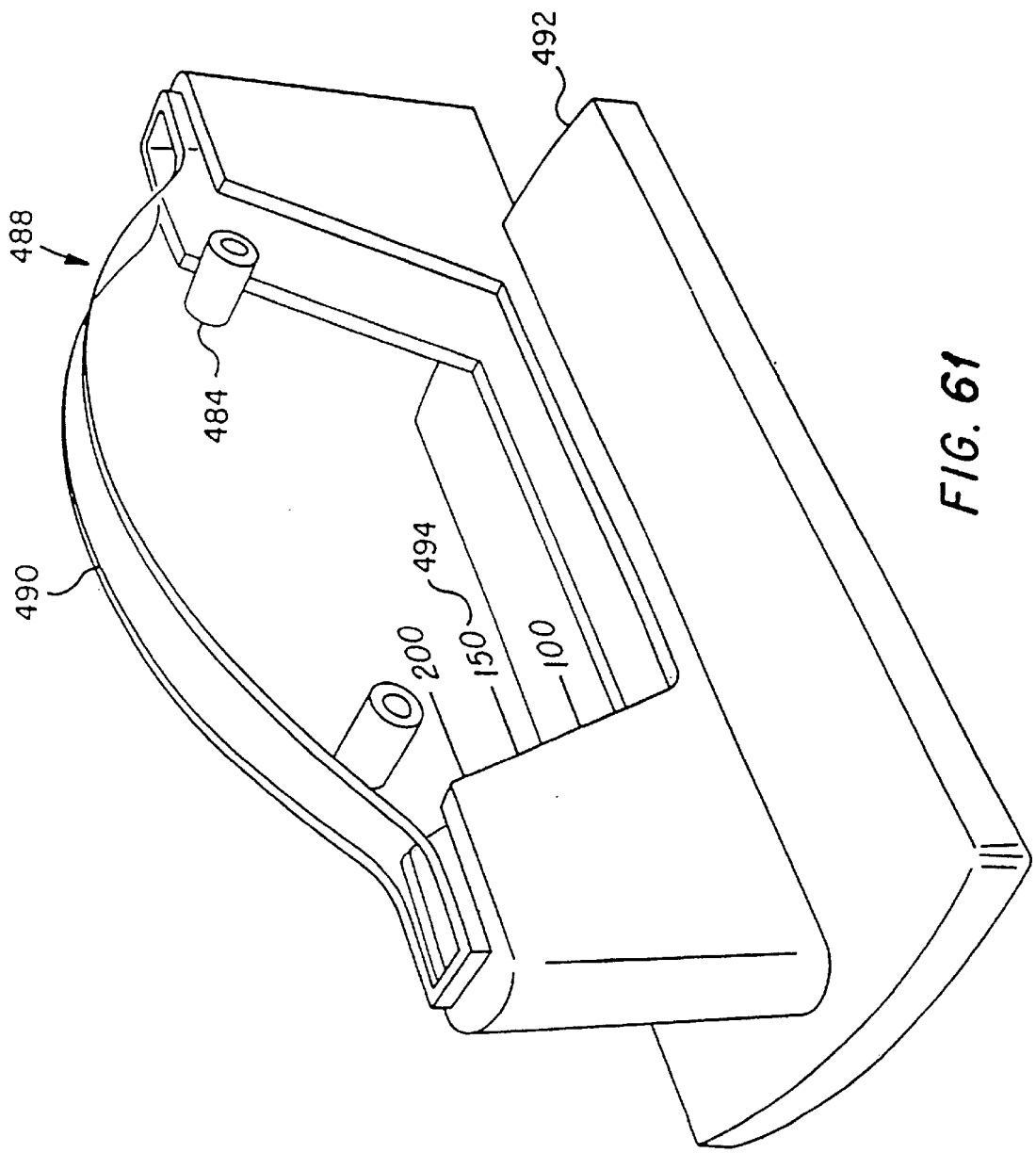
FIG. 61 is an isometric view of another embodiment of a free standing cartridge hopper showing the cartridge hopper in a detached mode suitable for loading cartridges from a cartridge carton.

Referring now to FIG. 61, there is shown an isometric view of an alternate embodiment of a stand alone hopper 488 which is detachable from the remainder of the feed means, the stand alone hopper 488 being easily detached for loading purposes. The hopper presents cartridge availability indication 494 through a transparent wall portion for operator inspection. The stand alone hopper has an attached stand alone base or platform 492 for supporting the hopper during loading of multiple cartridges from a cartridge carton 480 as shown in FIGS. 59A, 59B, and 60, utilizing the roller pins 484.

OPTICS CONTROL SYSTEM

Figure 62:
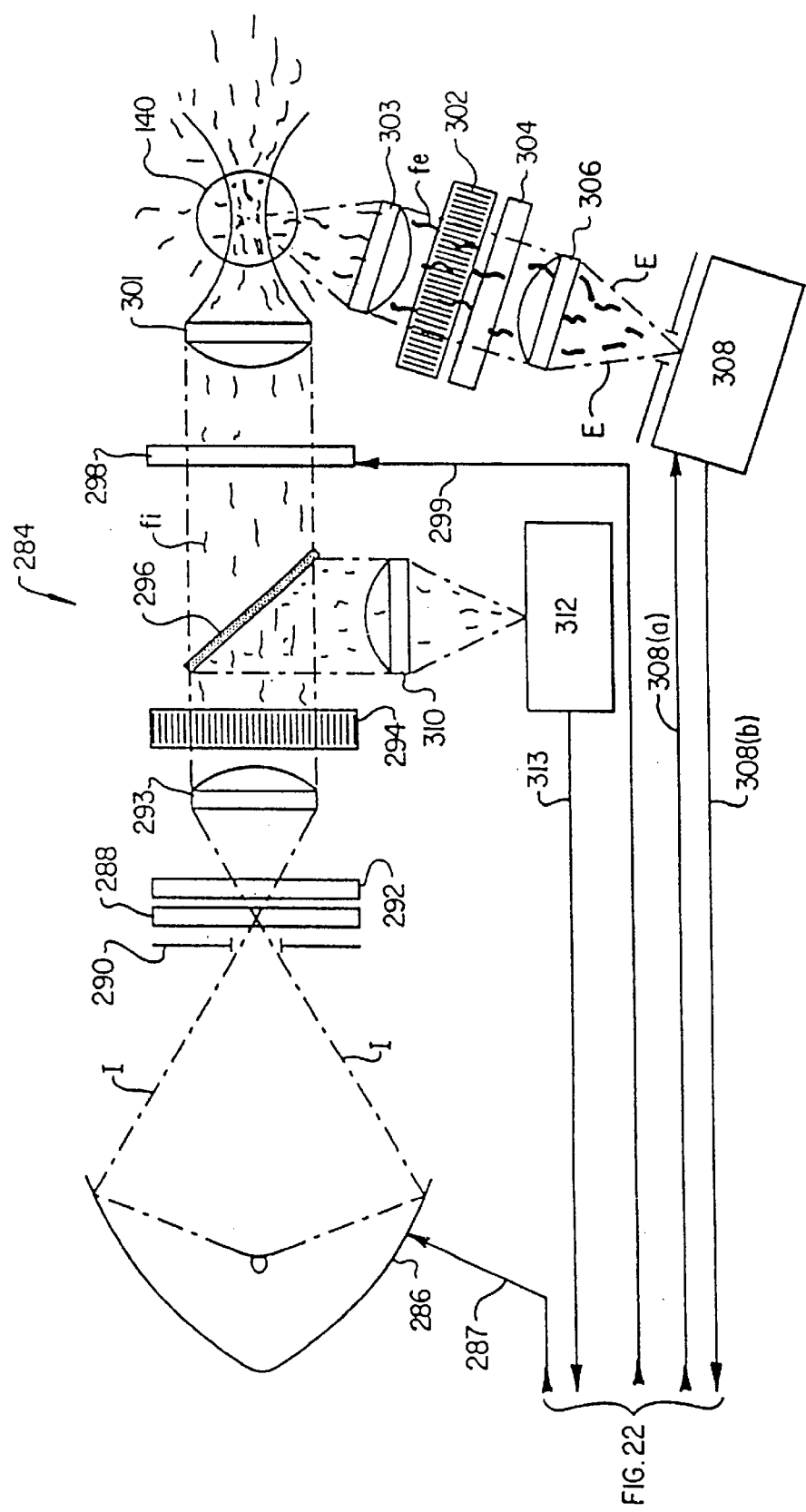
FIG. 62 is a schematic of the FPIA optics system of the automated analytical system.
Figure 63:
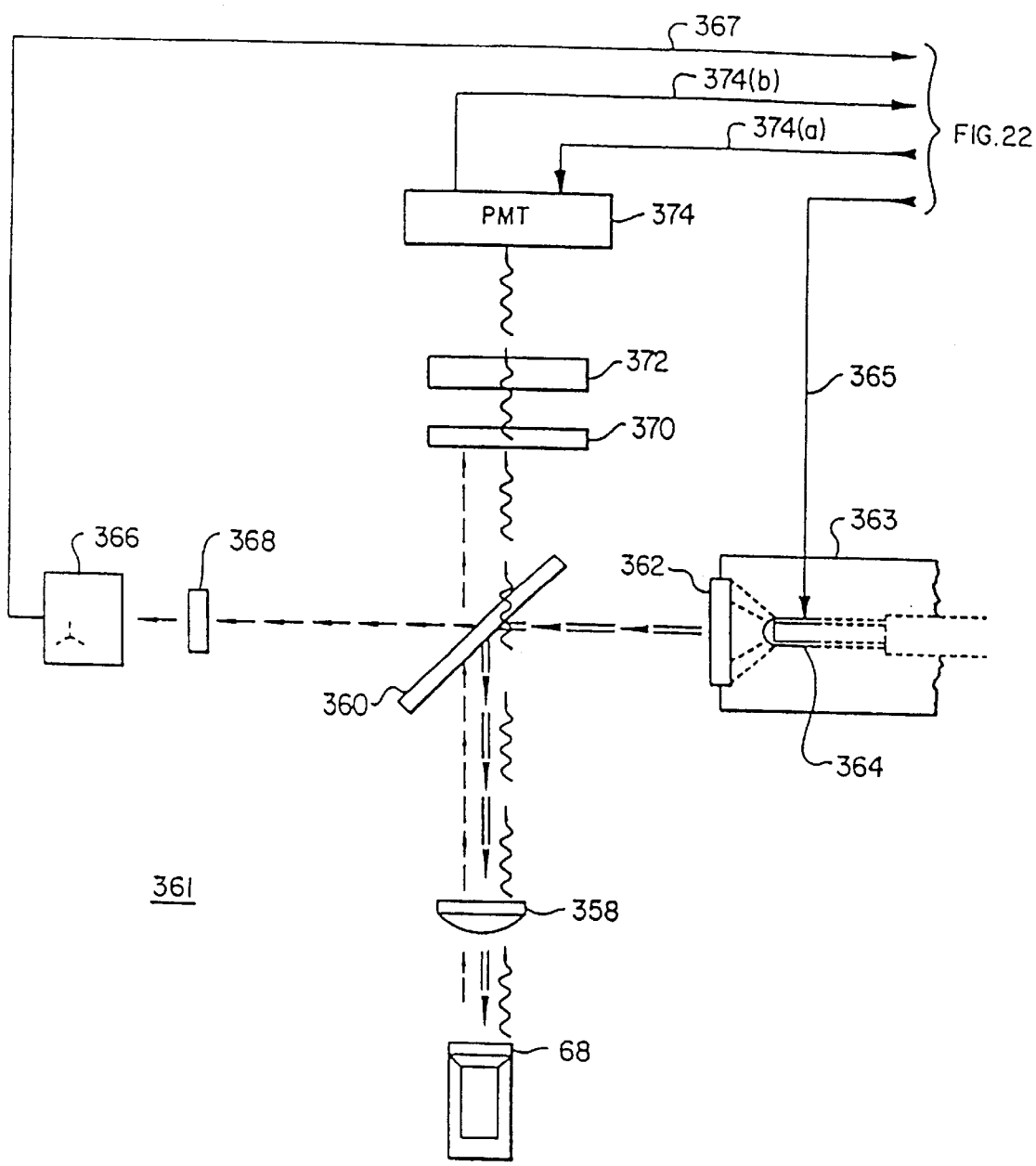
FIG. 63 is a schematic of the MEIA optics system of the automated analytical system.
Figure 64:
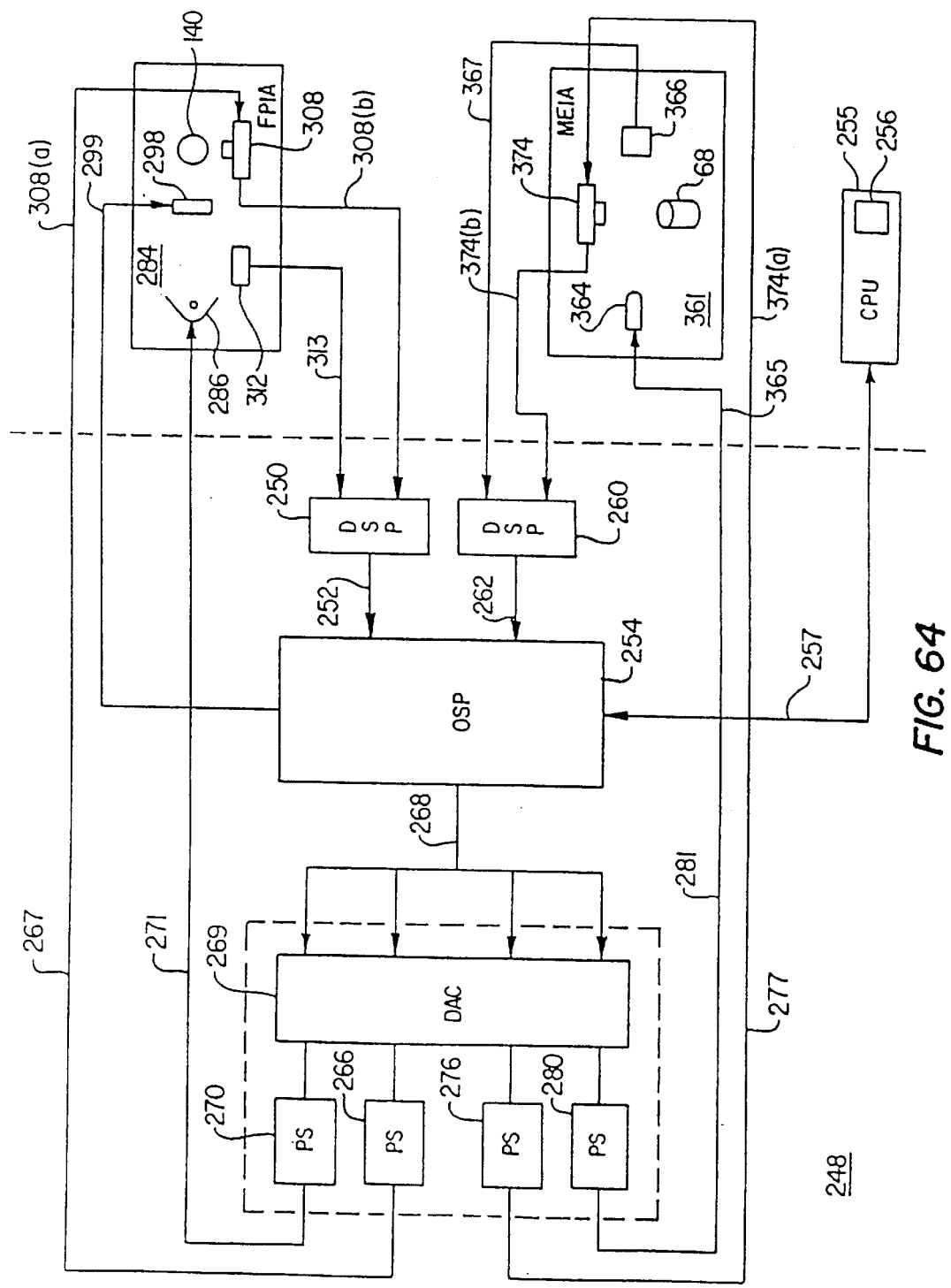
FIG. 64 is a box diagram of the optics control system of the automated analytical system.

The present invention includes an optics control system shown generally at 248 in FIG. 64 which simultaneously and continuously manages in real time an optical system for the FPIA shown generally at 284 in FIG. 62 (the "FPIA optics system") and an optical system for the MEIA shown generally at 361 in FIG. 63 (the "MEIA optics system"), both of which contain optics used in Abbott's IMx® and TDx®analyzers which are well known in the art. The heart of the optics control system 248 is an optical signal processor 254 ("OSP") which is dedicated to the optics systems 284, 361 and communicates with the central processor 255 over a bidirectional bus 257. The scheduler 256 running on the central processor 255 sends macro-commands to the OSP 254 which interprets them and generates micro-commands for controlling the FPIA optics system 284 and the MEIA optics system 361. Although the scheduler 256 has a prior knowledge of what both optics systems 284, 361 will read because of its knowledge of the reagents, the OSP 254 collects data from both and transmits it back to the central processor 255 which continues operating the random access analytical system in real time. The OSP 254 has no such prior knowledge, but is essential for controlling, collecting and transmitting the large volume of data in real time.

To better understand how the optics control system 248 manages the FPIA and MEIA optics system 284 and 361, both are defined more specifically as follows. Referring to FIG. 62, the light source for the FPIA optics system 284 is a tungsten halogen lamp 286 which provides a source of light energy for illuminating the FPIA reaction mixture in the cuvette 140 along an incident path I. The lamp 286 focuses the light through an aperture 290, a heat reflector 288, and heat absorber 292 to a plano convex lens 293 which collimates the light through an excitation filter 294 at a frequency of 485 nm represented by the fine short lines $f_i$, i.e., the incident frequency. The collimated beam of light is split by a beamsplitter 296, the reflected portion being focused by a plano convex lens 310 to a reference detector 312, a photodiode, and the transmitted portion propagating through a transmissive liquid crystal 298 and focused by another plano concave lens 301 through the FPIA reaction mixture in the cuvette 140 which fluoresces at a higher frequency of 535 nm represented by the darker short lines, $f_e$, i.e., the emitted frequency. A plano convex lens 306 collimates the light emitted from the fluorescing mixture along an emitted path E through an emission filter 302 and a polarized 304 to another plano convex lens 306 which focuses the emitted light on a photo multiplier tube ("PMT") 308. Power is supplied to the lamp 286 and the PMT 308 via inputs 287 and 208 (a), respectively, and control signals are sent to the liquid crystal 298 via an output 299 which controls the state of the liquid crystal 298 via an output 299 which controls the state of the liquid crystal 298 to be either vertically or horizontally polarized. The reference detector 312 provides an output 313 to the optical control system 248 which controls the input 287 to the lamp 286. The PMT 308 also provides an output 308(b) to the optical control system 248 which transmits data from the PMT 308 to the central processor 255.

Referring to FIG. 63, the light source for the MEIA optics system 361 is a mercury vapor lamp 364 which provides a source of light energy for illuminating the contents of the MEIA cartridge 68 along an incident path shown by the double-lined arrows. The light from the lamp 364 illuminates an excitation filter 362 which transmits the light at a frequency of 365 nm. Most of that light is reflected by a chromatic beamsplitter 360 and transmitted through a plano convex lens 358 that focuses the light into the open end of the MEIA cartridge 68. The remainder of the excitation light is transmitted through the chromatic beamsplitter 360 and illuminates an optical bandpass filter 368 which transmits 365 nm to a reference detector 366, a photodiode, which provides an output 367 to the optical control system 248.

As a result of being exposed to excitation light energy, the contents of the MEIA cartridge 68 fluoresce at emission wavelengths which include 450 nm, represented by the S-shaped arrows. The emission light is collected by a lens 358 and, because of the longer wavelength than the excitation, transmits through the chromatic beamsplitter 360. The emission proceeds through emission filters 370 and 372, which transmit light at 450 nm, and finally illuminates a PMT 374. Power is supplied to the lamp 364 and the PMT 374 via inputs 365 and 374(a), respectively, and the PMT 374 correspondingly provides an output 374(b) to the optics control system 248 which transmits data from the PMT 374 to the central processor 255.

Another feature of the present invention is the heater block 363 which maintains the temperature of the lamp 364 at a minimum temperature of about 70° C. during periods of nonuse. This temperature must be high enough to ensure that the mercury in the lamp 364 remains in a vapor state to facilitate full brightness within about one second without adversely affecting the life of the lamp 364. The normal time period for changing from cold to full brightness is twenty (20) seconds. This one-second cycle time for the lamp 364 is necessary for high-speed operation in a continuous and random-access analytical system, which will be described in more detail below.

The FPIA and MEIA optics system 284, 361 and the optics control system 248 are shown in FIG. 64 separated by a dashed line. The output 308(b) from the PMT 308 and the output 313 from the reference detector 312 are analog inputs to a digital signal processor A/D chip 250 ("DSP") which can be, for example, an HC11 sold by Motorola. A digital output from the OSP 254 is provided to a digital to analog converter ("DAC") 269 via a serial output bus 268. Separate converter molecules on DAC 269 are connected to separate power supplies 266 and 270 which drive the PMT 308 and the lamp 286, respectively, via outputs 267 and 271, respectively. The OSP 254 cycles the lamp 286 according to macro-commands received from the scheduler 256 and, when turning the lamp 286 on, increases its intensity to provide sufficient illumination for the contents of the cuvette 140 based on data stored in the scheduler 256 and feedback from the reference detector 312. Typically, the illumination is set at about 200 microwatts at a frequency of 485 nm as shown in FIG. 20. The data in the scheduler 256 is part of a table which prescribes the required sample illumination based on the reagents know to be used in that particular FPIA reaction mixture. The OSP 254 simultaneously adjusts the output gain of the PMT 308 in response to commands from the scheduler 256 based on the assay being conducted. The OSP 284 also controls the liquid crystal 298 via the output 299 by creating and removing an E-field to switch between vertical and horizontal polarization based on commands from the scheduler 256. As indicated above and throughout this paragraph, all of the knowledge regarding the assays and the reagents are resident in the scheduler 256 which relies on the OSP 254 for real-time execution in response to the macro-commands.

The same is true when applied to the MEIA optics system 361. The output 374(b) from the PMT 374 and output 367 from the reference detector 366 are analog inputs to another DSP 260 which converts the analog signals to digital signals for transmission to the OSP 254 via another input bus 262. The OSP 254 provides a digital output to separate converter modules on the DAC 269 via the serial output bus 268. These converter modules on the DAC 269 are connected to separate power supplies 276 and 280 which drive the PMT 374 and the lamp 364, respectively, via outputs 374(a) and 365, respectively. The OSP 254 cycles the lamp 364 according to micro-commands received the scheduler 256 and, when turning the lamp 364 on, increases its intensity to provide sufficient illumination for the contents for the MEIA cartridge 68 based on data stored in the scheduler 256 and feedback from the photo diode 366. Again, the data in the scheduler 256 is part of a table which prescribes the required sample illumination based on the reagents known to be used in that particular MEIA reaction mixture. The OSP 254 simultaneously adjusts the output gain of the PMT 374 in response to commands from the scheduler 256 based on the assay being conducted.

Figure 65:
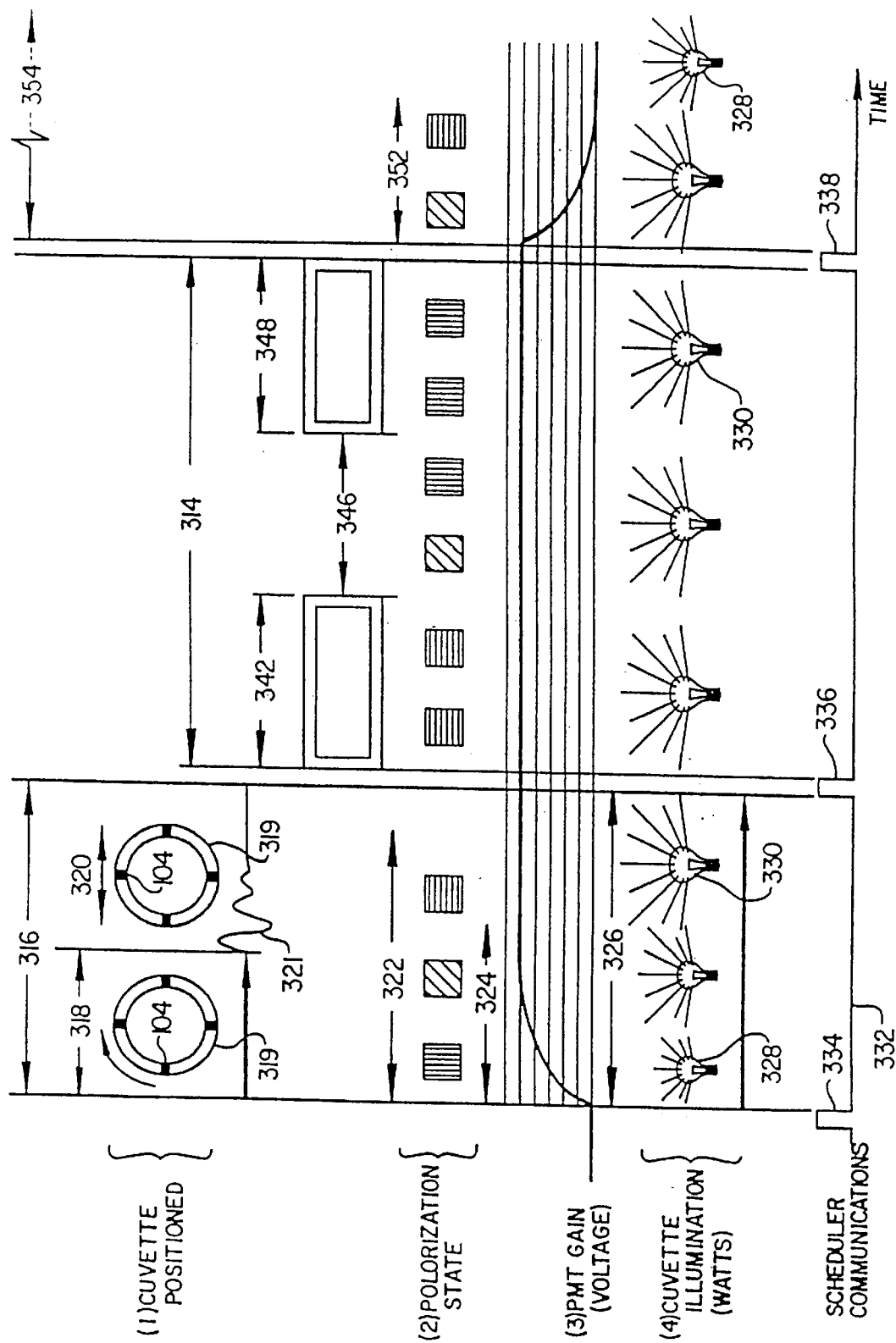
FIG. 65 is a pictorial time graph of the FPIA reader sequence of the automated analytical system.
Figure 66:
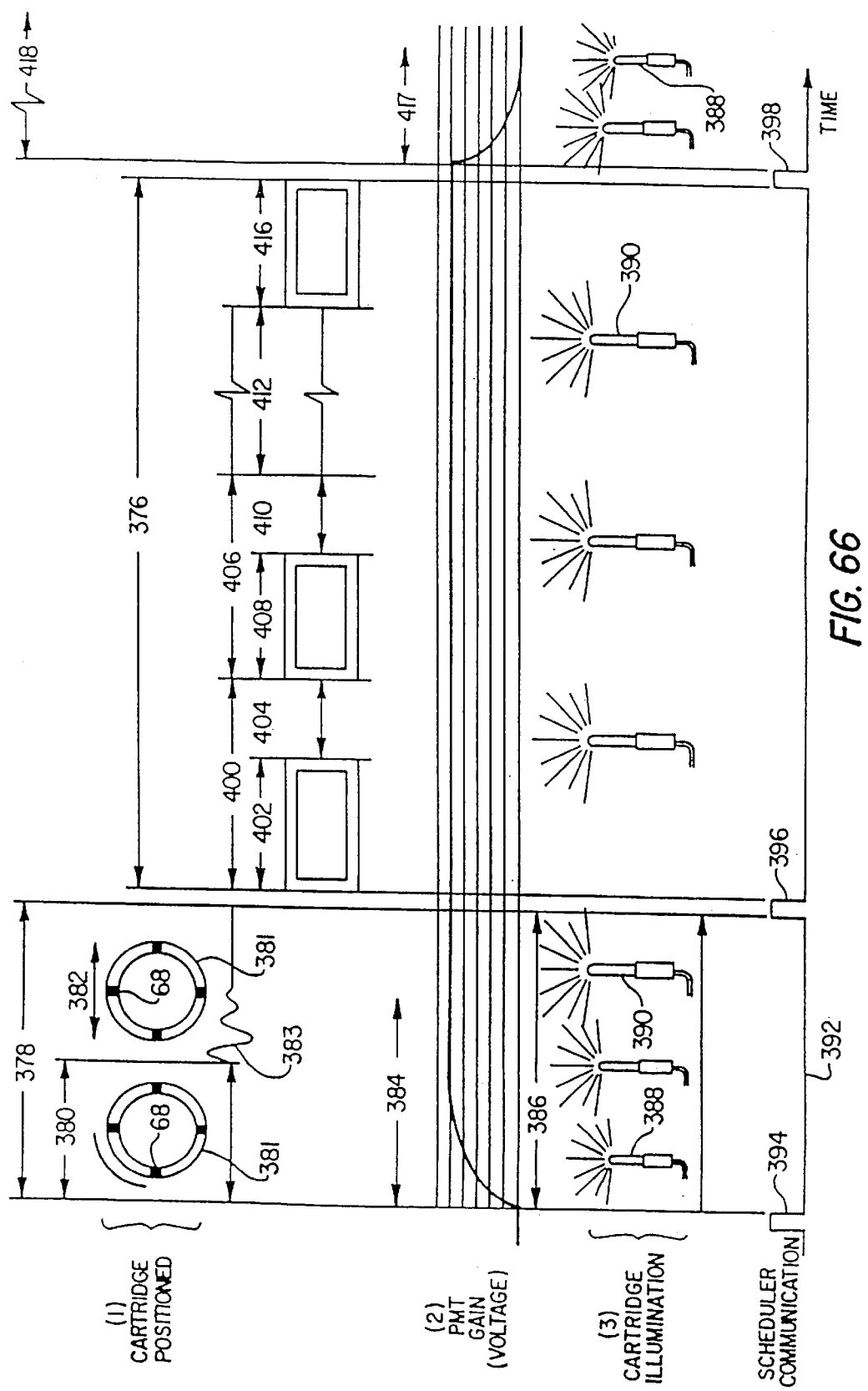
FIG. 66 is a pictorial time graph of the MEIA read sequence of the automated analytical system.
Figure 67:
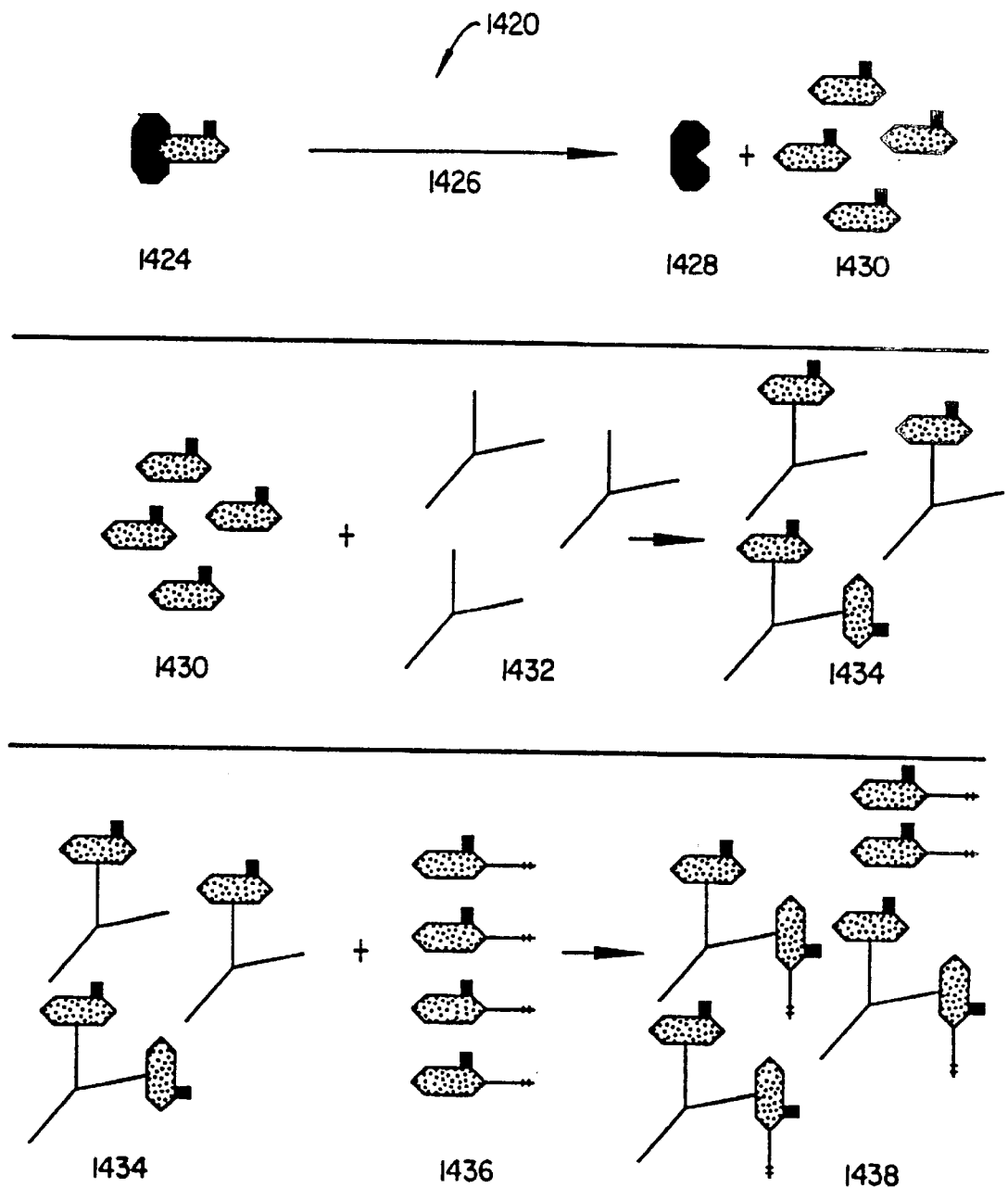
FIG. 67 is a schematic reaction sequence of the FPIA for T4 performed on the automated analytical system.
Figure 68:
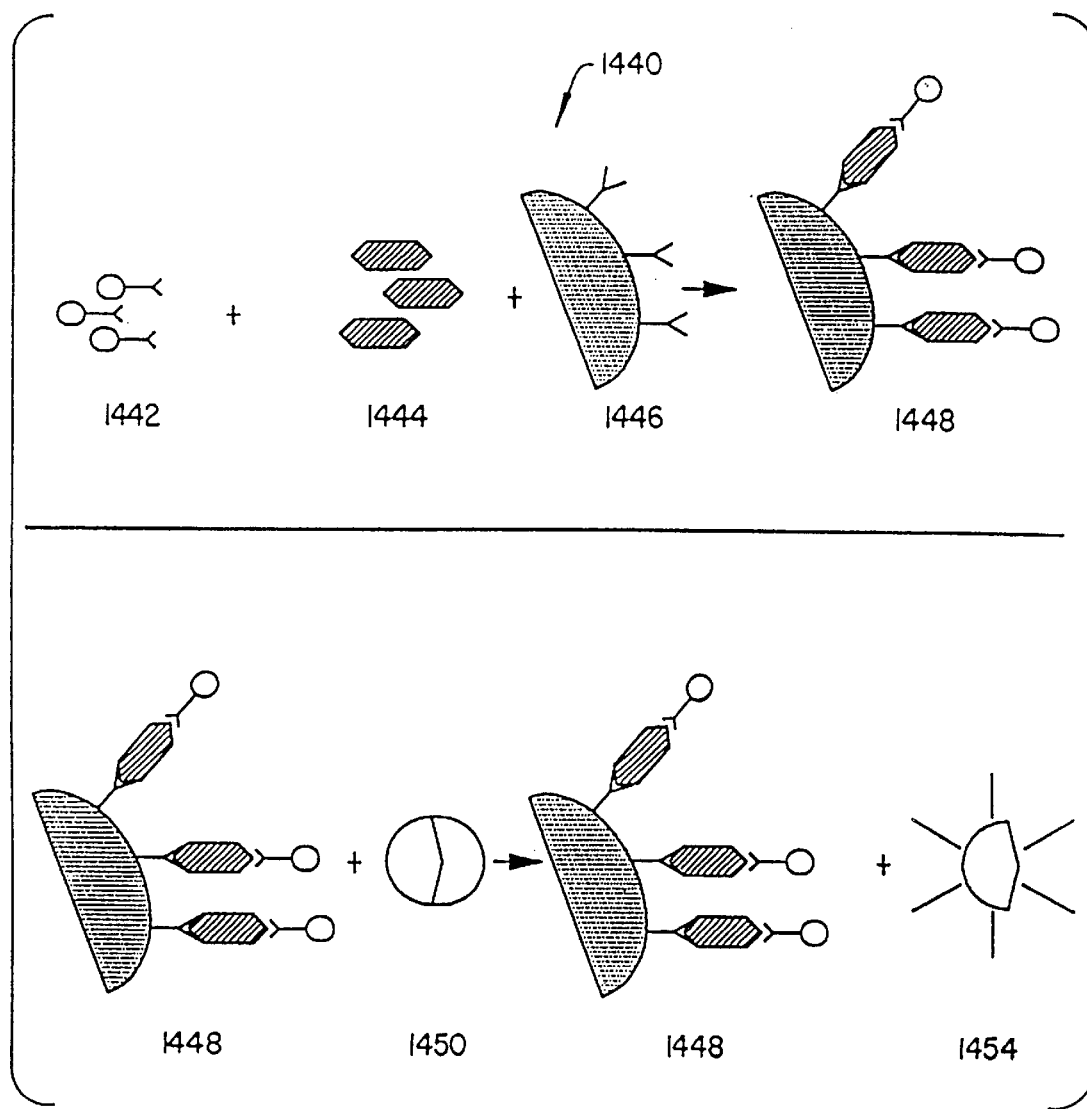
FIG. 68 is a schematic reaction sequence of a one-step sandwich MEIA performed on the automated analytical system.
Figure 69:
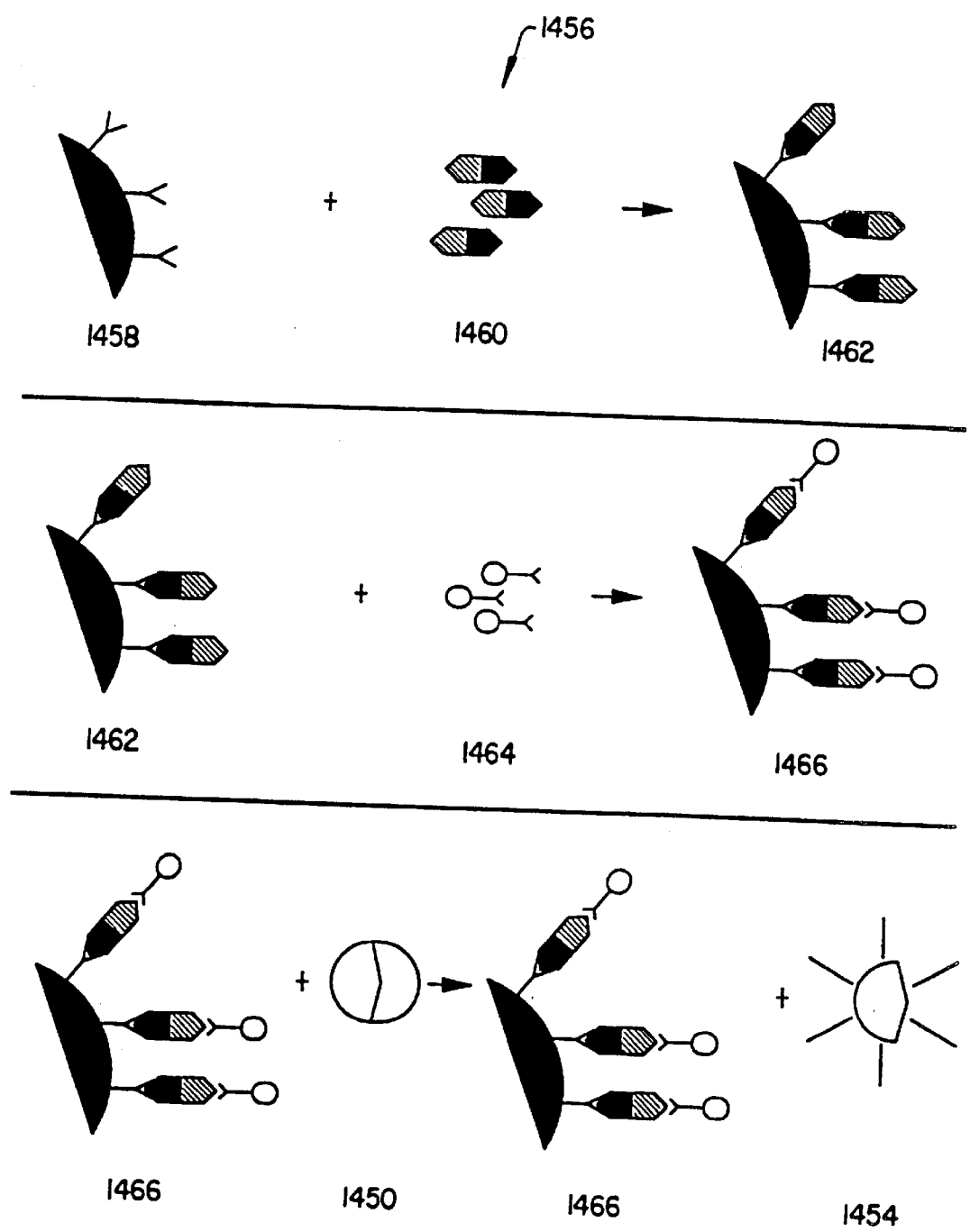
FIG. 69 is a schematic reaction sequence of a two-step sandwich MEIA performed on the automated analytical system.

The operation of the optics control system 284 in conjunction with the FPIA and MEIA optics systems 284, 361 can best be shown by the pictorial time graphs in FIGS. 65 and 66, respectively, which illustrate a simultaneous sequence of events. Referring to FIG. 65, time is divided into the following operational periods: the preread activity period 316, the read sequence period 314, and the normalization period 352. Each operational period is initiated by communications between the scheduler 256 and the OSP 254 as represented by communication signals 334, 336, 338 on the time line 332. During the period of each communication signal 334, 336, 338, the scheduler 256 determines the amount of time necessary to simultaneously accomplish all the events required for the corresponding operational period which is initiated by the trailing edge of the communication signal. More specifically, when the scheduler 256 determines the duration of the preread activity period 316, the trailing edge of the communication signal 334 initiates the preread activity period 316 during which the following events occur: (1) the cuvette 140 is positioned by the carousel represented symbolically at 319 to be read by the PMT 308, (2) the polarization state of the liquid crystal 298 is properly set, (3) the gain of the PMT 308 is set, and (4) the intensity of the lamp 286 is increased to a level sufficient to illuminate the FPIA mixture in the cuvette 140.

During the first event, the scheduler 256 allots enough time 318 for the carousel 319 to rotate the cuvette 140 to the proper position to be read. When the carousel 319 stops, the scheduler 256 then allots a predetermined amount of time 320 for the carousel 319 to stop moving or oscillating as indicated by the decaying sinusoidal curve 321. During the second event, the scheduler 256 allots enough time 322 for the OSP 254 to transition the liquid crystal 298 from a vertical state of polarization represented by the vertically-lined icon to a horizontal polarization represented by the horizontally-lined icon, the slanted-line icon therebetween representing the transition period. During the third event, the scheduler 256 allots enough time 324 for the OSP 254 to adjust the gain of the PMT 308. And finally, during the fourth event, the scheduler 256 allots enough time 326 for the OSP 254 to increase the intensity of the tungsten lamp 286 from a standby intensity 328, simmer state, to a higher full intensity 330, burn state, sufficient for illuminating the FPIA mixture in the cuvette 140. Cycling the lamp 286 from off to the full intensity 330 consumes too much time for a rapid and continuously operating analytical system and shortens the life of the lamp 286. The standby intensity 328 is sufficiently low to extend the life of the lamp 286, but sufficiently close to its thermal operating point to facilitate a rapid increase to the full intensity 330 required for illuminating the FPIA mixture within the allotted period of time 326. This feature is critical in a continuously operating analytical system not only because it extends the life of the lamp 286, but also because it stabilizes the full intensity 330 by maintaining an elevated temperature. Although other events occur during preread activity period 316, those just described are most relevant to the instant invention.

The scheduler 256 also determines the proper duration of the read sequence period 314 during the communication period 336, the trailing edge of which initiates the read sequence period 314 while holding the gain of the PMT 308 and the illumination of the tungsten lamp 286 constant after the preread activity period 316. During the read sequence period 314, the scheduler 256 allots enough time 342 for the PMT 308 to sense the energy level of the light emitted from the fluorescing mixture in the cuvette 140 during horizontal polarization as represented by the two horizontally-lined icons and send the corresponding analog signals to the DSP 250. The scheduler 256 then allows enough time 346 for the OSP 254 to transition the liquid crystal 298 from horizontal to vertical polarization as represented by the slanted-line icon. At the end of the read sequence period 314, the scheduler 256 allots enough time 348 for the PMT 308 to sense the energy level of the light emitted from the fluorescing mixture in the cuvette 140 during vertical polarization as shown by the vertical-lined icons and send the corresponding analog signals to the DPS 250. After the read sequence period 314 and during the normalization period 352, the OSP 254 automatically returns the liquid crystal 298 back to its normal state as indicated by the icons, reduces the gain of the PMT 308, and reduces the intensity of the tungsten lamp 286 back tot he standby intensity 328. The scheduler 256 is free to initiate another period sequence at any time during the period of unspecified length 354. The OSP 254 transmits all the data collected during the read sequence period 314 to the CPU 255 during the scheduler communication period 338.

The operation of the optics control system 248 in conjunction with the MEIA optic system 361 is shown in FIG. 66 wherein time is divided into the following similar operational periods: the preread activity period 378, the read sequence period 276, and the normalization period 417. Each operational period is initiated by communication between the scheduler 256 and the OSP 254 as represented by communication signals 394, 396, 398 on the time line 392. During the period of each communication signal 394, 396, 398, the scheduler 256 determines the amount of time necessary to simultaneously accomplish all the events required from the corresponding operational period which is initiated by the trailing edge of the communication signal. More specifically, when the scheduler 256 determines the duration of the preread activity period 378, the trailing edge of the communication signal 394 initiates the preread activity period 378 during which the following events occur: (1) the MEIA cartridge 68 is positioned by the carousel represented symbolically at 381 to be read by the PMT 374, (2) the gain of the PMT 374 is set, and (3) the intensity of the mercury vapor lamp 364 is increased to a level sufficient to illuminate the MEIA mixture in the MEIA cartridge 68.

During the first event, the schedule 256 allots enough time 380 for the carousel 381 to rotate the cartridge 68 to the proper position to be read. When the carousel 381 stops, the scheduler 256 then allots a predetermined time 382 for the carousel 381 to stop moving or oscillating as indicated by the decaying sinusoidal curve 383. During the second event, the scheduler 256 allots enough time 384 for the OSP 254 to adjust the gain of the PMT 374. During the third event, the scheduler 256 allots enough time 386 for the OSP 254 to increase the intensity of the mercury lamp 364 from a standby intensity 388, simmer state, to a full intensity 390, burn state, sufficient for illuminating the MEIA mixture in the cartridge 68. Cycling the lamp 364 from off to the full intensity 390 consumes too much time for a rapid and continuously operating analytical system and shortens the life of the lamp 364. In order to extend the life of the lamp 364, a means for maintaining the thermal operatong point of the lamp 364 must be employed for periods of time when the lamp 364 is not needed for illumination. Either of two methods are used. One method is to operate the lamp 364 at a current which is sufficiently low to extend the life of the lamp 364, but sufficiently close to its thermal operating point to facilitate a rapid increase to the full intensity 390 required for illuminating the MEIA mixture within the allotted period of time 386. The other method of maintaining the lamp 364 close to its thermal operating point is to encase the lamp 364 in a heater housing 363, which is controlled so as to maintain the lamp 364 at an elevated temperature of approximately 70 degrees C. at all times. This feature is critical to a continuously operating analytical system not only because it extends the life of the lamp 364, but also because it stabilizes the full intensity 390 by maintaining an elevating temperature. Although other events occur during the preread activity period 378, those just described are most relevant to the instant invention.

The scheduler 256 also determines the proper direction of the read sequence period 376 during the communication period 396, the trailing edge of which initiates the read sequence period 376 while holding the gain of the PMT 364 and the illumination of the mercury vapor lamp 364 constant after the preread activity period 378. During the read sequence period 376, the scheduler 256 allocates enough time 400 for the PMT 374 to sense the energy level of light emitted from the fluorescing mixture in the cartridge 68 during a sub-read period 402 and send the corresponding analog signals to the DSP 260 during a dwell period 404. The read sequence period 376 continues with similar cycles like cycle 406, including sub-read period 408 and dwell period 410, as represented by the broken time line 412. After about eight (8) of such sub-readings depending upon the assay being performed, the read sequence period 376 and during the normalization period 417, the OSP 254 automatically reduces the gain of the PMT 374 and the intensity of the mercury vapor lamp 364 back to the standby intensity 388. The scheduler 256 is free to initiate another preread sequence at any time during the period of unspecified length 418. The OSP 254 also transmits all of the data collected during the read sequence period 376 to the CPU 255 during the scheduler communication period 398.

It is to be understood that the optics control system of the present invention can be utilized in similar automated instruments requiring distributed processing and control. For example, the invention can be used in conjunction with performing assays other than the FPIA and MEIA assays. Furthermore, the architecture of the optical signal processor 254 and the digital signal processors 250, 260 can be combined into a single unit operating as a slave processor for the CPU 255. Other processing architectures similar to the one disclosed can be utilized in accordance with the invention.

What is claimed is:

1. A device for supporting a plurality of containers for holding liquid test samples, said device forming one of a plurality of segments positionable on a carousel, said carousel for knitting the liquid test samples on an automated analytical system for performing assays, said device comprising:

a base formed by opposing inner and outer sidewalls, said sidewalls being arcuate and vertical, said sidewalls closed by endwalls extending radially outwardly from the inner sidewall to the outer sidewall, said base having a bottom defined by the bottoms of the vertical sidewalls and endwalls and a top defined by the tops of the vertical sidewalls and endwalls, the bottom of said base adapted for mounting said device on the carousel; and a frame formed by a shelf having openings sized for receiving the containers, said frame having an arcuate shape defined generally by the tops of the vertical sidewalls and endwalls of said base, and at least two legs extending from the shelf to the top of said base for supporting the shelf thereon.

2. The device according to claim 1, including a plurality of tubular sleeves positioned in said base to hold said containers therein, said containers being tubular in shape.

* * * * *

UNITED STATES PATENT AND TRADEMARK OFFICE
CERTIFICATE OF CORRECTION

PATENT NO. : 6,190,617 B1  
DATED : February 20, 2001  
INVENTOR(S) : Frederic L. Clark et al.

Page 1 of 1

It is certified that error appears in the above-identified patent and that said Letters Patent is hereby corrected as shown below:

<u>Column 68,</u>  
Line 10, replace "said carousel for knitting" with -- said carousel for kitting --.

Signed and Sealed this

Twelfth Day of March, 2002

Attest:

JAMES E. ROGAN  
*Attesting Officer*  *Director of the United States Patent and Trademark Office*